(12) United States Patent
Friebe et al.

(10) Patent No.: US 8,685,652 B2
(45) Date of Patent: Apr. 1, 2014

(54) TARGETS AND COMPOUNDS FOR THERAPEUTIC INTERVENTION OF HIV INFECTION

(75) Inventors: Annette Friebe, Burscheid (DE); Hanjo Hennemann, Neuss (DE); Claudia Carl, Bonn (DE); Nina Schürmann, Unkel (DE); Sabine Wirths, Ruppichteroth-Winterscheid (DE)

(73) Assignee: Nexigen GmbH, Bonn (DE)

( * ) Notice: Subject to any disclaimer, the term of this patent is extended or adjusted under 35 U.S.C. 154(b) by 622 days.

(21) Appl. No.: 12/673,292

(22) PCT Filed: Aug. 13, 2008

(86) PCT No.: PCT/EP2008/060631
§ 371 (c)(1),
(2), (4) Date: Aug. 9, 2010

(87) PCT Pub. No.: WO2009/021971
PCT Pub. Date: Feb. 19, 2009

(65) Prior Publication Data
US 2011/0065198 A1    Mar. 17, 2011

Related U.S. Application Data

(60) Provisional application No. 60/955,491, filed on Aug. 13, 2007.

(30) Foreign Application Priority Data

Aug. 13, 2007 (EP) ..................... 07015899

(51) Int. Cl.
*G01N 33/53* (2006.01)

(52) U.S. Cl.
USPC ........................................... 435/7.1

(58) Field of Classification Search
None
See application file for complete search history.

(56) References Cited

FOREIGN PATENT DOCUMENTS

| WO | WO 2005/004798 A2 | 1/2005 |
|----|-------------------|--------|
| WO | WO 2005/023985 A2 | 3/2005 |
| WO | WO 2005/024422 A2 | 3/2005 |
| WO | WO 2007/044565 A2 | 4/2007 |

OTHER PUBLICATIONS

Martin et al., Journal of Immunology, 1994, 152:330-342.*
Ayyavoo et al., "Immunogenicity of a novel DNA vaccine cassette expressing multiple human immunodeficiency virus (HIV-1) accessory genes", AIDS, vol. 14, No. 1 (2000), pp. 1-9.
Database UniProt [Online], Nov. 1, 1997, "RecName: Full=Eukaryotic initiation factor 4A-II; Short=eIF-4A-II; Short=eIF4A-II; EC=<A HREF=http://srs.ebi.ac.uk/srsbin/cgi-bin/wgetz?[enzyme-ECNumber:3.6.1.*]+-e >3.6.1.- </A>; AltName: Full=ATP-dependent RNA helicase eIF4A-2", XP002502238, 2 pgs.
Madani et al., "Implication of the lymphocyte-specific nuclear body protein Sp 140 in an innate response to human immunodeficiency virus type 1", Journal of Virology Nov. 2002, vol. 76, No. 21 (2002), pp. 11133-11138.
Feng et al., "Ring finger protein ZIN interacts with human immunideficiency virus type 1 Vif", Journal of Virology Oct. 2002, vol. 78, No. 19 (2004), pp. 10574-10581.
Navarro et al., "Recent insights into HIV-1 Vif", Current Opinion in Immunology, vol. 16, No. 4 (2004), pp. 477-482.
Lake et al., "The role of Vif during HIV-1 infection: interaction with novel host cellular factors", Official Publication of the Pan American Society for Clinical Virology Feb. 2003, vol. 26, No. 2, (2003), pp. 143-152.
Brachmann et al., "Tag games in yeast: the two-hybrid system and beyond", Current Opinion in Biotechnology, vol. 8, No. 5 (1997), pp. 561-568.
Chertova et al., "Proteomic and biochemical analysis of purified human immunodeficiency virus type 1 produced from infected monocyte-derived macrophages", Journal of Virology, vol. 80, No. 18 (2006), pp. 9039-9052.
Cantin et al., "Plunder and stowaways: Incorporation of cellular proteins by enveloped viruses", Journal of Virology, vol. 79, No. 11 (2005), pp. 6577-6587.
Nam et al., "Structural basis for the function and regulation of the receptor protein tyrosine phosphatase CD45", Journal of Experimental Medicine, vol. 201, No. 3 (2005), pp. 441-452.
Hrecka et al., "Lentiviral Vpr usurps Cul4-DDB1[VprBP] E3 ubiquitin ligase to modulate cell cycle", Proceedings of the National Academy of Sciences of the United States of America, vol. 104, No. 28 (2007), pp. 11778-11783.
Schröfelbauer et al., "Human immunodeficiency virus type 1 Vpr induces the degradation of the UNG and SMUG uracil-DNA glycosylases", Journal of Virology Sep. 2005, vol. 79, No. 17 (2005).
Wen et al., "The HIV1 protein Vpr acts to promote G(2) cell cycle arrest by engaging a DDB1 and Cullin4A-containing ubiquitin ligase complex using VprBP/DCAF1 as an adaptor", Journal of Biological Chemistry, vol. 282, No. 37 (2007), pp. 27046-27057.
Database UniProt [Online], Feb. 20, 2007, "SubName: Full=Heat shock 70kDa protein 1A", XP002513145, 1 pg.
Database UniProt [Online], Aug. 1, 1988, "RecName: Full=Heat shock protein HSP 90-beta; Short=HSP 90; AltName: Full=HSP 84", XP002513146, 6 pgs.
Database JPO Proteins [Online], Jan. 23, 2007, Compositions and Methods for the Diagnosis and Treatment of Tumor:, XP002513147, 1 pg.
Database UniProt [Online], Dec. 1, 2001, "SubName: Full=Putative uncharacterized protein; Flags: Fragment", XP002513148, 1 pg.
Database UniProt [Online], Feb. 1, 1997, "RecName: Full=Heat shock protein 105 kDa; AltName: Full=Heat shock 110 kDa protein; AltName: Full=Antigen NY-CO-25", XP002513149, 4 pgs.
Barak, O., et al.; "HBV X Protein Targets HIV Tat-Binding Protein 1", Virology, vol. 283, pp. 110-120, 2000.
Baraz, L., et al.: "The Vif Protein of Human Immunodeficiency Virus Type 1 (HIV-1): Enigmas and Solution", Current Medicinal Chemistry, vol. 11, pp. 221-231, 2003.
Bovolenta, C.: "Blocking HIV-1 Vif Restores a Natural Mechanism of Intracellular Antiviral Defense", Current Drug Targets—Immure, Endocrine & Metabolic Disorders, vol. 4, pp. 257-263, 2004.

(Continued)

*Primary Examiner* — Nicole Kinsey White
(74) *Attorney, Agent, or Firm* — Fanelli Haag & Kilger PLLC

(57) ABSTRACT

Novel drug targets and antiviral agents are provided for the therapeutic intervention of lentiviral diseases, in particular AIDS.

4 Claims, 9 Drawing Sheets

(56) References Cited

OTHER PUBLICATIONS

Cantin, R., et al.: "Plunder and Stowaways: Incorporation of Cellular Proteins by Enveloped Viruses", Journal of Virology, vol. 79(11), pp. 6577-6587, 2005.

Chiu, Y-L, et al.; Multifaceted Antiviral Actions of APOBEC3 Cytidine Deaminases, Trends in Immunology, vol. 27(6), 291-297, 2006.

European Examination Report dated Mar. 26, 2010.

International Search Report dated Feb. 13, 2009.

Kruse, C., et al.: "Protein-Protein Interaction Screening with Ras-Recruitment System", Signal Transduction, vol. 6, pp. 198-208, 2006.

Murakami, Y., et al.: "A Mammalian Two-Hybrid Screening System for Inhibitors of Interaction Between HIV Nef and the Cellular Tyrosine Kinase Hck", Antiviral Research, vol. 55, pp. 161-168, 2002.

Partial European Search Report dated Feb. 21, 2008.

Van Criekinge, W., et al.: "Yeast Two-Hybrid: State of the Art", Biological Procedures Online, vol. 2(1), pp. 1-38, 1999.

Kyono, K. et al., "Human Eukaryotic Initiation Factor 4AII Associates with Hepatitis C Virus NS5B Protein in Vitro", Biochemical and Biophysical Research Communications, 292:659-666, 2002.

Tacken, M.G., "VP1, the RNA-dependent RNA polymerase and genome-linked protein of infectious bursal disease virus, interacts with the carboxy-terminal domain of translational eukaryotic initiation factor 4AII," Arch. Virol, 149:2245-2260, 2004.

Bondar, T. et al., "Cu14A and DDB1 Associate with Skp2 to Target $p27^{Kip1}$ for Proteolysis Involving the COP9 Signalosome," Molecular and Cellular Biology, vol. 26, No. 7, pp. 2531-2539, 2006.

Nicholas, R.S. et al.,"The role of the PTPRC (CD45) mutation in the development of multiple sclerosis in the North West region of the United Kingdom," Journal of Neurol Neurosurg. Psychiatry, vol. 74, pp. 944-945, 2003.

\* cited by examiner

FIG. 1
Galactose, 37°C
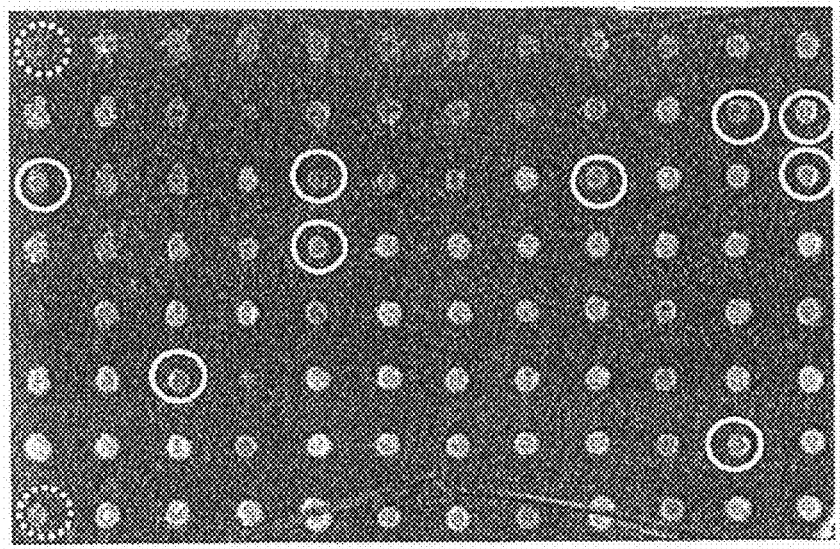
Glucose, 37°C
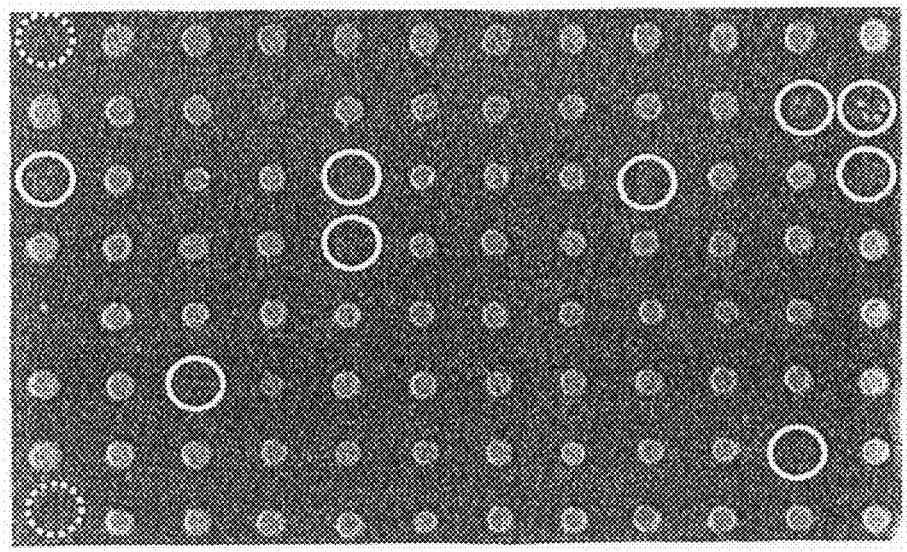

FIG. 2

| | Galactose 37°C | Glucose 37°C | Glucose 24°C |
|---|---|---|---|
| CSDE1 + Sos-vif | | | |
| CSDE1 + Sos-cJun | | | |
| CTCF + Sos-vif | | | |
| CTCF + Sos-cJun | | | |
| EIF4A2 + Sos-vif | | | |
| EIF4A2 + Sos-cJun | | | |
| HERC4 + Sos-vif | | | |
| HERC4 + Sos-cJun | | | |
| HNRPU + Sos-vif | | | |
| HNRPU + Sos-cJun | | | |
| HSPA1 + Sos-vif | | | |
| HSPA1 + Sos-cJun | | | |
| HSPA5 + Sos-vif | | | |
| HSPA5 + Sos-cJun | | | |
| HSPA8 + Sos-vif | | | |
| HSPA8 + Sos-cJun | | | |
| MRCL3 + Sos-vif | | | |
| MRCL3 + Sos-cJun | | | |
| NUP50 + Sos-vif | | | |
| NUP50 + Sos-cJun | | | |
| PTEN + Sos-vif | | | |
| PTEN + Sos-cJun | | | |
| PTGES3 + Sos-vif | | | |
| PTGES3 + Sos-cJun | | | |
| SDCCAG1 + Sos-vif | | | |
| SDCCAG1 + Sos-cJun | | | |
| TOM1L1 + Sos-vif | | | |
| TOM1L1 + Sos-cJun | | | |
| TPT1 + Sos-vif | | | |
| TPT1 + Sos-cJun | | | |

FIG. 7

| | Galaktose 37° C | Glucose 37° C |
|---|---|---|
| PPM1B+SOS-vif | | |
| PPM1B+SOS-cJun | | |
| CCT5+SOS-vif | | |
| CCT5+SOS-cJun | | |
| Rab21+SOS-vif | | |
| Rab21+SOS-cJun | | |
| Rab4A+SOS-vif | | |
| Rab4A+SOS-cJun | | |
| KIAA1429+SOS-vif | | |
| KIAA1429+SOS-cJun | | |
| RBM39+SOS-vif | | |
| RBM39+SOS-cJun | | |
| PDIA3+SOS-vif | | |
| PDIA3+SOS-cJun | | |
| RAG2+SOS-vif | | |
| RAG2+SOS-cJun | | |
| CAB39+SOS-vif | | |
| CAB39+SOS-cJun | | |
| VCP+SOS-vif | | |
| VCP+SOS-cJun | | |
| Cul4+SOS-vif | | |
| Cul4+SOS-cJun | | |

TARGETS AND COMPOUNDS FOR THERAPEUTIC INTERVENTION OF HIV INFECTION

This application is a U.S. national phase application under 35 U.S.C. §371 of International Application Number PCT/EP2008/060631, filed Aug. 13, 2008, which claims priority to European Application Number 07015899.3, filed Aug. 13, 2007 and U.S. Provisional Application No. 60/955,491, filed Aug. 13, 2007, each of which is incorporated herein by reference.

SEQUENCE LISTING

The instant application contains a Sequence Listing which has been submitted via EFS-Web and is hereby incorporated by reference in its entirety. Said ASCII copy, created on Aug. 6, 2010, is named 00054701.txt, and is 105,040 bytes in size.

FIELD OF THE INVENTION

The present invention generally relates to the technical field of molecular biology and virology, respectively, and the development of antiviral drugs in particular. In one aspect, the present invention relates to a method for identifying and cloning nucleic acid molecules encoding a new class of proteins or fragments thereof, capable of interacting with proteins associated with the Human Immunodeficiency Virus (HIV) and thus being suitable either alone or in complex with the HIV protein for serving as a target for the development of antiviral drugs. In this context, the present invention provides novel HIV-interacting proteins and complexes as well as antibodies which is specifically recognize and bind to the complex or to specific domains of HIV proteins. A further object of the present invention is a method for identifying and providing anti-HIV drugs which are capable of modulating formation and/or stability of a complex of a human host cellular protein with an HIV protein. Thus, the present invention also relates to compositions useful for detecting and targeting complexes between HIV proteins and human proteins, which are believed to be essential in establishing viral infection.

BACKGROUND OF THE INVENTION

AIDS (acquired immunodeficiency syndrome) is one of the leading causes of death in the developing world, its spread reaching pandemic proportions. In 1984, the etiologic agent of AIDS was discovered as the Human Immunodeficiency Virus (HIV), being a retrovirus which is a member of the lentivirus subfamily. The Lentiviridae include non-oncogenic retroviruses which usually infect cells of the immune system, particularly macrophages and T cells, causing persistent infections in diseases with long incubation periods and cytopathic effects in infected cells, such as syncytia and cell death. Lentiviral infections are not cleared by the immune system, and lead to accumulated immunologic damage over a period of many years.

HIV which is a member of the Lentiviridae is a retrovirus, i.e. containing an RNA genome and reverse transcriptase activity, and therefore, during its growth cycle, HIV copies its RNA into proviral DNA, which is able to integrate into the chromosomal DNA of the host cell (provirus). Due to its retroviral nature and small size of its genome, HIV replication is strongly dependent on the host's cell machinery. Thus, HIV uses the transcriptional and translational machinery of the host to express viral RNA and proteins and to finally release mature viruses from the cell by budding from the cytoplasmic membrane. In the case of HIV, viral replication results in the death of host's helper T cell, which leads to a state of severe immunodeficiency (AIDS), to the development of various malignancies and opportunistic infections, and ultimately to the death of the infected organism.

Besides the "usual" genes of the HIV genome such as env (encoding the virus' envelope protein), gag (encoding the internal proteins responsible for forming the capsid- and nucleocapsid structures) and pol (encoding the enzymes reverse transcriptase, integrase and protease), the transcriptional transactivator (tat) and the regulator of viral expression (rev) genes produce small non-virion proteins which are essential for viral replication. Also several genes which are not implicated in viral expression are encoded by HIV such as vif, vpr, vpu and nef.

The treatment of HIV disease has been significantly advanced by recognizing that the HIV life cycle can be interfered with at many levels by for example inhibiting virus' reverse transcription, inhibiting its protease activity or fusion. Accordingly, three major classes of drugs have been developed: reverse transcriptase inhibitors, protease inhibitors and fusion inhibitors, and currently, there are about 25 antiretroviral drugs approved to treat individuals infected with HIV. Furthermore, it is known that the combination of different drugs with specific activities against different biochemical functions of the virus (combination therapy) can help reducing the rapid development of drug resistant viruses that was observed in response to single drug treatments.

However, even the current "highly active anti-retroviral therapy" (HAART), which is based on a treatment of infected persons with a combination of antiviral drugs from at least two of the above-referenced drug classes, and which to date is the only efficacious treatment to reduce progression and spread of AIDS, is associated with several drawbacks and limitations when used long-termed, such as adherence to a complex dosing regimen, side effect toxicity and elevated costs; see for example Richman, Nature 410 (2001), 995-1001. Additionally, the high genetic and antigenic variability of HIV, due to the high mutation rate of its genome, in combination with inadequate compliance, is responsible for resistance to HAART drugs, because of which although the use of HAART has greatly reduced the number of deaths due to HIV/AIDS, complete viral suppression was not achieved.

In addition to the development of inhibitors of the "essential" viral enzymes (reverse transcriptase, protease and integrase), research is currently focussed on targeting HIV accessory proteins. For the HIV accessory proteins Vif, Vpu, Vpr, and Nef the precise biochemical mechanisms are still under investigation, however, there is increasing evidence to suggest that none of these proteins has catalytic activity on its own, but rather, they appear to function as "adapter molecules" that connect other viral or cellular factors to various cellular pathways.

One of the four accessory proteins, the virion infectivity factor (Vif), is a small basic phosphoprotein with a molecular mass of 23 kDa and composed of 192 amino acids, which is synthesized in a Rev-dependent manner during the late stages of virion production. Homologs of Vif exist in all lentiviruses, with the only exception being equine infectious anaemia virus (EIAV), see Oberste & Gonda, Virus Genes 6 (1992), 95-102, and there is significant conservation among vif open reading frames of the different lentiviruses; see Sonigo et al., Cell 42 (1985), 369-382.

In case of HIV, Vif is generally required for viral replication in primary T cells. Furthermore, it is known to counteract suppression of HIV replication mediated by a host protein, i.e. the human apolipoprotein B mRNA-edlting enzyme-catalytic-polypeptide-like-3G (APOBEC3G), which is a member of the APOBEC cytodine deaminase family of enzymes. APOBEC3G is known to be packaged into retroviral virions (infectious mature virus particles) and to deaminate deoxycytidine to deoxyuridine in newly synthesized viral minus-strand DNA, thereby inducing G-to-A hypermutation. The interaction of Vif with APOBEC3G in the virus producing cell prevents APOBEC3G from being incorporated into virions and thus prevents APOBEC3G from acting on newly synthesized HIV cDNA. To the contrary, Vif was shown to interact with cellular proteins Cul5, ElonginB, ElonginC, and Rbx1 to form an E3 ubiquitin ligase complex for APOBEC3G ubiquitination (see, for example, Yu at al., Science 302 (2003), 1056-1060), thereby upon binding to APOBEC3G inducing its ubiquitination and proteosomal degradation and finally the elimination of APOBEC3G from cells, which enables HIV to produce infectious viruses.

Vif was also shown to interact with the Src tyrosine kinases Fyn and Hck resulting in a reduction of their catalytic activities; see for example Hassaine et al., J. Biol. Chem. 276 (2001), 16885-16893; and to interact with the zinc finger protein inhibiting NF-KB; see Feng et al., J. Virol. 78 (2004), 10574. Since the protein interaction network of Vif in the host cell being responsible for the functional role of the viral accessory protein is only partially understood, recently novel functions in cell cycle regulation of infected cells were described by Wang et al., Virology 359 (2007), 243-252.

However, none of the human proteins identified so far to interact with HIV accessory proteins could be shown to be suitable as a target for anti-HIV drug development. Thus, there is still a need for providing anti-HIV drug targets that supplement the "essential" proteins, reverse transcriptase, protease and integrase, in the combined anti-HIV therapy or provide an alternative thereto.

SUMMARY OF THE INVENTION

The present invention relates to novel drug targets useful in the treatment of viral diseases. More particularly, the present invention is directed to human proteins interacting with the HIV-associated Vif-protein and drugs interfering with said interactions.

Experiments performed in accordance with the present invention surprisingly revealed a new class of proteins interacting with a viral disease associated protein, in particular Vif, which hitherto were not known to be a target of Vif. Because of the experimental system used for the identification of the proteins binding to the HIV protein it is prudent to expect said host proteins identified in accordance with the method of the present invention to truly bind to the proteins associated with the respective viral disorder such as AIDS. Accordingly, the so identified proteins as well as protein-protein interaction and complex formation between HIV Vif and host protein, respectively, provide suitable targets for therapeutic intervention and design of agents, capable of modulating the same. In this context, the present invention provides both, nucleic acid molecules encoding the respective proteins interacting with the viral disease-associated protein and the proteins encoded by said nucleic acid molecules or obtainable according to the methods of the present invention as well as complexes comprising the viral disease-associated protein and the host (human) protein identified by the method of the present invention.

Furthermore, the present invention relates to an antibody that specifically binds either to the complex of the HIV protein and the human protein or to the binding domain of the HIV protein and the human protein, respectively, or it binds to a protein which by way of amino acid substitution, deletion and/or addition is no longer capable of forming a respective complex with Vif.

The present invention also concerns a method for screening compounds, capable of modulating a particular protein-protein interaction and complex formation and/or stability, respectively, as well as compounds obtainable according to said method and the use of said compounds for the preparation of a medicament for the treatment of lentiviral diseases. For example, appropriate antiviral drugs maybe derived from the human protein identified as protein binding partner of the HIV accessory protein by way of identifying the binding domain and designing corresponding peptides or mimetics thereof, capable of interfering with the interaction of the native protein with the HIV accessory protein; see, e.g., Example 4.

According to another aspect, the present invention relates to a pharmaceutical composition comprising an antibody or compound according to the present invention and optionally a pharmaceutical acceptable carrier. In addition, a kit is provided, useful for performing the methods of the present invention.

BRIEF DESCRIPTION OF THE DRAWINGS

The figures illustrate the invention and show:

FIG. 1: illustrates growth of yeast cells upon simultaneous expression of the two fusion proteins (the first fusion protein comprising Vif fused to Sos [via a linker] and the second fusion protein comprising a protein derived from the thymus library fused to a membrane localization domain). In particular, FIG. 1 shows the interaction of the two proteins upon which Sos is recruited to the cell membrane activating the Ras signalling pathway resulting in a detectable phenotype, i.e. allowing the growth of yeast cells even at the restrictive temperature of 37° C. Expression of the first fusion protein is under the control of the constitutive alcohol dehydrogenase (ADH) promoter, however, since expression of the second fusion protein is under the control of a GAL1 promoter, cell growth at the restrictive temperature is only detected upon galactose addition (left part). Addition of glucose represses GAL1 promoter dependent expression and did not lead to cell growth. Positive clones growing on galactose plates in comparison to glucose plates were identified and are indicated by white circles. Clones growing on both media were identified as revertants. Control yeast cells expressing a pair of known interacting proteins are indicated by dotted circles.

FIG. 2: shows the microbial growth response resulting from complexes of Vif protein and different host factors identified according to the method of the present invention. Binding specificity of the host proteins to Vif is also demonstrated. Growth of yeast cells at the restrictive temperature of 37° C. is dependent on the expression of host factors as well as of the interacting target protein Vif, since only upon the interaction of the host proteins with Vif the effector responsible for cell growth is recruited to the cell membrane. However, in case of a negative control target protein, cJun to which the identified host proteins most likely do not bind, no interaction and therefore no cell growth is detected. In particular, left column of FIG. 2 represent host proteins, identified according to the method of the present invention and sequenced after the respective and specific interaction with Vif was demonstrated.

Under screening conditions (column Galactose 37° C.) the expression of the host factors is induced and growth is dependent on their interaction with the Vif fusion protein. As can be seen, all host factors mediated growth only in combination with the Vif fusion protein, but not when combined with the heterologous cJun fusion protein. The third column (Glucose 37° C.) indicates host factor dependent growth, since repression of the host factor expression (glucose represses the GAL1 promoter driven expression cassette) abolished the growth response in all cases. Right column of FIG. 2 represents cell growth controls at the non-restrictive temperature (24° C.).

Figure 3A:
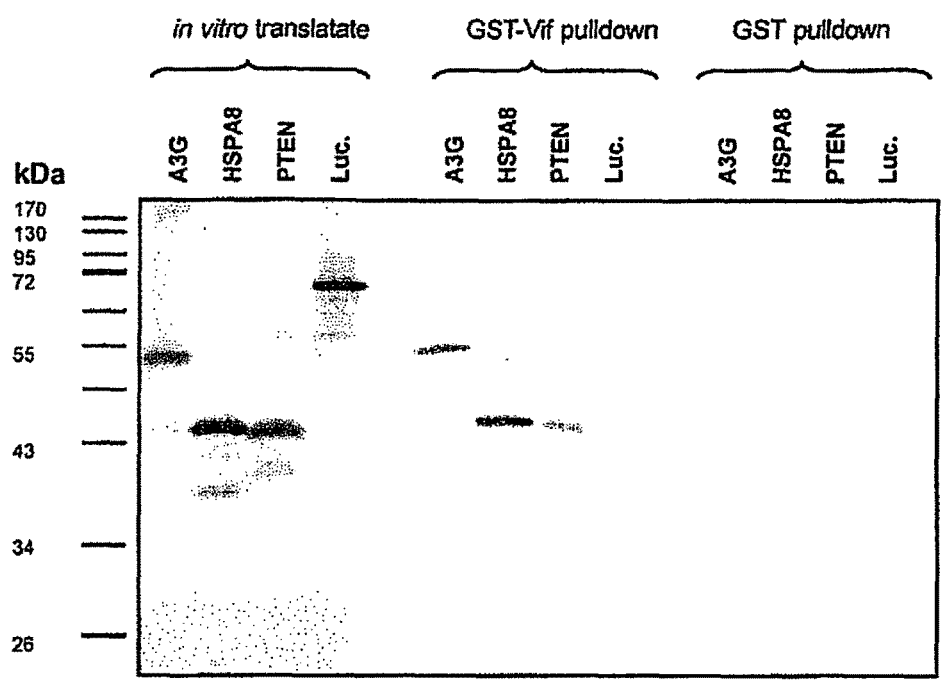

FIG. 3a: shows an autoradiography of a 12% sodium dodecyl sulphate (SDS) polyacrylamide gel representing the results of glutathione-S-transferase (GST) pull-down experiments. In particular, FIG. 3a shows the detection of interactions between GST-Vif and in vitro translated proteins.

Lane 1 to 4 represent radioactively labelled in vitro translated proteins, in particular, line 1 shows in vitro translated APOBEC3G (A3G); line 2 shows in vitro translated HSPA8; line 3 shows in vitro translated PTEN; and line 4 shows in vitro translated luciferase (Luc.).

Lanes 6 to 9 represent the respective pull-down results of the afore-mentioned radioactively labelled in vitro translated proteins by GST-Vif glutathione sepharose beads.

In particular, lane 6 shows GST-Vif and in vitro translated APOBEC3G (A3G; positive control); line 7 shows GST-Vif and in vitro translated HSPA8; line 8 shows GST-Vif and in vitro translated PTEN; and line 9 shows GST-Vif and in vitro translated luciferase (Luc.; negative control).

Lanes 11 to 14 represent the control for the specificity of the GST pulldown experiment, i.e. for the binding specificity of the in vitro translated proteins to Vif. Therefore, lanes 11 to 14 in particular represent the results of GST pull-down, wherein GST was used alone, i.e. without being fused to Vif. More particularly, lane 11 shows GST and in vitro translated APOBEC3G (A3G); line 12 shows GST and in vitro translated HSPA8; line 13 shows GST and in vitro translated PTEN; and line 14 shows GST and in vitro translated luciferase (Luc.). It is demonstrated that there is no unspecific binding of the in vitro translated proteins to GST alone.

Figure 3B:
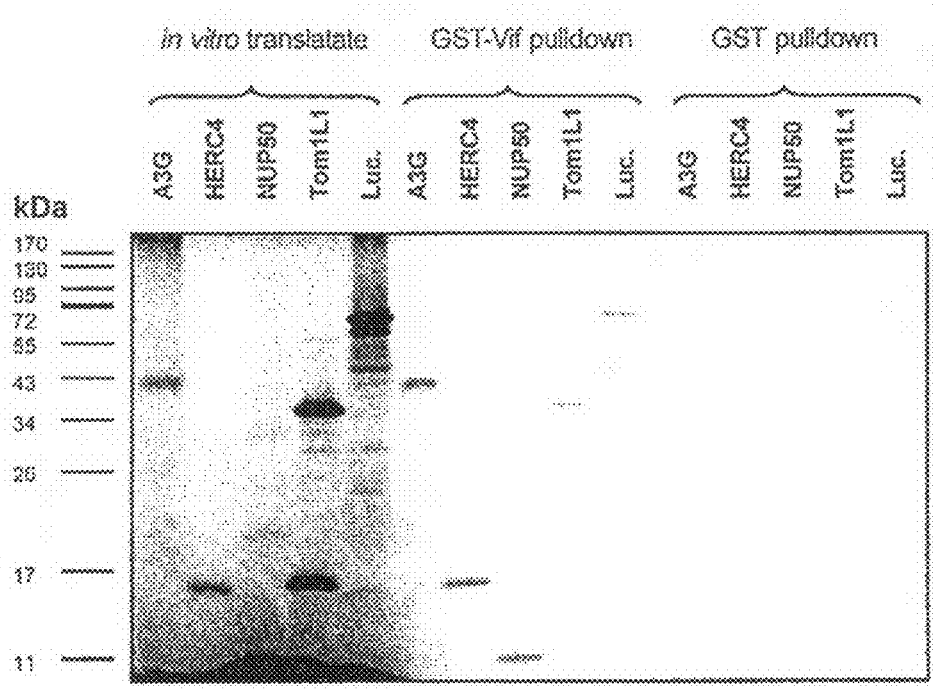

FIG. 3b: shows an autoradiography of a 12% sodium dodecyl sulphate (SDS) polyacrylamide gel representing the results of glutathione-S-transferase (GST) pull-down experiments. In particular, FIG. 3b shows the detection of interactions between GST-Vif and in vitro translated proteins.

Lane 1 to 5 represent radioactively labelled in vitro translated proteins, in particular, line 1 shows in vitro translated APOBEC3G (A3G); line 2 shows in vitro translated HERC4; line 3 shows in vitro translated NUP50, lane 4 shows in vitro translated TOM1L1; and line 5 shows in vitro translated luciferase (Luc.).

Lanes 6 to 10 represent the respective pull-down results of the afore-mentioned radioactively labelled in vitro translated proteins by GST-Vif glutathione sepharose beads.

In particular, lane 6 shows GST-Vif and in vitro translated APOBEC3G (A3G; positive control); line 7 shows GST-Vif and in vitro translated HERC4; line 8 shows GST-Vif and in vitro translated NUP50, line 9 shows GST-Vif and in vitro translated TOM1L1; and line 10 shows GST-Vif and in vitro translated luciferase (Luc.; negative control).

Lanes 11 to 15 represent the control for the specificity of the GST pulldown experiment, i.e. for the binding specificity of the in vitro translated proteins to Vif. Therefore, lanes 11 to 15 in particular represent the results of GST pull-down, wherein GST was used alone, i.e. without being fused to Vif. More particularly, lane 11 shows GST and in vitro translated APOBEC3G (A3G); line 12 shows GST and in vitro translated HERC4; line 13 shows GST and in vitro translated NUP50, line 14 shows GST and in vitro translated TOM1L1; and line 15 shows GST and in vitro translated luciferase (Luc.). It is demonstrated that there is no unspecific binding of the in vitro translated proteins to GST alone.

Figure 3C:
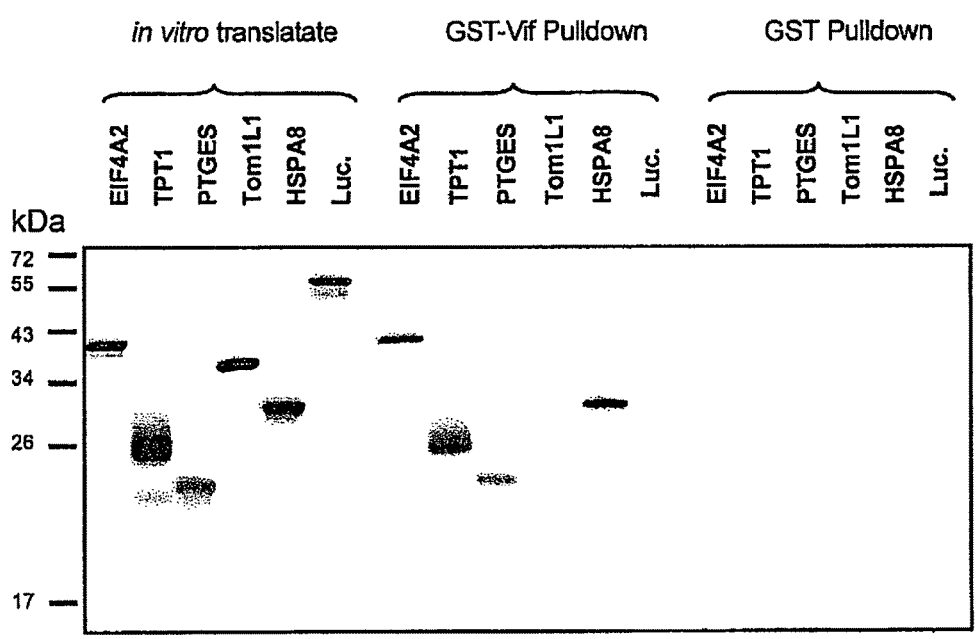

FIG. 3c: shows an autoradiography of a 12% sodium dodecyl sulphate (SDS) polyacrylamide gel representing the results of glutathione-S-transferase (GST) pull-down experiments. In particular, FIG. 3c shows the detection of interactions between GST-Vif and in vitro translated proteins.

Lane 1 to 6 represent radioactively labelled in vitro translated proteins, in particular, line 1 shows in vitro translated EIF4A2; line 2 shows in vitro translated TPT1; line 3 shows in vitro translated PTGES3, lane 4 shows in vitro translated TOM1L1; line 5 shows in vitro translated HSPA8; and line 6 shows in vitro translated luciferase (Luc.).

Lanes 7 to 12 represent the respective pull-down results of the afore-mentioned radioactively labelled in vitro translated proteins by GST-Vif glutathione sepharose beads.

In particular, lane 7 shows GST-Vif and in vitro translated EIF4A2; line 8 shows GST-Vif and in vitro translated TPT1; line 9 shows GST-Vif and in vitro translated PTGES3, line 10 shows GST-Vif and in vitro translated TOM1L1; line 11 shows GST-Vif and in vitro translated HSPA8; and line 12 shows GST-Vif and in vitro translated luciferase (Luc.; negative control).

Lanes 13 to 18 represent the control for the specificity of the GST pulldown experiment, i.e. for the binding specificity of the in vitro translated proteins to Vif. Therefore, lanes 13 to 18 in particular represent the results of GST pull-down, wherein GST was used alone, i.e. without being fused to Vif. More particularly, lane 13 shows GST and in vitro translated EIF4A2; line 14 shows GST and in vitro translated TPT1; line 15 shows GST and in vitro translated PTGES3, line 16 shows GST and in vitro translated TOM1L1; line 17 shows GST and in vitro translated HSPA8; and line 18 shows GST and in vitro translated luciferase (Luc.). It is demonstrated, that there is no unspecific binding of the in vitro translated proteins to GST alone.

Figure 4:
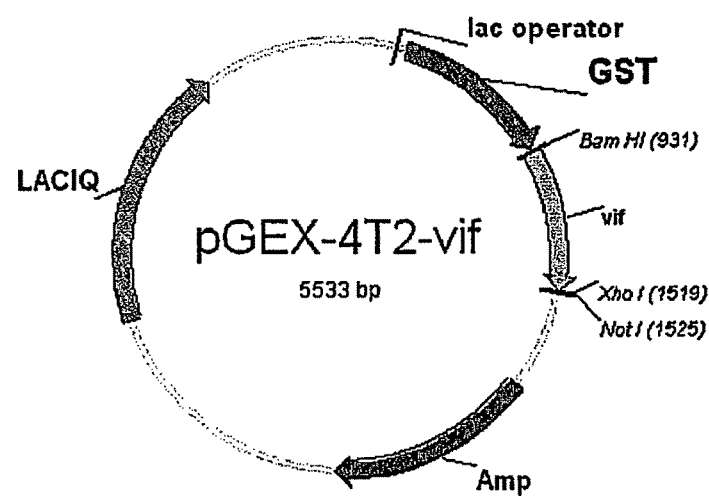

FIG. 4: schematically represents vector pGEX-4T2-vif, used for expression of Vif for use in GST pull-down experiments. The sites of lacIQ promoter, GST and vif are indicated.

Figure 5:
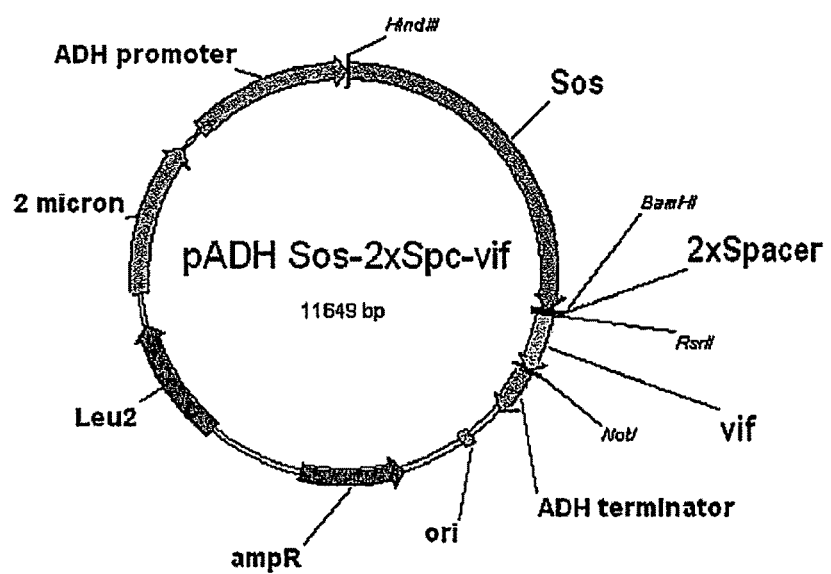

FIG. 5: schematically represents vector pADH Sos-2xSpc-vif, used for the expression of the first fusion protein for use in the method of the present invention. The sites of (constitutive) ADH promoter, Sos, spacer (linker) and vif are indicated.

Figure 6:
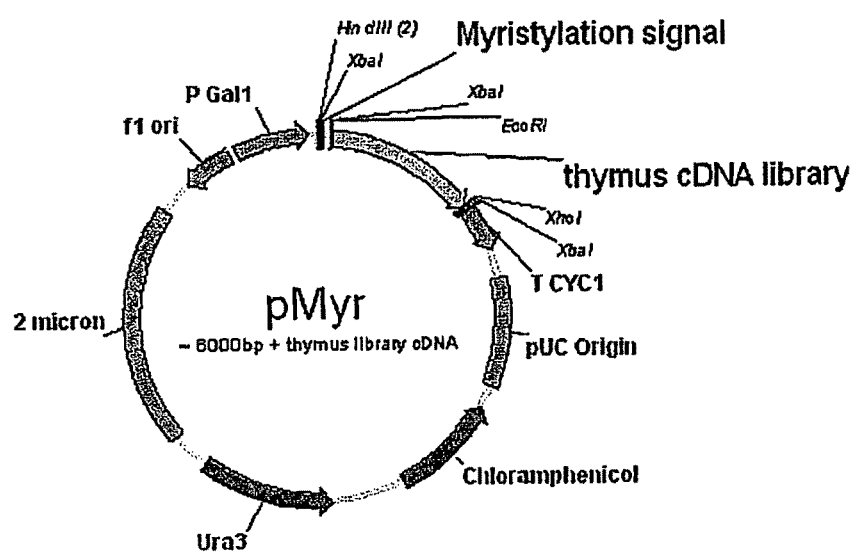

FIG. 6: schematically represents vector pMyr, used for the expression of the second fusion protein for use in the method of the present invention. The sites of the (inducible) GAL1 promoter, the myristoylation signal and the thymus cDNA library are indicated.

FIG. 7: FIG. 7 illustrates growth of yeast cells upon simultaneous expression of the two fusion proteins (the first fusion protein comprising Vif fused to Sos [via a linker] and the second fusion protein comprising a protein derived from the thymus library fused to a membrane localization domain). In particular, FIG. 7 shows the interaction of the two proteins upon which Sos is recruited to the cell membrane activating the Ras signalling pathway resulting in a detectable phenotype, i.e. allowing the growth of yeast cells even at the restrictive temperature of 37° C. Expression of the first fusion protein is under the control of the constitutive alcohol dehydrogenase promoter, however, since expression of the second fusion protein is under the control of a GAL1-promoter, cell growth at the restrictive temperature is only detected upon galactose addition (left side) whereas addition of glucose represses prey expression and detectable growth can not occur. Binding specificity of vif to host proteins is shown as the control protein cJun fused to Sos does not cause a signal. 5 different clones from single yeast strains carrying bait and prey expression plasmid were spotted onto selection plates containing either galactose or glucose as sugar and shifted to restrictive temperature.

DEFINITIONS

"cDNA", as the term is used herein, generally describes complementary DNA, i.e. a piece of DNA lacking internal, non-coding segments (introns) and transcriptional regulatory sequences. A cDNA may further contain untranslated regions (UTRs) that are responsible for translational control in the corresponding RNA molecule. cDNA can be produced using various methods, such as synthesis in the laboratory by reverse transcription from messenger RNA extracted from cells.

"Infection", as the term is used herein, generally relates to the entry, replication, insertion, lysis or other event or process involved with the pathogenesis of a virus into a host cell. Thus, decreasing infection includes decreasing entry, replication, insertion, lysis, or other pathogenesis of a virus into a cell or subject, or combinations thereof. Infection includes the introduction of an infectious agent, such as a non-recombinant virus, recombinant virus, plasmid, or other agent capable of infecting a host, such as the cell of a subject.

"Mimetic", as the term is used herein, generally refers to a molecule that mimics the activity of an agent. The term "mimetics" when used in the context of peptides, refers to molecular structures, which serve as substitutes for the peptides of the present invention in the interaction with HIV Vif. Peptide mimetics, as used herein, include synthetic structures which may or may not contain amino acids and/or peptide bonds, but retain the structural and functional features of a peptide ligand. The term "peptide mimetics" also includes peptides and oligopeptides, which are peptides or oligomers of N-substituted amino acids. Further included as peptide mimetics are peptide libraries, which are collections of peptides designed to be of a given amino acid length and representing all conceivable sequences of amino acids corresponding thereto.

"Operably linked", as the term is used herein, generally describes a first nucleic acid sequence as operably linked with a second nucleic acid sequence when the first nucleic acid sequence is placed in a functional relationship with the second one. For instance, a promoter is operably linked to a coding sequence if the promoter affects the transcription or expression of said coding sequence. Generally, operably linked DNA sequences are contiguous and, where necessary to join two proteins coding regions, in the same reading frame.

"Pharmaceutical agent or drug", as the terms are used herein, generally relate to a chemical compound or composition capable of inducing a desired therapeutic or prophylactic effect when administered to a subject, alone or in combination with one or more therapeutic agent(s) or pharmaceutically acceptable carriers.

"Preventing" a disease, as the term is used herein, generally refers to the inhibition of the full development of a disease, for example the prevention of development of a viral infection.

"Treatment", as the term is used herein, generally describes a therapeutic intervention that ameliorates a sign or symptom of a disease or pathological condition related to, for example, a HIV-1 infection, such as inhibiting or decreasing HIV-1 infection.

"First fusion protein", as the term is used herein, generally relates to a protein comprising an effector and a "target" protein such as an HIV protein. A target protein generally is a known protein that is being examined as to whether it can be involved in a protein-protein interaction. Preferably, the first protein of the present invention comprises a peptide linker molecule, arranged between the effector and the target protein.

"Second fusion protein", as the term is used herein, generally relates to a protein comprising a cell compartment localizing domain and a second protein such as a human protein, which can bind the target protein or is suspected of being able to bind to the target protein.

"Effector", as the term is used herein, generally describes a peptide or polypeptide that can be expressed as a fusion protein and, when so expressed, can activate a reporter molecule, provided the effector protein is translocated to the cell compartment containing the reporter molecule. However, also an active fragment of an effector such as a guanine exchange factor (GEF) can be used to practice the invention, provided the active fragment comprises a sufficient portion of the effector so as to confer the effector function. Such active fragments of an effector are considered to be within the meaning of the term "effector" as used herein.

"Lentivirus", as the term is used herein, refers to human immunodeficiency virus-1 (HIV-1); human immunodeficiency virus-2 (HIV-2); simian immunodeficiency virus (SIV); and feline immunodeficiency virus (Fly).

"Candidate protein", as the term is used herein, generally relates to the protein which is suspected for binding to the HIV target protein. The term "candidate protein" may be used interchangeably with the terms "host protein" and "human protein". According to the present invention, the term "candidate protein" does not only include full-length protein, but also comprises parts of the protein for example oligopeptides and peptides, respectively.

As used herein, a composition refers to any mixture. It can be a solution, a suspension, liquid, powder, a paste, aqueous, non-aqueous or any combination thereof.

The term "derivative" as applied to a protein or a peptide chain herein means a compound wherein one or more of the amino, hydroxyl, or carboxyl groups in a side chain of the peptide, or the terminal amino or carboxyl groups, is modified to a derivative functional group. An amino group may be derivatized as an amide (such as an alkylcarboxamide, acetamide), a carbamate (such as an alkyl carbamate, e.g. methyl carbamate or t-utylcarbamate), or a urea. A hydroxyl group may be derivatized as an ester (such as an alkanoate, e.g. acetate, propionate, or all arenecarboxylate, e.g. benzoate), a carbamate (such as an alkyl carbamate, e.g. methyl carbamate), a carbonate (such as an alkyl carbonate, e.g. ethyl carbonate. A carboxyl group may be derivatized as an ester (such as an alkyl ester, e.g. ethyl ester) or an amide (e.g. primary carboxamide, an N-alkyl secondary carboxamide, or an N,N-dialkylcarboxamide). The person skilled in the art will appreciate that derivatives of the peptide will be expected to result in retention of the properties of the parent peptide, either because the incorporation of the derivative group does not change the properties of the peptide, or the derivatizing group is removed in vivo (e.g. via metabolism). Preferred embodiments of the invention are those wherein three or fewer of the amino, carboxyl, and hydroxyl groups, and preferably two or fewer, or one or none, are modified to a derivative functional group. The term "derivative" also includes salts, includes salts of derivatives. Derivatives may include terminal derivatives.

The term "terminal derivative" used in reference to a peptide means a peptide where the C-terminal carboxylate group, or the N-terminal amino group, or both is modified to a derivative functional group. The C-terminal carboxyl group may be derivatized as an ester (such as an alkyl ester, e.g. ethyl ester) or an amide (e.g. primary carboxamide, an N-alkyl secondary carboxamide, or an N,N-dialkylcarboxamide). The N-terminal amino group may be derivatized as an ester (such as an alkyl ester, e.g. ethyl ester) or an amide (e.g. primary carboxamide, an N-alkyl secondary carboxamide, or an N,N-dialkylcarboxamide). The C-terminal carboxyl group and/or the N-terminal amino group may also be in the form of a salt.

DETAILED DESCRIPTION OF THE INVENTION

The present invention focuses on the identification of targets for drug discovery for use in the treatment and prevention of viral diseases such as AIDS.

As described in the background section, one strategy of further combating HIV infection potentially could be to target the virus' accessory proteins and their interaction with their host protein binding partners. However, this approach is hampered by the lack of knowledge of the complexity of the protein interaction network of those accessory proteins on the one hand, and on the other hand the human proteins known so far do not seem to be appropriate candidates for drug development in view of their normal function in the cell. Initial attempts to further pinpoint the specificity of the interaction of HIV accessory proteins with other viral or cellular factors failed. However, experiments performed in accordance with the present invention using a modified version of the Sos-recruitment system (SRS) essentially described in U.S. Pat. No. 5,776,689, which hitherto has not been considered in context with viral/human protein interaction, surprisingly revealed novel human host proteins as specific targets of one of the HIV accessory proteins, i.e. Vif. Thus, a new class of human cellular proteins being involved in HIV infection could be identified, thereby providing novel targets for drug development.

Because of the peculiarity and reliability of the Sos-recruitment system and the further developments performed during the development of the method of the present invention, it is prudent to stipulate that the host (preferably human) HIV Vif-binding proteins identified according to the method of the present invention indeed play a key role in the course of HIV infection, viral life cycle and AIDS, respectively. Accordingly, the present invention also concerns the use of the Sos-recruitment system for investigating the interaction of viral disease associated proteins and binding partners thereof, in particular to specifically approach the identification of proteins binding to HIV-related proteins such as Vif.

Thus, in one aspect, the present invention relates to a method for identifying and cloning of a nucleic acid molecule encoding a protein or fragment thereof capable of interacting with a human immunodeficiency virus (HIV)-protein, the method comprising:

(a) expressing in a host cell a first nucleic acid molecule encoding a first fusion protein comprising an effector protein, which is not a transcription factor, fused to a target HIV protein;

(b) further expressing in said cell a second nucleic acid molecule encoding a second fusion protein comprising a cell membrane localization domain fused to a human protein or fragment thereof; and (c) detecting activation of a reporter molecule by detecting a signal that identifies an interaction between the target HIV protein of (a) and the human protein of (b); and optionally (d) cloning the nucleic acid molecule encoding the human protein or fragment thereof for which activation of the reporter molecule is detected in step (c).

Although the method of the present invention is useful for investigating a broad variety of different factors, enzymes or proteins associated with HIV, however, in a preferred embodiment, the target HIV protein used in the method of the present invention is an accessory HIV protein, preferably the viral Infectivity factor (Vif).

During initial optimization experiments performed in accordance with the present invention and required for establishing an efficient method, it surprisingly turned out that identification of proteins interacting with Vif ("candidate proteins" and "host proteins", respectively) was considerably improved in the presence of an additional peptide linker molecule. The use of the linker, having the sequence Gly-Gly-Gly-Gly-Ser-Gly-Gly-Gly-Gly-Ser (SEQ ID No: 3) and a description of which or similar can be found in for example Evers et al. Biochemistry 45 (2006), 13183 and Maeda at al., BioTechniques 20 (1996), 116, when arranged between the effector molecule and the candidate protein, resulted in the possibility of identifying human proteins being a target of Vif, which hitherto have not been identified using conventional methods. Accordingly, in a further embodiment, the method of the present invention further comprises expressing in a host cell a first nucleic acid molecule encoding a first fusion protein comprising an effector fused to a target HIV protein by a peptide linker.

The present invention employs proteins and populations of proteins being encoded by a nucleic acid library, for example a cDNA or EST library, an example of which is described in detail in the examples. Therefore, the human protein used in the method of the present invention is encoded by cDNA, preferably, wherein the cDNA is provided within a pool of cDNAs, more preferably within a cDNA library. Although several libraries can be used in accordance with the method of present invention, such as T cell libraries, human B-lymphoblastoid cDNA libraries, lymph node-derived cDNA libraries or HeLa cell libraries, most preferably, the cDNA library used in the method of the present invention is a thymus library.

One major advantage of the method of the present invention is that it can be applied to almost any type of cell, such as mammalian, avian, insect, yeast and *E. coli* cells. However, in a preferred embodiment, the host cell used in the method according to the present invention is a yeast cell.

In accordance with the method of the present invention, the protein-protein interaction is indicated by the occurrence or absence of cell growth. Therefore, it is necessary to use cells, the phenotype (cell growth) of which changes upon protein-protein interaction. There are cell lines known in the art revealing a respective phenotype, for example, due to the lack of an endogenously expressed effector which is necessary for activating the Ras signalling pathway, which finally induces cell growth. One such cell line, for example, is a yeast cell line mutated in the cdc25 gene (cdc25-2). Cdc25 is a guanine exchange factor (GEF) that when localized at the plasma membrane, leads to the activation of Ras; see Petitjean et al., Genetics 124 (1990), 797-806. Accordingly, mutations in Cdc25-2 lead to lack of an expressed functional Ras effector, resulting in a growth defect at the restrictive temperature, i.e. 37° C. This defect can be overcome by providing or "recruiting" a respective Ras effector to/at the cell membrane. In this context, since the fusion proteins according to the present invention are designed in that one fusion protein comprises a cell membrane localization domain and the other fusion protein comprises an effector molecule, capable of activating the Ras signalling pathway, upon protein-protein interaction the Ras effector is recruited to the cell membrane thereby activating the Ras signalling pathway and enabling the cells to grow. Thus, since the use of said cells renders the method very easy to determine protein-protein interaction by optically observing the presence or absence of cell growth, in a particularly preferred embodiment of the method of the present invention, the yeast cells are *Saccharomyces cerevisiae* cdc25-2 cells.

As mentioned supra, during experiments of the present invention, growth of the cells in which the assay is performed is indicative for the protein-protein interaction. However, as already described, this requires that one fusion protein comprises the cell membrane localization domain and that the other fusion protein comprises an effector molecule. Although there are several molecules known in the art, capable of effecting a respective Ras-activation, in a preferred embodiment of the method of the present invention this effector molecule is the Son of sevenless (Sos)-protein.

Naturally, the present invention also relates to the nucleic molecule obtainable by the invented method, preferably wherein the nucleic acid molecule encodes a protein capable of interacting with Vif. However, the determination of the sequence of the encoded proteins, surprisingly revealed the nucleic acid molecules identified by the method of the present invention to encode a new class of Vif-binding proteins, comprising the motive: [DLN][^AF][DLN][^P][^P][^P][^P][DLN], which, as will be recognized by the person skilled in the art, is represented using the generally accepted one-letter code of the amino acids. However, a brief explanation of the symbols and letters, respectively, is given in the following:

"[DLN]" means that the amino acid at this position is either D, L or N (aspartic acid, leucine or asparagine).

"[^AF]" means that any amino acid could be at this position except for A, F (alanine, phenylalanine).

"[^P]" means that any amino acid could be at this position except for P (proline).

Thus, in a further embodiment the present invention refers to the nucleic molecule obtainable by the invented method, most preferably, wherein the encoded protein comprises the motive: [DLN][^AF][^P][^P][^P][^P][DLN].

In general, the first and second nucleic acid molecule, encoding the first and second fusion protein, respectively, used in the method of the present invention, is present in an expression vector suitable for the particular cells in which the interaction of the fusion proteins is to occur. Examples of appropriate expression vectors comprise, for example, yeast expression vectors or mammalian expression vectors, depending on the cells in which the method is to be performed. In particular, vectors according to the present invention contain a cloning site such as a multiple cloning site, which permits a convenient means to insert a nucleic acid molecule encoding a target protein. In accordance with the present invention, promoter and nucleic acid molecules are arranged in so called "expression cassettes", wherein the expression cassette of the first fusion protein comprises a promoter operably linked to a nucleic acid encoding the target protein (Vif or a homolog, derivative or fragment thereof) in frame with the effector protein, and the other expression cassette comprises a promoter operable linked to a nucleic acid encoding the candidate (host) protein (or a homologue, derivative or fragment thereof) in frame with the linker and cell compartment localization signal. In addition, the vectors can contain appropriate transcription or translation start or stop signals or the like. Preferably, the expression cassettes are chimeric expression cassettes including heterologous promoters.

Thus, in another embodiment the present invention relates to a vector comprising the above-described nucleic acid molecule, preferably, wherein the vector further comprises a nucleic acid molecule encoding the target HIV protein as defined above or a binding fragment thereof.

The present invention of course also relates to a recombinant host cell comprising the nucleic acid molecule obtainable by the method of the present invention or the above-described vector.

In a further embodiment, the present invention provides a method of preparing a protein, capable of interacting with an HIV protein or a complex comprising an HIV protein and a human protein comprising the steps of:

(a) cultivating the above characterized host cell and/or expressing the nucleic acid molecule obtainable by the method of the present invention or the vector according to the present invention in vitro; and (b) isolating the protein or the complex.

To date, several proteins have been identified to interact with proteins involved in the HIV replication cycle. However, using the method of the present invention, host (human) proteins were identified which hitherto have not been determined to bind to Vif. Further analysis revealed the proteins to belong to a new class of proteins, the members of which share the capability to bind to Vif and the above-referenced motif.

Hence, in yet another embodiment, the present invention is directed to an HIV-interacting protein encoded by a nucleic acid molecule or obtainable by the above mentioned method of the present invention, preferably wherein the protein is selected from the group consisting of: PTEN (SEQ ID NOs: 4 and 5), HERC4 (SEQ ID NOs: 6 and 7), Tom1L1 (SEQ ID NO: 8), EIF4A2 (SEQ ID NO: 9), TCTP (TPT1: SEQ ID NOs: 10, 11, 12 and 13), NUP50 (SEQ ID NO: 14), CTCF (SEQ ID NO: 15), hnRPU (SEQ ID NO: 16), MRCL (MRCL3: SEQ ID NO: 17), SDCCAG1 (SEQ ID NOs: 18 and 19), PTGES3 (SEQ ID NO: 20), HSPs (HSP90: SEQ ID NO: 21; HSPA1: SEQ ID NOs: 22, 23, 24, 25, 26, 27 and 28; HSPA5: SEQ ID NOs: 29, 30 and 31; HSPA8: SEQ ID NOs: 32, 33 and 34; HSPH1: SEQ ID NO: 35) and CSDE1 (SEQ ID NO: 36), KIA1429 (SEQ ID NO: 42), CUL4A (SEQ ID NO: 43), RAG2 (SEQ ID NO: 44), CCT5 (SEQ ID NO: 45), VCP (SEQ ID NO: 46), PDIA3 (SEQ ID NO: 47), PTPRC (SEQ ID NO: 48), CAB39 (SEQ ID NO: 49) PPM1B (SEQ ID NO: 50), RAB4A (SEQ ID NO: 51) RAB21 (SEQ ID NO: 52) or fragments or derivatives of any one thereof.

Although the function of Vif appears to be intimately connected with the activity of host cell factors, the molecular mechanism of Vif is still unknown. Without intending to be bound by theory, it is believed that Vif "mediates" the contact between the viral species and the host, i.e. acts as an "adapter" connecting viral factors to cellular factors and/or pathways of the host. This enables the virus which is strongly dependent on the accessibility to the host's cell machinery due to the retroviral nature of HIV as well as its small size to pass its replication program. Thus, the prevention of and interference with the interaction of Vif and host, refuses the access to the host's cell machinery and is believed to be a therapeutic approach to prevent HIV replication and therefore the onset or progression of AIDS.

Thus, Vif is believed to be an important target to be addressed when thinking of new therapeutic approaches, which renders it necessary to identify host factors interacting with Vif and to evaluate their possible impact on HIV replication. Although several methods for investigating protein-protein interactions are described in the art, the development of methods for identifying interacting partners of viral proteins and detecting the interaction of a viral protein with a host protein, respectively, under physiological conditions is of major interest.

In the following a short overview is provided of the "usual" functions, the proteins identified as Vif-binding proteins according to the method of the present invention hold in a healthy organism. The following further demonstrates that none of the detected proteins was previously determined or even suggested to be a target of Vif.

Phosphatase and tensin homolog (PTEN) (synonyms BZS, MHAM, TEP1, MMAC1, PTEN1, MGC1127), Accession Number. NM_000314. This enzyme catalyses the dephosphorylation of the second messenger molecule phosphatidylinositol 3,4,5-trisphosphate (PI-3,4,5-$P_3$) that is generated by the action of phosphatidyl inositol 3-kinase (PI3K), which itself is activated in response to T cell receptor and B cell receptor engagement. Among others, PI3K is also activated by signalling induced by the insulin-like growth factor IGF-1 (Yamamoto et al., Endocrinology 130 (1992), 1490-98) and insulin (Hadari et al., J. Biol. Chem. 267 (1992), 17483-17486), and activates itself downstream the serine-threonine kinase PKB/Akt pathway which is mainly involved in anti-apoptosis, proliferation and oncogenesis. PTEN is a negative regulator of the PI3K signalling pathway, in the absence of which, hyperactivation of the PKB/Akt pathway results in an increased resistance to apoptosis, enhanced cell survival, and proliferation. Investigation of mice with a T cell-specific deletion of PTEN indicated its important regulatory function for proliferation of developing T cells in thymus; see Hagenbeek et al., J. Exp. Med. 200 (2004), 883-894.

Although regulation of T cell apoptosis during HIV infection is important during phases of clinical latency and further disease progression, however, molecular mechanisms of induction of T cell death by HIV as well as protection of HIV-infected T cells are not well defined. In case of HIV infection, viral infection-induced apoptosis contributes to the depletion of CD4+ T cells and progression of HIV infection and AIDS, which is associated with immunodeficiency. Thus, inhibition of apoptosis of CD4+ T cells may be a strategy in preventing or treating HIV infection.

Different HIV proteins have been described to play a role in regulation of cell death; see Selliah and Finkel, Cell death and differentiation 8 (2001), 127-136. For instance, apoptosis of uninfected bystander T cells may be induced by HIV-Tat and HIV-Vpr. Furthermore, the binding of the envelope glycoprotein HIV-Env to the cellular receptors CD4 and CXCR4 has also been shown to induce apoptosis in primary T lymphocytes; see Cicala et al., PNAS 97 (2000), 1178-1183. On the other hand, an interaction of PI3K with the viral protein Nef was demonstrated to lead to anti-apoptotic signalling because of PI3K activation; see Wolf et al., Nature Med. 7 (2001), 1217-1224. Down-regulation of PTEN by intracellular Tat and HIV-1 infection has been suggested as potential mechanism for stimulation of the PI3K/Akt survival pathway; see Chugh et al., J. Mol. Biol. 366 (2007), 67-81. In this context, protein complexes comprising HIV Gag and PI3K and the use of these protein complexes have already been described in international application WO 02/090549.

Furthermore, international application WO 03/060067 describes compositions and methods for inhibiting viral infections and viral maturation by administering effective amounts of a PI3K pathway inhibitor, as well as protein complexes of a regulatory subunit of PI3K and Herc ubiquitin ligases and Nef.

PI(4,5)$P_2$, the product of the PTEN catalyzed reaction, was also shown to be involved in regulation of Gag localization and virus assembly; see Ono et al., PNAS 101 (2004), 14889-14894. Furthermore, virus production was shown to be strongly inhibited by reduced levels of plasma membrane PI(4,5)$P_2$, an effect which is due to inhibition of Gag localization to the plasma membrane. In addition, structural studies of the complex of the matrix domain of Gag and PI(4,5)$P_2$ have been performed by Saad et al., PNAS 103 (2006), 11364-11369. However, complexes of PTEN and HIV Vif have not been described before.

In this context, the identification of PTEN (SEQ ID NOs: 4 and 5, respectively) in accordance with the method of the present invention as a direct interaction partner and target, respectively, of Vif, provides options for new strategies for the treatment and prevention of HIV infection and AIDS, respectively, such as preventing the respective interaction by supplying PTEN or mimetics thereof, or applying compounds, capable to modify expression of PTEN or affect the complex of PTEN and Vif. As a consequence, the viral access to the host's cell machinery would be prohibited and viral replication stopped. Furthermore, the host's regulation of apoptosis would be maintained and redirected to the host, respectively, as it would be the case in the absence of HIV.

HERC E3 ubiquitin ligase, Accession Numbers HERC4: NM_001017972, NM-015601, NM_022079. E3 ubiquitin ligases containing RCC1 (regulator of chromosome condensation 1)-like domains (RLD) in addition to a HECT domain are denominated as HERC. RCC1 is a GEF (guanine nucleotide exchange factor) for Ran and participates in nucleocytoplasmic transport and mitotic spindle formation. Therefore, a role as both GEF and ubiquitin ligase is assumed for HERC proteins, a protein family which is consisting of 6 different HERC proteins (2 large, 4 small).

The interaction of HIV Vif with a cullin-based E3 ligase has been already shown by Yu at al., Science 302 (2003), 1056-1060; Mehle et al., Genes and Dev. 18 (2004), 2861-2866, Mehle et al., J. Biol. Chem. 281 (2006), 17259-17265. Furthermore, this protein interaction was described as essential for deactivation of the cytidine deaminase APOBEC3G by Shirakawa at al., Virology 344 (2006), 263-266, Kobayashi et al., J. Biol. Chem. 280 (2005), 18573-18578. In addition, it was shown that the HIV protein Vif is rapidly degraded intracellularly and it was suggested that the rapid turn-over of Vif is biologically important to prevent detrimental effects of this protein at high expression levels; see Fujita at al., Microbes and Infection 6 (2004), 791-798. Large amounts of polyubiquitinated derivatives of Vif were detected in cells. Furthermore, ubiquitination of HIV Vif was investigated by Dussart at al., 2004 and interaction with proteins of the HECT E3 ubiquitin ligase family was reported, as well as complexes of Vif with hNedd4-1 and AIP4 were described. However, protein complexes of HIV Vif and HERC E3 ubiquitin ligases discovered by the method of the present invention have not been described before.

Furthermore, international application WO 02/090549 describes the interaction of HERC proteins with HIV Gag to play a role in viral maturation, and international application WO03/060067 describes protein complexes of HERC ubiquitin ligases and a regulatory subunit of PI3K containing a Nef protein.

Hence, the identification of HERC E3 (SEQ ID NOs: 6 and 7, respectively) in accordance with the method of the present invention as a Vif-binding protein, renders it a suitable target when considering novel strategies in the field of HIV infection and AIDS. As already mentioned in connection with PTEN, this may comprise the supply of HERC E3 or mimetics thereof, or compounds, capable to modify either the expression of HERC E3 or the formation of the complex of HERC E3 and Vif in order to stop viral replication.

target of myb1-like 1 (TOM1L1) Accession Number: NM_005486, and the related proteins Tom1 and Tom1L2 constitute a protein family which is characterized by a VHS-domain (Vsp27p, Hrs and Stam) in the N-terminal region and a GAT homology domain (GGA and Tom) involved in vesicular trafficking; see Bonifacino, J S, Nat. Rev. Mol. Cell. Biol. 5 (2004), 23-32; Lohi et al., FEBS Lett 513 (2002), 19-23. Franco et al., Mol. Cell. Biol. 26 (2006), 1932-1947, identified TOM1L1 as negative regulator of Src mitogenic signalling by modulating SFK (src kinase family)/receptor association. Furthermore, Vif was shown to interact with the Src tyrosine kinases Fyn and Hck resulting in a reduction of their catalytic activities by Hassaine et al., J. Biol. Chem. 276 (2001), 16885-16893; Douaisi et al., Biochem. Biophys. Research Comm. (2005).

Interactions of TOM1L1 with the multivesicular body sorting machinery have been shown by Puertollano et al., J. Biol. Chem. 280 (2005) 9258-9264. More specifically, protein interaction with TSG101 was demonstrated, this protein being a factor involved in endosomal protein sorting. Interestingly, HIV-1 Gag interaction with Tsg101 is important for efficient virus budding; see Martin-Serrano et al., Nat Med 7 (2001) 1313; international applications WO 02/090549 and WO 02/072790. Additionally, anti-TSG101 antibodies and TSG 101 derived peptides have been described for the treatment of viral infections; see international applications WO 04/031209 and WO 02/094314.

Thus, the identification of the molecular interaction between TOM1L1 (SEQ ID NO: 8) and Vif according to the method of the present invention renders TOM1L1 or the complex between TOM1L1 and Vif a suitable target in the field of HIV and AIDS treatment and prevention, respectively. In particular, since it is known that the viral protein Vif is expressed lately in the viral life cycle and Vif was discussed to be involved in the viral assembly process; see Zhang et al., J. Virology 74 (2000), 8252-8261, without intending to be bound by theory, the molecular interaction of Vif with Tom proteins is believed to be a key component for Vif modulation of cellular host factors, because of Tom1L1 being thought to connect signalling and degradative cellular pathways and hence to play an important role in the virus' replication. Therefore, prevention of the respective formation of TOM1L1/Vif complex is believed to stop viral replication and to maintain and redirect, respectively, the protein sorting and degradation mechanisms to the host.

*homo sapiens* eukaryotic translation initiation factor 4A (eIF4A), Accession Number: NM_001967, a component of eIF4F complex, is a DEAD-box helicase ('DEAD-box' disclosed as SEQ ID NO: 53) which functions in the ribosome recruitment step of translation initiation. The eIF4F-complex also comprises eIF4E, which binds the mRNA cap structure in an ATP-independent fashion and eIF4G, a modular scaffold that mediates mRNA binding of the 43S pre-initiation complex. eIF4A plays an important role in facilitating the translation by unwinding the secondary structure of the 5' region of mRNA. eIF4A can be involved in mRNA-ribosome binding both in its free form and as part of the eIF4F complex.

During viral infection of host cells the viral mRNAs have to compete with host mRNAs for the limited pool of eukaryotic translation initiation factors that mediate the recruitment of ribosomes to both viral and cellular mRNAs. Therefore, viruses modify certain eIFs within infected cells for replication of the viral genome. Although interactions of eIF4A with the virion host shutoff (vhs) protein of herpes simplex virus (Feng et al., J. Virology, 79 (2005), 9651) and with the NS5B protein of HCV (Kyono et al., Biochem. Biophys. Research Comm. 292 (2002), 659) have already been demonstrated, however, the present invention provides the detection of complexes of eIF4A with proteins of HIV, i.e. HIV Vif.

Therefore, the new finding of eIF4A (SEQ ID NO: 9) according to the method of the present invention as being also a direct target of Vif provides a useful potential target for developing new anti-HIV/AIDS therapeutic approaches. For example, affecting either eIF4A or the complex of eIF4A and Vif is believed to prevent competition between the virus and host for the binding to host translation initiation factors such as eIF4A, thereby not only hampering viral replication but also maintaining the natural but, however, limited pool of initiation factors being at the host's disposal.

Tumor protein, translationaliy controlled (TCTP) (Synonyms: fortilin, histamine-releasing factor, HRF, TPT1, p02), Accession Number: NM_003295 is not a tumour- or tissue-specific protein, but is expressed ubiquitously in all eukaryotic organisms and in more than 500 tissue and cell types; see Bommer and Thiele, J. Biochem. Cell Biol. 36 (2004): 379-385; Sanchez et al., Electrophoresis 18 (1997), 150-155. TCPT levels are highly regulated in response to a wide spectrum of extracellular stimuli like stress conditions; see Bommer et al., RNA 8 (2002), 478-496; Bonnet et al., Yeast 16 (2000), 23-33. TCTP was also shown to have an extracellular function as a histamine release factor and to have anti-apoptotic activity; see Li et al., J. Biol. Chem. 276 (2001), 47542-47549.

TCTP also known as fortilin binds MCL1, a protein of the anti-apoptotic Bcl-2 family, suggesting that fortilin might be an MCL1-specific cofactor in the regulation of apoptosis; see Zhang et al., J. Biol. Chem. 277 (2002), 37430. Methods for modulating fortilin activity and interactions with MTL-1 and p53 have been described in international application WO02/36624, and the anti-apoptotic gene MTL-1 was shown to be significantly upregulated in response to a successful antiretroviral therapy of HIV patients by Balestrieri et al., J. Med. Virol. 79 (2007), 111-117.

In addition, TCTP specifically interacts with the apoptosis regulator Bcl-XL; see Yang et al., Oncogene 24 (2005), 4778-4788. Bcl-XL is also a Bcl-2-related protein that functions as a regulator of apoptosis and is found localized in the mitochondria membrane, where it binds and close the mitochondrial voltage-dependent anion channel, thus preventing the transport of cytochrome c, the capase activator from the mitochondrial lumen to the cytoplasm; see Shimizu et al., Nature 399 (1999), 483-487. Screening assays for modulators of the Bcl-XL/TCTP protein complexes, identification of modulating compounds, and therapeutic applications for the treatment of apoptosis-related diseases including HIV have been described in US 2002/0177692. Furthermore, TCTP was described as HIV-inhibiting protein in international application WO 01/16322. However, protein complexes containing HIV Vif and TCTP have not been described before.

According to the advantages discussed already in the context with the above-referenced proteins identified as Vif-binding proteins, also the identification of TCTP (TPT1: SEQ ID NOs: 10, 11, 12 and 13, respectively) as a direct target of Vif, is believed to provide a further suitable target, i.e. TCTP or the respective complex with Vif, for the development of novel strategies in the field of HIV/AIDS. In particular, prevention of the respective interactions of Vif and TCTP is believed to prevent viral access to the host's cell machinery and thereby viral replication. Furthermore, the regulation of apoptosis should be no longer influenced by HIV, but rather controlled by the host as would be the case in an uninfected organism.

Nucleoporin (NUP50) (Synonyms NPAP60, NPAP60L, MGC39961, DKFZ564A043), Accession Numbers: NM_007172, NM_153645.

In order to complete its life cycle, human immunodeficiency virus requires the introduction of its genome into nuclei of host non-dividing cells. After infection of the host cell, the HIV capsid is rapidly uncoated, and the genomic HIV RNA is reversely transcribed into linear dsDNA, which remains associated with a nucleoprotein complex that is called pre-integration complex (PIC). The viral genome is complexed by viral proteins containing nuclear localization signals (NLS), and three HIV proteins are known to be involved as karyophilic proteins in the nuclear import of the PIC by recruiting the cellular nuclear import machinery: the HIV-1 matrix protein, the auxiliary protein Vpr and the HIV integrase; for review see Bukrinsky, Mol. Med. 10 (2004), 1-5. In addition, the viral protein Rev carries a short C-terminal leucine-rich motive as nuclear export signal important for its nucleocytoplasmic shuttling and the Rev-dependent transport of viral mRNA.

Investigation on sub-cellular localization of Vif revealed that it is a predominantly cytoplasmic protein; see Goncalves et al., J. Virol. 68 (1994), 704-712; Goncalves et al., J. Virol. 69 (1995), 7196-7204; Michaels et al., AIDS Res. Hum. Retroviruses 9 (1993), 1025-1030. Nevertheless, nuclear localization of Vif has also been observed; see Wichroski et al., J. Biol. Chem. 280 (2005), 8387-8396. The Vif sequence contains a basic region $^{90}$RKKR$^{93}$ (SEQ ID NO: 54) which is similar to the prototypic nuclear localization signal and this motive was identified as potential nuclear transport inhibitory signal. It has been postulated that Vif may function as a regulator of the nucleocytoplasmic transport; see Friedler et al., J. Mol. Biol. 289 (1999), 431-437. Furthermore, backbone cyclic peptide analogues of NLS-like sequence of Vif have been described as candidates for drugs based on the inhibition of nuclear import of viral genomes in international application WO 99/28338.

Nucleoporin NUP50 was shown to function in coordination of import complex disassembly and importin recycling; see Matsuura et al., EMBO J. 24 (2005), 3681-3698. Because of its localization NUP50 is suggested to function within the nucleoplasmic part of NPCs and probably mainly at the nuclear basket; see Guan et al., Mol. Cell. Biol. 20 (2000), 5619-5630. Other nucleoporins NUP62 and NUP133 have been identified as enhancers of HIV infection by a cDNA screening; see Nguyen et al., Virology 362 (2007), 16-25.

Thus, the identification of NUP50 (SEQ ID NO: 14) as a direct target of Vif renders NUP50 and/or the complex between NUP50 and Vif a suitable target when thinking of novel therapeutic approaches for treatment of HIV infection and/or AIDS. Besides the fact that in case of preventing complex formation, viral replication is believed to be hampered or stopped, additionally, without intending to be bound by theory, since the molecular interaction between HIV Vif and NUP50 is believed to modulate the host's nucleocytoplasmic transport machinery, upon the prevention or disruption of the respective Vif/NUP50 interaction, the control of the nucleocytoplasmic transport in the cell should be directed back to the host as it would be in the absence of HIV infection.

CCCTC-binding factor (CTCF), Accession Number. NM_006565.

The transcriptional repressor CTCF is an ubiquitous protein involved in multiple tasks leading to gene silencing. CTCF is a 11-zinc finger transcription factor that plays a role in different aspects of gene regulation including promoter activation or repression, hormone-responsive gene silencing, methylation-dependent chromatin insulation, and genomic imprinting; see Dunn and Davie, Biochem. Cell Biol. 81 (2003), 161-167; Dunn et al., Exp. Cell Res. 288 (2003), 218-223. Interestingly, the specific up-regulation of the transcription repressor CTCF was linked directly to cellular resistance to HIV-1 of a HIV-1 resistance factors secreting T cell clone; see Kartvelishvili et al., Immunology Letters 93 (2004) 79-86. However, protein complexes containing HIV Vif and CTCF have not been described before.

Thus, also the identification of CTCF (SEQ ID NO: 15) as a protein interacting with Vif provides a further target to be addressed, when thinking of developing novel therapeutic approaches in the field of HIV infection and AIDS, respectively. In particular, without intending to be bound by theory, since it is believed that the interaction of Vif and the transcription factor CTCF is important for HIV replication in human host cells, its respective prevention should obstruct viral access to the host's cell machinery and thus stop viral replication.

HNRPU (Synonyms hnRNPU, Scaffold attachment factor A, SAF-A, p120, pp 120), Accession Numbers: NM_004501, NM_031844.

The protein belongs to the subfamily of ubiquitously expressed heterogeneous nuclear ribonucleoproteins (hnRNPs). hnRNPs are RNA binding proteins, having distinct nucleic acid binding properties and forming complexes with heterogeneous nuclear RNA (hnRNA). These proteins are associated with pre-mRNAs in the nucleus and appear to influence pre-mRNA processing and other aspects of mRNA metabolism and transport. While all of the hnRNPs are present in the nucleus, some seem to shuttle between the nucleus and the cytoplasm.

The protein hnRNPU is described to contain an RNA binding domain and scaffold-associated region (SAR)-specific bipartite DNA-binding domain and is further thought to be involved in the packaging of hnRNA into large ribonucleoprotein complexes. During apoptosis, this protein is cleaved in a caspase-dependent way, wherein cleavage occurs at the SALD site, resulting in a loss of DNA-binding activity and a concomitant detachment of this protein from nuclear structural sites. However, this cleavage does not affect the function of the encoded protein in RNA metabolism.

Selection from a human cDNA library for clones inducing resistance to infection with recombinant HIV-1 genomes resulted in the identification of a gene fragment with HIV-restricting activity. The active cDNA encodes an N-terminal fragment of hnRNPU. The gene fragment targets the 3'LTR in the viral mRNA blocking the cytoplasmic accumulation of HIV mRNA; see Valente and Goff, Mol Cell 23 (2006), 597-605. Different heterogeneous nuclear ribonucleoproteins have been identified as enhancers of HIV infection by a cDNA screening; see Nguyen et al., Virology 362 (2007), 16-25.

Hence, the identification by the present invention of HNRPU (SEQ ID NO: 16) as a Vif-binding protein generally provides the same advantages and options, respectively, concerning viral replication as discussed for the afore-mentioned proteins, i.e. upon prevention of the respective interaction of Vif and HNRPU, viral access to the host cell should be blocked and therefore HIV replication should be hampered or prevented and stopped, respectively. Furthermore, without intending to be bound by theory, HNRPU's "usual" involvement in complex formation with host's RNA and RNA metabolism and transport, respectively, upon prevention of the interaction between Vif and HNRPU, should be at the host's disposal only and not at risk to be abused by HIV.

Myosin regulatory light chain MRCL (Synonyms MLCB, MRLC3), Accession Number: NM_006471

Interactions of HIV proteins with host cell cytoskeletal components are of major importance for efficient virus replication. Specific functions of actin and microtubules for virus entry, intracellular trafficking, budding and virus release have been experimentally demonstrated. In addition, modulation of cytoskeleton is also thought to be important for HIV-induced apoptosis. The viral proteins Tat, Rev, Vpr and Nef have been identified as determinants for cytoskeletal remodelling; see Fackler and Kräusslich, Curr. Opinion Microbiol. 9 (2006), 409-415; Matarrese and Malorni, Cell Death Differ. 12 (2005), 932-941.

Furthermore, cytoskeletal association of the HIV accessory protein Vif was demonstrated and confirmation by confocal microscopy revealed a close co-localization with the intermediate filaments vimentin and keratin; see Karczewski and Strebel, J. Viral. 70 (1996), 494-507. Cytoskeletal Vif was found to be more stable to proteasome degradation than soluble cytosolic Vif; see Fujita et al., Microbes and Infection 6 (2004), 791-798. Induction of vimentin and plectin aggregation by Vif was observed in different cells; see Henzler et al., J. Gen. Virology 82 (2001), 561-573.

Additionally, myosin II has been shown to play an important role in the release of HIV-1 virions from infected cells, and chemical inhibitors of myosin light chain kinase have been shown by Sasaki et al., PNAS 92 (1995), 2026-2030, to block the release of HIV-1. Inhibition of MLC phosphorylation was observed and was correlated with direct interaction of MLC with Vpr by Zhao et al.: http://medschool.slu.edu/imv/index. phtml?page=zhao&cat=directory. However, protein complexes containing HIV Vif and MRCL have not been described yet.

Accordingly, the identification of MRCL (MRCL3: SEQ ID NO: 17) as a direct target of Vif renders it and the respective complex with Vif a suitable target for therapeutic approaches intended to stop the virus from passing its life cycle by using host's proteins, enzymes and factors, respectively. In particular, since the interaction of Vif with the cytoskeletal component MRCL may allow viral modification of the host's cytoskeleton, preventing the complex formation between MRCL and Vif should maintain and re-direct, respectively, the organisation of the skeletal structure under the host's control as it would be in the absence of an HIV infection.

Serologically defined colon cancer antigen 1 (SDCCAG1) (Synonyms NY-CO-1, FLJ10051), Accession Number: NM_004713 was identified as a tumor suppressor protein. Cell cycle arrest was caused in cancer cell lines by inducing SDCCAG1; see Carbonnelle at al., Int. J. Cancer 92 (2001), 388-397. In addition, it was shown by Bi et al., Oncogene 24 (2005), 8229-8239, that SDCCAG1 is a mediator of nuclear export. However, disease relevant functions for HIV pathogenesis have not been reported.

In this context, the identification of SDCCAG1 (SEQ ID NOs: 18 and 19, respectively) as a direct interaction partner of Vif, allows its targeting or the targeting of the respective complex with Vif for preventing or destroying the respective interaction in order to interrupt viral access to the host's cell machinery. Furthermore, without intending to be bound by theory, SDCCAG1's "usual" involvement in tumor suppression and nuclear export, respectively, should be at the host's disposal only and not at risk to be abused by HIV. Thus, determining SDCAG1 as Vif-binding protein provides a further option for new anti-HIV and anti-AIDS strategies, respectively.

Prostaglandin E Synthase 3 (PTGES3) (Synonyms P23, TEBP), Accession Number. NM_006601.

Prostaglandin $E_2$ ($PGE_2$) is an effective cAMP-elevating lipid mediator, endowed with several immunoregulatory effects. Serum levels of $PGE_2$ have been shown to be significantly increased during HIV infection; see Delemarre of al., AIDS 9 (1995), 441-445; Foley et al., Immunol. 75 (1992), 391-397. In a cellular study $PGE_2$ was demonstrated to enhance HIV replication; see Kuno et al., PNAS 83 (1986), 3487-3490; Lima et al., IAS Conf HIV Pathog. Treat 2005: abstract No. WePe8.6B04 (2005). In this context, $PEG_2$-induced expression of functional inhibitory CD94/NKG2A receptors in human CD8+ T lymphocytes has been observed by Zeddou at al., Biochemical Pharmacology 70 (2005), 714-724. Furthermore, $PGE_2$ production was shown to be stimulated by peptides deriving from a conserved sequence motive of the HIV core protein p24; see Giacomini at al., Scand. J. Immunol. 48 (1998), 248-253.

In this context, the identification of PTGES3 (SEQ ID NO: 20) as a Vif-binding protein by the present invention, renders it or the respective complex with Vif a suitable target for preventing or destroying said interaction. In particular, without intending to be bound by theory, since modulation of immunoregulatory effects during HIV pathogenesis by a direct interaction of Vif with PTGES is assumed, said modulation of immunoregulatory effects in the course of HIV infection should be prevented by a respective prohibition of the interaction and instead regulation of the immune system should be under the control of the host as it would be in a healthy organism.

Heat shock proteins: HSPA1, HSPA5, HSPA8, HSPB (Synonyms HSP72, HSP70-1) Accession Number HSPA1: NM_005345, (Synonyms BIP, MIF2, GRP78) Accession Number HSPA5: NM_005347, (Synonyms LAP1, HSC54, HSC70, HSC71, HSP71, HSP73, HSPA10 MGC29929), Accession Numbers HSPA8: NM_006597, NM153201, (Synonyms HSP90B, HSPC2, D6S182) Accession Number HSPB: NM_007355.

Heat shock proteins are highly evolutionary conserved proteins that act as molecular chaperones in cells. Molecular functions are associated with protein folding, transport and assembly. HSPs are also involved in prevention of protein aggregation and degradation. Furthermore, biosynthesis of HSPs was shown to be induced not only by heat but also by other cellular stressors including oxidative stress, influence of heavy metals, bacterial and viral infections.

Heat shock proteins have already been recognized as novel therapeutic tools for treatment of HIV infection by Brenner and Wainberg, Exp. Opin. Biol. Ther. 1 (2001), 1471-2598. However, the role of HSPs in HIV disease pathogenesis is only partly understood. In vitro studies using CD4+-lymphocyte cell lines as well as analysis of lymphocytes of HIV-infected individuals showed that HIV infection induces an increase in synthesis of heat shock proteins; see Wainberg et al., Virology 233 (1997), 364-373; Agnew et al., AIDS 17 (2003), 1985-1988; Füst et al., Mol. Immunol. 42 (2005), 79-85. In addition, it was shown that Hsp70 induced in late stages of infection protects cells from apoptosis; see Mosser et al., Mol. Cell. Biol. 17 (1997), 5217-5327.

Interaction of different HIV proteins with heat shock proteins has been already observed, for instance, the interaction between Nef and Hsp40 was shown to be important for increased Hsp40 translocation into the nucleus of infected cells; see Kumar et al., J. Biol. Chem. 280 (2005), 40041-40050. Additionally, virion incorporation of different heat shock proteins was demonstrated by Curer et al., J. Virol. 76 (2002), 4666-4670. In this context, Gag interaction is critically involved in virion incorporation of Hsp70. Protein complexes of a HECT-RCC1 polypeptide with HIV gag and heat shock proteins and the use of modulators of these complexes for HIV treatment were described in international application WO02/090549. However, Vif complexes with heat shock proteins have not been described before.

Thus, the identification by the method of the present invention of HSPs (HSP90: SEQ ID NO: 21; HSPA1: SEQ ID NOs: 22, 23, 24, 25, 26, 27 and 28, respectively; HSPA5: SEQ ID NOs: 29, 30 and 31, respectively; HSPA8: SEQ ID NOs: 32, 33 and 34, respectively; HSPH1: SEQ ID NO: 35) as direct interaction partners of Vif, generally provides similar options for the development of novel anti-HIV and anti-AIDS strategies, respectively, as already discussed for the above-referenced proteins. In particular, by preventing the interaction of Vif and HSPs, the (ab) use of the host's molecular "chaperone"-machinery by HIV for the folding of viral proteins, the virus' assembly or formation of viral complexes, should be prevented, thereby hampering viral replication cycle. Furthermore, prevention of the interaction prohibits competition between Vif and host for the binding to host HSPs, which finally ensures the maintenance of a sufficient pool of HSPs being at the host's disposal.

Cold shock domain-containing protein E (CSDE1), Accession Number: NM_001007553, Synonyms: UNR protein, N-ras upstream gene protein, is an RNA interacting protein containing the highly conserved cold shock domain (CSD) which consists of about 70 amino acids and contains the nucleic acid binding motifs RNP1 and RNP2. This protein is involved in internal ribosomal entry site (IRES)-mediated translation initiation of human rhinovirus and poliovirus RNA; see Hunt et al., Genes Dev 15 (1999), 437; Boussadia et al., J. Virol. 77 (2003), 3353-3359. It was found to be an mCRD-binding and PABP-interacting protein, and an RNA-independent interaction with the major cytoplasmic poly(A)-binding protein PABP was demonstrated by Chang et al., Genes Dev. 18 (2004), 2010. However, complexes with proteins of HIV have not been described before.

Accordingly, identifying CSDE1 (SEQ ID NO: 36) as a direct target of Vif, also provides similar options as already discussed in connection with the afore-mentioned proteins, such as interrupting viral access to the host's "resources" and hampering viral life cycle, respectively, by for example preventing the respective complex formation between Vif and CSDE1. In particular, competition between Vif and host for the binding to host CSDE1 is prevented thereby maintaining a sufficient pool of CSDE1 at the host's disposal and thus ensuring host's mRNA turnover as would be in the absence of an HIV infection.

A further target according to the invention is RBM39: Homo sapiens RNA binding motif protein 39, Accession Number: NM 184234.1. This transcriptional coactivator for steroid nuclear receptors is involved in pre-mRNA splicing process. This target enables again the development of HIV drugs. SEQ ID NO. 41 discloses the protein part identified which carries the Vif binding motif [amino acids 195 to 530].

A target according to the invention is KIAA1429 (accession number: NM 015496.3). This protein (SEQ ID N0.42) is thought to be involved in mRNA splicing. SEQ ID NO. 42 discloses amino acids 1360 to 1753.

HIV gene expression involves a complex interplay between viral transcription, alternative splicing, nucleocytoplasmic transport and translation, which is often regulated by intrinsic viral regulatory sequences and viral proteins. Transcription enhanced by the HIV protein Tat leads to the synthesis of 30 different viral mRNAs. These viral transcripts include genomic RNAs of about 9 kb, singly spliced mRNAs of about 4 kb and multiply spliced mRNAs of 2 kb. These are derived by alternative splicing of a single full-length transcript, generating mRNAs with common 5' and 3' ends, which are polyadenylated at the 3' end. Both singly spliced and unspliced viral mRNAs contain a RRE (Rev-responsive element) that facilitates the export of intron-containing mRNAs via the binding of the viral protein Rev. Transport of intron-containing mRNAs to the cytoplasm ensures that viral mRNAs can be translated and later packaged into mature virions. Different viral mechanisms are known for down regulation of host mRNA levels including specific inhibition of host mRNA splicing. Therefore, interactions of HIV-Vif with proteins involved in mRNA and pre-mRNA splicing processes provide novel approaches for intervention of virus replication in human cells.

The peptide/protein CUL4A is a further target according to the invention (Homo sapiens cullin 4A (CUL4A), transcript variant 2, Accession Number: NM_003589.2). It is disclosed herein as SEQ ID NO. 43. This sequence encompasses the amino acids 498 to 659.

Cul4A is a core component of multiple cullin-RING-based E3 ubiquitin-protein ligase complexes which mediate the ubiquitination and subsequent proteasomal degradation of target proteins. As a scaffold protein this protein may contribute to catalysis through positioning of the substrate and the ubiquitin-conjugating enzyme. The E3 ubiquitin-protein ligase activity of the complex is dependent on the neddylation of the cullin subunit and is inhibited by the association of the deneddylated cullin subunit with TIP120A/CAND1. The functional specificity of the E3 ubiquitin-protein ligase complex depends on the variable substrate recognition component.

The DDB1-Cul4-ROC1 regulates DNA repair, DNA replication and transcription, and can also be subverted by pathogenic viruses to benefit viral infection. It was shown that the HIV protein Vpr mediates $G_2$ cell cycle arrest by engaging an ubiquitin ligase complex containing DDB1 and Cul4A.

RAG2 is a further target according to the invention (Homo sapiens recombination activating gene 2, Accession Number: NM 000536.2). It is disclosed as SEQ ID NO. 44. The sequences discloses the amino acids 182 to 527.

During lymphocyte development, the genes encoding immunoglobulins and T-cell receptors are assembled from variable (V), diverse (D), and joining (J) gene segments. This V(D)J recombination process allows the generation of an enormous range of binding specificities from a limited source of genetic information. The RAG1/RAG2 complex initiates this process by binding the conserved recombination signal sequence (RRS) and introducing double-strand breaks at the border between the RSS-signal and the adjacent coding segment. This process generates a blunt signal end and a coding end with a closed hairpin structure. These hairpins are intermediates leading to the formation of assembled antigen receptor genes. Defects in RAG2 cause severe immunodeficiency characterized by the presence of activated, anergic and oligoclonal T-cells.

The interaction of Vif with RAG2 as an important regulator of T cell development has not been described before. Therefore, the finding of RAG2 according to the present invention provides a useful potential target for therapeutic intervention of HIV.

CCT5 is a further target according to the invention. (*Homo sapiens* chaperonin containing TCP1, subunit 5, Accession Number NM 012073.3). The sequence SEQ ID NO. 45 discloses the amino acids 1 to 541.

CCT5 is a subunit of the cytosolic chaperonin CCT ring complex assisting the folding of proteins. Unfolded polypeptides enter the central cavity of the complex and are folded in an ATP-dependent manner. The CCT ring complex is known to play a role in the folding of actin and tubulin. Decrease in TCP1 protein levels in HIV infected cells has been shown (Hickman et al. 2003). Interactions of different retroviral proteins including the HIV integrase with subunits of TCP1-complex have already been described. Accordingly, the identification of CCT5 as Vif-interacting protein allows its targeting or the targeting of the respective protein complex in order inhibit the viral access to the host's cell machinery involved in protein folding.

VCP is a further target according to the invention (*Homo sapiens* valosin-containing protein, Accession Number NM 007126.3). Synonyms are transitional endoplasmic reticulum ATPase, TER ATPase, 15S Mg(2+)-ATPase p97 subunit. SEQ ID NO. 46 discloses amino acids 274 to 806.

The protein VCP is involved in the fragmentation of Golgi stacks during mitosis and for their reassembly after mitosis and the formation of the transitional endoplasmic reticulum. The transfer of membranes from the endoplasmic reticulum to the Golgi apparatus occurs via 50-70 nm transition vesicles which derive from part-rough, part-smooth transitional elements of the endoplasmic reticulum. Vesicle budding from the tER is an ATP-dependent process. The ternary complex containing UFD1L, VCP and NPLOC4 binds ubiquitinated proteins and is necessary for the export of misfolded proteins from the ER to the cytoplasm, where they are degraded by the proteasome. In this context, VCP is also thought to be involved in the ubiquitin-dependent proteasome degradation pathway of inhibitor κBα (IκBα), an inhibitor of nuclear factor-κB (NFκB) which is a central regulator of immune response. Cell lines transfected with VCP show the constant activation of NFκB, rapid degradation of phosphorylated IκBα (ρ-IκBα), and decreased apoptosis rates after tumor necrosis factor alpha stimulation.

HIV developed efficient mechanisms for down-regulation of CD4 to produce infectious virions. Endoplasmic Reticulum Associated Protein Degradation (ERAD) of CD4 is induced by binding of HIV-Vpu. As Vpu is phosphorylated, it mimics substrates for the E3 complex $SCF^{\beta TrCP}$. In cells that are infected with HIV, $SCF^{\beta TrCP}$ interacts with Vpu and ubiquitinates CD4, which is subsequently degraded by the proteasome. This process is also thought to be dependent on VCP/p97.

It was shown that VCP plays an important role in ERAD and transport processes of proteins. Therefore, the identification of VCP as a Vif-interacting protein by the present invention, provides further options for novel anti-HIV therapeutic strategies.

PDIA3 is a further target according to the invention (*Homo sapiens* protein disulfide isomerase family A, member 3 (PDIA3), Accession Number: NM 005313.4). Synonyms are disulfide isomerase ER-60, ERp60, 58 kDa microsomal protein, p58 and ERp57. SEQ ID NO. 47 discloses the amino acids 322 to 505.

ERp57 is a member of the protein disulphide isomerase family of oxidoreductases, which are involved in native disulphide bond formation in the endoplasmic reticulum of mammalian cells. The enzyme has been proposed to be a glycoprotein-specific oxidoreductase. Different strong disulphide-bonded glycoproteins have been identified as substrates including integrins and laminins (Jessop et al. 2007). Associated with the two ER proteins calnexin and calreticulin ERp57 forms an integral component of the major histocompatibility complex (MHC) class I loading complex. This complex functions to load optimal peptides onto MHC class I molecules for presentation to $CD8^+$ T lymphocytes.

Different viral immune evasion molecules inhibiting class I antigen presentation have been already found. The ICP47 protein of herpes simplex virus and the US6 protein of human cytomegalovirus (HCMV) have been identified as inhibitors of TAP (transporter associated with antigen processing) as important component of the peptide-loading complex. Other viral proteins, e.g. the HCMV protein US3, bind to tapasin and inhibit its ability to facilitate peptide acquisition of by class I molecules.

The interaction of Vif with ERp57 has not been described before. Therefore the invention provides ERp57 and respective protein complexes with HIV-Vif as novel targets for Anti-HIV therapeutics. Because of the central role of the protein for immune response compound inhibiting complex formation could used for inhibition of virus infection and disease progression.

PTPRC is a further target according to the invention (*Homo sapiens* protein tyrosine phosphatase, receptor type, C (PTPRC), transcript variant 3, Accession Number NM 080922.2). SEQ ID NO. 48 discloses amino acids 743 to 1256. Synonyms are leukocyte common antigen, L-CA, T200 and CD45 antigen. The tyrosine phosphatase CD45 is a key positive element in multiple lymphocyte signaling pathways and is required for T-cell activation through the antigen receptor. Upon T-cell activation, recruits an dephosphorylates SKAP1 and FYN. CD45-associated tyrosine phosphatase activity of lymphocytes from patients with different stages of HIV-1 disease was shown to be reduced during disease progression. In contrast, in long-term nonprogressors (LTNPs) the tyrosine phosphatase activity was not significantly impaired. Negative regulation of NFAT1 transcription factor which is turned on during early stages of T cell activation, by CD45 has been observed. Accordingly, the identification of the tyrosine phosphatase CD45 as an interactor of Vif renders it and the respective protein complex with Vif as a suitable target for therapeutic intervention of HIV. Especially, because of its central function in lymphocyte signaling and T cell activation prevention of complex formation with the viral protein can inhibited viral infectivity and disease progression.

CAB39 is a target according to the invention (*Homo sapiens* calcium binding protein 39 (CAB39), Accession Number NM 016289.2). Synonyms are protein Mo25, CGI-66; and FLJ22682. SEQ ID NO. 49 discloses amino acids 80 to 341. Together with the STE20-related adaptor-alpha (STRAD alpha) pseudo kinase this protein forms a regulatory complex capable of stimulating the activity of LKB1 serine/threonine protein kinase. LKB1 has been implicated in regulation of cell proliferation and polarity. LKB1 is thought to be function as a as tumour suppressor. Interactions of CAB39 with viral or retroviral proteins have not been described before. The identification of CAB39 as interactor of Vif is believed to provide a further suitable target for development of novel anti-HIV therapies.

PPM1B is a target according to the invention (*Homo sapiens* protein phosphatase 1B (formerly 2C), Accession Number. NM_002706.4). Synonyms are protein phosphatase 2C isoform beta and PP2C-beta. SEQ ID NO. 50 discloses the amino acids 258 to 479. The protein encoded by this gene is a member of the PP2C family of Ser/Thr protein phosphatases. PP2C family members are known to be negative regulators of cell stress response pathways. This phosphatase has been shown to dephosphorylate cyclin-dependent kinases (CDKs), and thus may be involved in cell cycle control. Overexpression of this phosphatase is reported to cause cell-growth arrest or cell death. PPM1B was shown to be associated with the IKB kinase complex and is therefore thought to be involved in regulation of NF-KB activity. Interactions of PPM1B with HIV-proteins have not been described before. The identification of this regulator of cell stress responses as Vif-interacting protein may be used for development of novel therapeutic compounds.

RAB4A is a target according to the invention (*Homo sapiens* RAB4A, member RAS oncogene family (RAB4A), mRNA, Accession Number: NM_004578.2). SEQ ID NO. 51 discloses the amino acids 115 to 218.

RAB21 is a target according to the invention (*Homo sapiens* RAB21, member RAS oncogene family (RAB21), Accession Number. NM_014999) SEQ ID NO. 52 discloses amino acids 95 to 225.

Rab genes encode a subgroup of small GTP-binding proteins within the ras super-family that regulate targeting and fusion of transport vesicles within the secretory and endocytic pathways. Different viruses including HIV use various elements of endocytic/trafficking machinery to get into the host cells and to make their infection successful.

Therefore, the interaction of Vif with host proteins involved in protein transport and trafficking provide new possibilities for development of novel anti-viral therapeutic strategies.

ELF4A is particularly preferred. The following targets are likewise very preferred CCT5, CUL4A, HSP90, HSPA1, HSPA5, HSPA8, HSPH1, RAB4A, RAB21, RAG2, PDIA3, PTEN, PTPRC, TPT1 and VCP.

The invention relates to a composition comprising the viral infectivity factor protein (Vif) from the family of Retroviridae or peptide fragments thereof which are over about 12 amino acids and the EIF4A2 protein or peptide fragments thereof which are over about 12 amino, wherein the protein or peptide fragments are capable of binding one another. The peptide may also have 12 amino acids. Preferably the peptides are longer than 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids and 24 amino acids. Ideally, the peptides are shorter than the full length of the protein per se. To make an example of what is meant the protein EIF4A2 in the composition may be 12 amino acids or longer but its maximum length corresponds to the known full length of the protein.

Preferably this viral infectivity factor protein (Vif) is from HIV. More preferably the viral infectivity factor protein (Vif) from HIV as a sequence according to SEQ ID NO. 2 or is encoded by a sequence according to SEQ ID NO. 1 or peptide fragments thereof which are capable of binding EIF4A2.

In one embodiment of the inventive composition the two proteins or peptides are in a complex.

The invention relates to an antibody that specifically binds to the complex of claim 4 or the binding domain of the corresponding HIV protein and/or the human protein or peptide, respectively.

The invention relates to a method for screening compounds, capable of modulating complex formation and/or complex stability comprising the steps of: (a) subjecting a test compound to (i) the composition outlined herein above; and/or (ii) the complex outlined herein above, (b) monitoring changes in complex formation and/or complex stability; and (c) determining a compound as capable of modulating complex formation and/or stability based on its ability to change complex formation between the proteins of (i) and/or change of stability of (ii) compared to a control.

The invention relates to a method for screening compounds, capable of modulating complex formation and/or complex stability of VIF and EIF4A2 comprising the steps of (a) subjecting a test compound to a composition comprising an EIF4A2 protein, or the protein encoded by SEQ ID NO. 9, or fragments thereof, (b) identifying such compounds which are capable of binding the EIF4A2 protein, or the protein encoded by SEQ ID NO. 9, or fragments thereof, (c) subjecting the identified candidate compound from step (b) to, (i) the composition according to the invention and/or, (ii) the complex outlined above, (b) monitoring changes in complex formation and/or complex stability and (c) determining a compound as capable of modulating complex formation and/or stability based on its ability to change complex formation between the proteins of (i) and/or change of stability of (ii) compared to a control. The EIF4A2 protein in this method may also be the full length protein.

The invention relates to a protein with a sequence according to EIF4A2 (SEQ ID NO: 9) or smaller peptide fragments thereof or derivatives thereof, wherein the protein, derivative or peptide is able to bind a viral infectivity factor protein (Vif) from the family of Retroviridae. Preferably said protein, derivative or peptide is able to bind a HIV viral infectivity factor protein (Vif).

The invention relates to a protein with a sequence selected from the group consisting of: PTEN (SEQ ID NOs: 4 and 5), HERC4 (SEQ ID NOs: 6 and 7), Tom1L1 (SEQ ID NO: 8), EIF4A2 (SEQ ID NO: 9), TCTP (TPT1: SEQ ID NOs: 10, 11, 12 and 13), NUP50 (SEQ ID NO: 14), CTCF (SEQ ID NO: 15), hnRPU (SEQ ID NO: 16), MRCL (MRCL3: SEQ ID NO: 17), SDCCAG1 (SEQ ID NOs: 18 and 19), PTGES3 (SEQ ID NO: 20), HSPs (HSP90: SEQ ID NO: 21; HSPA1: SEQ ID NOs: 22, 23, 24, 25, 26, 27 and 28; HSPA5: SEQ ID NOs: 29, 30 and 31; HSPA8: SEQ ID NOs: 32, 33 and 34; HSPH1: SEQ ID NO: 35) and CSDE1 (SEQ ID NO: 36), KIA1429 (SEQ ID NO: 42), CUL4A (SEQ ID NO: 43), RAG2 (SEQ ID NO: 44), CCT5 (SEQ ID NO: 45), VCP (SEQ ID NO: 46), PDIA3 (SEQ ID NO: 47), PTPRC (SEQ ID NO: 48), CAB39 (SEQ ID NO: 49) PPM1B (SEQ ID NO: 50), RAB4A (SEQ ID NO: 51) RAB21 (SEQ ID NO: 52), or fragments or derivatives of any one thereof, wherein the protein or peptide is able to bind Vif.

The invention relates to a kit or assay system comprising a composition according to the invention and/or an antibody according to the invention and/or a protein according to the invention The above-referenced Vif binding proteins identified by using the method of in the present invention have not been previously described as direct targets of Vif and therefore are specifically subject of the present invention.

As already described above, Vif is believed to act as "adapter" connecting viral factors to host factors, an interaction upon which several cellular functions of the host are either interrupted, reprogrammed or abused for viral purposes, wherein these different functions of Vif are effected by binding of Vif to different host proteins. Thus, Vif exerts several different effects, depending on the protein it interacts with. As described above and without intending to be bound by theory, Vif affects apoptosis when bound to PTEN or TCTP; it modifies protein sorting and degradation when interacting with TOM1L1; it influences the host's nucleocytoplasmic transport machinery in case of forming a complex with Nup50, as well as the organization of the cytoskeleton when binding to MRLC. Furthermore, Vif is assumed to compete for and thereby deduct initiation factors or transcription factors from the host when binding to for example EIF4A2 or CTCF. Additionally, Vif is believed to affect host's immune regulation when forming a complex with PTGES and is further assumed to abuse host's "protein folding"-machinery when bound to HSPs as well as to deactivate APOBEC3G, by binding to for example HERC E3.

However, as already discussed for each individual protein, these effects of Vif are believed to be prevented by developing novel strategies based on the knowledge of said new class of Vif-binding proteins identified by the method of the present invention, which hitherto have not been described and known. As already mentioned supra, one example of a novel anti-HIV strategy may comprise the supply of the identified proteins or mimetics thereof, or the administration of compounds, capable of either influencing the expression of the respective identified protein or capable of affecting (preventing or destructing) respective complexes between the identified host protein and Vif. However, there may be several modes to modulate either the interaction of Vif with the identified (human) host protein or the individual protein(s). Thus, these newly identified binding partners of Vif represent novel targets for therapeutic intervention and pharmacologic modulation, respectively.

Furthermore, in addition to the proteins identified by the method of the present invention as being a target of Vif, the complex between Vif and host protein may also be used for analytic, therapeutic or diagnostic applications in the field of HIV/AIDS. In particular, complexes between Vif and host proteins identified according to the method of the present invention, preferably between Vif and the above-referenced proteins also provide suitable targets for respective analysis or development of novel anti-HIV/anti-AIDS strategies. However, a complex according to the present invention does not only comprise full length proteins but also fragments of target and host proteins as well as homologues or derivatives thereof. In this context, it will be understood that the complex according to the present invention may comprise any fragment or minimum portion of the target and/or host protein as long as they are capable of forming a respective complex interaction. The protein-protein complexes of the present invention may be used, for example, for diagnosing HIV disease development, in the performance of which they can be incorporated into a protein microchip or microarray.

Thus, in a further aspect the present invention provides a complex comprising an HIV protein, preferably an accessory HIV protein such as Vif, and a protein encoded by a nucleic acid molecule identified as described before or obtainable by the method of the present invention.

The invention also relates to the use of nucleic acids encoding the novel targets identified herein for the production of the compositions or the complexes disclosed herein.

Furthermore, a protein may be desirable which generally corresponds to the protein identified by the present invention, but which is not longer capable of forming a complex with Vif. These proteins may be achieved by for example modulating the amino acid sequence of an identified protein, for example, by substitution, deletion or addition, wherein those modifications as well as the method of how to affect them are known to the person skilled in the art. In particular, those proteins may be considered as useful for analytical purposes such as for determining the binding region and amino acids essential for binding to Vif, respectively. However, there are several purposes conceivable for designing and using respective proteins, capable for example on one hand to exert the "usual healthy function" but on the other hand not able to bind to Vif, thereby denying the viral access to the cell and to maintain the usual cellular function. Hence, in another embodiment, the present invention relates to a protein derived from the protein encoded by the nucleic acid molecule identified in accordance with the present invention by way of amino acid substitution, deletion and/or addition which is no longer capable of forming a complex as characterized above.

Even further provided is an antibody that specifically binds to the complex as characterized above or the binding domain of the corresponding HIV protein and the human protein, respectively, or the above referenced protein which is derived from the protein encoded by the nucleic acid molecule of the present invention, but which by way of amino acid sequence alterations is no longer capable of forming a respective complex.

Suitable antibodies useful in accordance with the present invention are preferably monoclonal antibodies, but also synthetic antibodies as well as fragments of antibodies, such as Fab, Fv or scFv fragments etc. Antibodies or fragments thereof can be obtained by using methods which are described, e.g., in Harlow and Lane "Antibodies, A Laboratory Manual", CSH Press, Cold Spring Harbor, 1988 or European patent application EP-A 0 451 216 and references cited therein. The production of chimeric antibodies is described, for example, in international application WO 89/09622, and in particular, methods for the production of humanized antibodies are described in, e.g., EP-A1 0 239 400 and WO 90/07861. Further sources of antibodies to be utilized in accordance with the present invention are so-called xenogeneic antibodies. The general principle for the production of xenogeneic antibodies such as human antibodies in mice is described in, e.g., international applications WO 91/10741, WO 94/02602, WO 96/34096 and WO 96/33735.

One major gist of the present invention is the identification of host proteins, preferably human proteins, capable of interacting with HIV-associated proteins such as Vif. However, once a host protein is identified by the method of the present invention as to bind to Vif, this further provides a new contact point to interfere with the viral life cycle. Since the HIV virus is strongly dependent on the host's cell machinery to maintain its life cycle and multiplicate, respectively, and since further Vif is believed to be an "adapter", inter alia having the "function" to provide viral access to the host's cellular "resources", the obstruction of this interaction between virus and host is believed to be a promising therapeutic tool to stop viral replication, infection progression and the onset of AIDS, respectively. Thus, the knowledge of novel Vif-binding proteins, identified in accordance with the method of the present invention and hitherto not known to bind to Vif, allows for the screening for suitable compounds capable of affecting either Vif, the Vif-binding protein or the interaction between them.

Thus, besides identification of Vif-interacting proteins by the method of the present invention, it was another gist of the present invention to identify and screen for, respectively, compounds, capable of affecting the interaction of host protein and Vif, preferably of inhibiting or hampering said interaction. One way of how to discover respective compounds may comprise exposing the cell in which the interaction is to occur and to be affected, for example, inhibited, Vif itself or the interacting protein to compounds, i.e. test compounds with respect to their capability to exert the above-exemplified effects. In particular, a test compound may be subjected to the cell in which the assay is to be performed prior, during or after complex formation between the HIV target protein or a fragment thereof with its putative interacting partner such as a host protein. Changes upon contact with the compound in complex formation and/or stability can be monitored and the test compound will be selected for its capability of modulating the binding of Vif to the host protein, which preferably is a protein identified in accordance with the method of the present invention as described supra.

The compound's mode of action can be different, i.e. it may interact with Vif itself or the host protein, preferably identified by the method of the present invention, wherein said interaction may occur at the binding site of the protein, usually responsible for binding to the respective interaction partner, thereby blocking said site. However, the interaction may also occur at a site, usually not directly involved in binding to a potential interacting molecule, thereby for example changing the protein's conformation leading either to disappearance or alteration of the binding site and as a consequence preventing the afore-mentioned interaction. Thus, the test compound may act either as a competitive or allosteric inhibitor. Furthermore, in accordance with the present invention, "modulating" or "affecting" does not mean only to affect the interaction in the course of its formation, but also to act on already formed complexes, i.e. to destruct them. However, as already mentioned above, in case of successful interference with said host protein/Vif interaction, the virus is obstructed in its access to the host's cell machinery and viral infection and spread, respectively, should be prevented or at least limited to a high extent.

Thus, in a further embodiment, the present invention relates to a method for screening compounds, capable of modulating complex formation and/or complex stability comprising the steps of:
(a) subjecting a test compound to
  (i) the HIV target-protein and the human protein as defined and characterized 3D supra; or
  (ii) the complex according to the present invention;
(b) monitoring changes in complex formation and/or complex stability; and
(c) determining a compound as capable of modulating complex formation and/or stability based on its ability to change complex formation between the proteins of (i) and/or change of stability of (ii) compared to a control.

Although the method is useful for screening novel compounds having the desired effect and characteristics, respectively, this method is also useful to assay compounds or drugs known or believed to have antiviral properties for their real efficacy and effect, respectively. In particular, the methods using the protein complexes according to the present invention can also be used for functional studies and quality control of Vif-related therapeutic polynucleotides, proteins, peptides or antibodies as described in, for example, international application WO 06/111866. Thus, in a particular embodiment, the present invention relates to the above referenced method for analysis of efficiency of a known antiviral drug.

Although there are several ways known in the art to detect complex formation, stability and binding constants of complexes, respectively, in the absence and presence of a potential modulating compound, and methods such as isothermal calorimetry, surface plasmon resonance spectroscopy, fluorescence techniques and NMR-spectroscopy are popular to be used for the respective investigations and may also be used in the present invention, however, one drawback of the above methods is their requirement of an extensive experimental setup and expensive equipment. Therefore, in a preferred embodiment of the present invention, the complex formation and/or stability is tested in a GST-pulldown experiment followed by SDS gel analysis, which is described in detail in Example 3. The performance of SDS-PAGEs is known to the person skilled in the art and well described in the pertinent textbooks such as the current editions of Molecular Cloning: A Laboratory Manual, (Sambrook et al., (1989) Molecular Cloning: A Laboratory Manual, 2nd ed., Cold Spring Harbor Laboratory Press. For testing known pharmaceutical compounds and drugs for their real antiviral effect it is generally referred to the standard textbook "In vitro Methods in Pharmaceutical Research", Academic Press, 1997.

According to the method of the present invention a compound or collection of compounds is assessed as to be capable of modulating the formation of a complex when it is hampered and decreased, respectively, in the presence of said compound or collection of compounds compared to a control where no compound is added. The same applies of course when testing for complex stability and binding constant, respectively, where a compound is assessed as to be capable of modulating complex stability when said stability is weakened (decreased) in the presence of said compound compared to a control where no compound is added. In general, according to the present invention, the decrease of complex formation or complex stability compared to performing the method without the test compound is indicative for a putative prospective therapeutic agent (drug). The so identified drug can further be placed into any standard assay to test its effect on the HIV life cycle, i.e. for example viral replication and multiplication, respectively. A drug is then selected that preferably rescues and/or confers resistance to disorders mediated by HIV infection.

From the above, the present invention provides a number of newly identified host proteins binding to Vif and respective complexes with the HIV protein, i.e. viable targets for screening compounds that are expected to interfere with the HIV life cycle and thus hold great promise as potential therapeutics which ameliorate viral diseases, preferably lentiviral diseases such as AIDS. Compounds in accordance with the present invention can comprise any substance which exhibits the desired effect, i.e. being capable of interfering with the interaction of Vif with a host protein by affecting either Vif, the host protein or their respective interaction. Such compounds include but are not limited to peptides, polypeptides, PNAs, peptide mimetics, antibodies, nucleic acid molecules, aptamers or small organic compounds, either naturally occurring or synthetically prepared.

Once a potential compound is identified, additionally chemical analogues can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively synthesized de novo. The synthesis of those potential compounds is known to the person skilled in the art.

Although the compounds which can be identified by the above mentioned method to be capable of affecting the interaction of Vif with its interacting molecule such as (human) host protein are not limited, however, in a preferred embodiment of the present invention, the compound is selected from the group consisting of antibodies, proteins, peptides and aptamers, and preferably is a peptide. In a further preferred embodiment of the present invention, the peptide is derived from the HIV target protein or from the human protein and preferably consists of about 10 to 20 amino acids.

Suitable peptides may also be obtained by the method for particularly detecting protein-peptide interactions in vivo and isolating the respective interaction partner(s) as disclosed by the applicant in pending European patent application EP 06 018 277.1 "Means and methods for detecting protein-peptide interactions", filed on Aug. 31, 2006, and its subsequent international application to be filed on Aug. 31, 2007. However, of course also synthetic peptides for example derived from proteins identified according to the method of the present invention are envisaged and can be prepared using the well known techniques of solid phase, liquid phase, or peptide condensation techniques, or any combination thereof. They can include natural and unnatural amino acids. Useful peptides may comprise D-amino acids, a combination of D- and L-amino acids, and various "designer" amino acids (e.g. β-methyl amino acids, Ca-methyl amino acids, and Na-methyl amino acids, etc.) to convey special properties. As already mentioned in connection with proteins derived from those identified according to the method of the present invention, but comprising a modified amino acid sequence, also peptides may be used, for the identification of binding regions or minimum required amino acid sequence to form a respective complex. According to the present invention, preferably the peptides used for the identification of interaction domains of the proteins determined as binding to Vif and as described in detail in the Example 4, were prepared as described in, for example, international application WO 05/111061.

In addition, besides the newly identified compounds, the present invention also contemplates the validation of compounds or agents which are known to bind to any one of the Vif interacting proteins, identified according to the method of the present invention, but hitherto have not been considered to be useful in the treatment of viral diseases, in particular lentiviral disease such as AIDS. Such compounds may be easily retrieved from the literature concerning any one of the Vif-interacting proteins, for example in patent databases such as "espacenet" hosted by the European Patent Office or in databases of public literature, e.g. "Medline". In addition, the person skilled in the art may identify compounds to be used in accordance with the present invention by screening so-called "primary databases" such as "Genbank", "EMBL" or "UniprotKB/Swiss-Prot" for nucleotide and protein sequences, respectively, for example by entering the Accession Number or the IUPAC-nomenclature or the name of the protein. The nucleotide and amino acid sequences in the mentioned databases are usually annotated with corresponding citations which in term provide further information with respect to regulation of the corresponding genes and thus guidance for modulating agents to be used in accordance with the present invention. In addition, so called "secondary databases" can be used, for example "PROSITE", "PRINTS", "Pfam", "INTER Pro", "SCOP" or "CATH", being database of protein families and domains, providing fingerprints as classification of sequences, or protein structures. A most suitable web interface allowed to start searching is provided by "Entrez" of NCBI and sequence retrieval system "SRS", respectively. Often a search with keywords in "Google" will already be successful in identifying suitable sources of information.

For the screening method of the present invention the target protein, the host protein or the compound, capable of affecting the interaction may be affixed to a solid surface. One way to perform the method of the present invention can be, for example, to attach the target protein (Vif) to a solid support which is then washed to remove excessive target protein which is not attached. Subsequently, the support is contacted with and accordingly Vif is exposed to, for example, a labelled candidate protein to be tested for interaction or a test compound. Afterwards, the solid support is washed again to remove the protein or compound not bound to the target protein and the amount remaining with the solid support and thereby identified as to be bound to Vif can be determined. Alternatively, or in addition, the dissociation constant between the labelled compound and Vif, for example can be determined. Suitable labels for either Vif, the candidate protein or the compound are well known in the art and include enzymes, fluorophores (e.g., fluorescene isothiocyanate (FITC), phycoerythrin (PE), Texas Red (TR), rhodamine, free or chelated lanthanide series salts, especially $Eu^{3+}$, to name a few fluorophores), chromophores, radioisotopes such as $^{35}S$, chelating agents, dyes, colloidal gold, latex particles, ligands (e.g. biotin), and chemiluminescent agents.

Hence, in a further preferred embodiment of the method of the present invention the HIV target protein, the human protein or the compound to be screened is arranged on a solid support, preferably wherein the solid support is an array or chip, such as a micro chip or a microarray. In this context, the present invention naturally also relates to a chip or array for use in the methods of the present invention.

Methods for attaching for example proteins to a solid support are well known in the art and include for example linking a tag to a target protein. In accordance with the method of the present invention and described in detail in Example 3, the tag is, for example, glutathione-S-transferase (GST) and the target protein is Vif, preferably, wherein Vif is expressed as the respective Vif-GST fusion protein. Furthermore, a respective solid support and matrix, respectively is provided, such as glutathione(GSH)-agarose beads. After contacting the GST-tagged Vif to the solid support and subsequent washing to remove unreacted species, Vif is bound to the support via the glutathione-GST-interaction. There are several further ways for attaching the protein to a solid support such as linking biotin to Vif and linking avidin to the solid support. It is within the general knowledge of the person skilled in the art that the choice of the respective suited way of how to attach the protein to the solid support may depend on individual characteristics of the assay to be performed and the experimental setup, respectively.

However, in a particular preferred embodiment of the method of the present invention for screening compounds, capable of modulating complex formation and/or complex stability, the HIV target protein is a fusion protein comprising glutathlone-S transferase and preferably, the human protein is labelled with $S^{35}$-methionine.

In an even more preferred embodiment of the present invention, the complex formation results from protein-protein interaction in a cell-based two- or three-hybrid system.

Although the above assay has been exemplarily described for the target protein (Vif) to be attached to the solid support, the person skilled in the art knows that this assay of course can be performed vice versa, i.e. by attaching for example the candidate protein to the solid support.

When performing screening methods, it is often intended to screen a variety of compounds in one experiment. Therefore, the methods of the present invention generally can be designed in a format for use in conventional laboratory or adapted for high throughput screening. In this context, the term "high throughput screening" (HTS) refers to an assay design that allows easy analysis of multiple samples simultaneously, and capacity for robotic manipulation. Another desired feature of high throughput assays is an assay design that is optimized to reduce reagent usage, or minimizes the number of manipulations in order to achieve the analysis desired.

Of course in a further embodiment, the present invention relates to a compound which could have been identified or was obtainable by the method of the present invention, preferably wherein said compound hitherto has not been disclosed in the prior art as a drug for the treatment of a viral disease, in particular a lentiviral disease, such as AIDS.

Furthermore, the present invention relates to a pharmaceutical composition comprising an antibody or a compound according to the present invention and optionally a pharmaceutically acceptable carrier. The pharmaceutical composition of the present invention can be formulated according to methods well known in the art; see for example Remington: The Science and Practice of Pharmacy (2000) by the University of Sciences in Philadelphia, ISBN 0-683-306472. Suitable pharmaceutically acceptable carriers can be taken from corresponding literature and include, for example, phosphate-buffered saline solutions, water, emulsions, such as oil/water emulsions, various types of wetting agents, sterile solutions etc. The pharmaceutical compositions can be administered to the subject at a suitable dose, wherein the suitable compositions may be effected by different ways, i.e., by suitable administration routes some of which are described in the respective literature and include, for example, oral, intranasal, rectal, topical, intraperitoneal, intravenous, intramuscular, subcutaneous, subdermal, transdermal, intrathecal, and intracranial administration. Aerosol formulations such as nasal spray formulations include for example purified aqueous or other solutions of the active agent with preservative agents and isotonic agents. Such formulations are preferably adjusted to a pH and isotonic state compatible with the nasal mucous membrane. Formulations for rectal or vaginal administration may be presented as a suppository with a suitable carrier. Further guidance regarding formulations that are suitable for various types of administration can be found in Remington's Pharmaceutical Sciences, Mace Publishing Company, Philadelphia, Pa., 17th ed. (1985) and corresponding updates. For a brief review of methods for drug delivery see Langer, Science 249 (1990), 1527-1533.

The dosage regimen will be determined by the attending physician and clinical factors. As is well known in the medical arts, dosages for any one patient depends on many factors, including the patient's size, body surface area, age, the particular compound to be administered, sex, time and route of administration, general health, and other drugs being administered concurrently. Preparations for parenteral administration may include sterile aqueous or non-aqueous solutions, suspensions, and emulsions. Examples of non-aqueous solvents comprise for example propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and the like. Preservatives and other additives may also be present such as, for example, antimicrobials, antioxidants, chelating agents, and inert gases. Furthermore, the pharmaceutical composition may also be formulated as a vaccine, for example, if the pharmaceutical composition of the invention comprises an anti-HIV antibody for passive immunization.

In addition, co-administration or sequential administration of other agents may be desirable. A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index and it can be expressed as the ratio LD50/ED50. As mentioned already supra, dosage of the agent will depend on the treatment, route of administration, the nature of the therapeutics, sensitivity of the patient to the therapeutics, etc. Utilizing LDSO animal data, and other information, a clinician can determine the maximum safe dose for an individual. The composition can be administered to the subject in a series of more than one administration. For therapeutic compositions, regular periodic administration will sometimes be required or may be desirable. Therapeutic regimens will vary with the agent, e.g. a small organic compound may be taken for extended periods of time on a daily or semi-daily basis, while more selective agents such as peptide mimetics or antibodies may be administered for more defined time courses, e.g. one, two, three ore more days; one or more weeks; one or more months etc.; taken daily, semi-daily, semi-weekly, weekly, etc.

Further to the detection and identification of proteins forming a complex with Vif as well as compounds, capable of affecting said complex formation and/or -stability, one major interest relates to the "nature" of the complex, in particular the complex according to the present invention, i.e. formed between viral- and host factor. Since, in particular, when considering therapeutic approaches, the complex itself may be considered as a drug target, knowledge of the characteristics of the respective complex is necessary for the development of therapeutic agents and therapies, respectively. Typical characteristics of a complex comprise physical or structural characteristics such as stability, type, size (multimeric or monomeric complex), shape and three dimensional structure, but also biological properties such as the amino acid composition of the binding region or the type of interactions in the binding region as well as the impact of complex formation on, for example, generating further binding sites the individual complex partners would not have disposed. Generation of those alternate binding sites may be due to, for example, conformational change of at least one complex partner during complex formation or lack of previous binding sites because of either occupying said site by the complex partner or by conformational rearrangement, thereby leading to the disappearance of former binding sites. Furthermore, knowledge of the lifetime of a complex may be important, which depends on various parameters known in the art, such as salt concentration, pH value and the like. Additionally, chemical, magnetic or electrostatic properties may be of interest, for example, the type of interaction by which the complex is held together such as hydrogen bonds as well as surface charge of the complex.

As already mentioned, the knowledge of the above exemplarily enumerated characteristics is important for prediction of, for example, complex behavior or potential binding regions (in particular for agents, capable of modulating formation and/or stability of the complex, and drug targeting. Hence, the knowledge of complex properties provides necessary information, when considering how to affect the respective complex for various purposes such as to destroy it or prevent its formation. As the person skilled in the art will know, there are several ways of how to prepare, detect, and analyze a respective complex. Those methods may include procedures of formation of protein complexes using in vitro and in vivo systems, which can be adapted to the present invention. For instance, methods may comprise synthesis and isolation of the first protein Vif and the second protein selected from the group of host cell proteins and formation of protein complexes using well known in vitro methods. Alternatively, the protein complexes can also be isolated or purified from tissues or cells or produced by recombinant expression of their protein members. Which method is to be used will depend on the type of complex, purpose of investigation as well as individual experimental parameters.

However, in one particular embodiment, the present invention provides a method of preparing, detecting and analyzing the complex of the present invention and defined above, comprising the steps of:
(a) synthesizing and/or isolating the HIV protein;
(b) synthesizing and/or isolating the human protein;
(c) contacting proteins of (a) and (b);
(d) monitoring complex formation; and optionally;
(e) determining complex characteristics (stability or kinetics) by known in vitro methods.

In yet another embodiment the present invention relates to a diagnostic composition comprising the nucleic acid, the vector, the recombinant host cell, the protein, the complex, the antibody, the compound and/or the chip or array of the present invention.

As already described supra, once a compound is identified according to the present invention to interfere with complex formation and/or stability, this is believed to be a promising therapeutic tool and therefore can be used for developing a therapeutic agent, drug and medicament, respectively. Said drug is preferably able to prevent complex formation or to disrupt already formed complexes or at least to decrease complex stability and therefore to inhibit viral access to and viral effect on the host's cell machinery. However, if the viral access is denied, consequently viral replication, multiplication, spread and onset of the viral disease such as AIDS, respectively is prevented or assumed to be at least decreased to a high extent. Furthermore, the host's cell machinery is maintained to "work" for the host only and not being abused by the virus.

Therefore, the present invention further relates to the use of the aforementioned compound, capable of interfering with formation and/or stability of the complex of the present invention for the preparation of a medicament for the treatment of lentiviral diseases, preferably AIDS.

In a further embodiment, the present invention also relates to a kit or assay system for use in the methods of the present invention, said kit or assay system comprising a component of the present invention as described supra, and/or reagents, automation tools, storage devices, liquid handling robots, monitoring arrangements or the like. In particular, the present invention relates to a kit for use in any one of the methods as described above, i.e. for identifying, cloning, preparing, screening, monitoring, determining, testing, analyzing and/or using the nucleic acid molecules, proteins, compounds, complexes and complex formation, respectively, or compositions of the present invention. Therefore, such a kit preferably comprises the essential components such as the target protein (Vif), one or more candidate (host) protein(s) or fragments thereof, or recombinant nucleic acid molecules encoding the respective proteins (Vif, candidate protein or fragment), more preferably in the form of a corresponding first and second expressible nucleic acid molecule. Even more preferably, the expressible nucleic acid molecules are present in an expression vector suitable for the particular cells in which the interaction assay is performed. Appropriate expression vectors can be, for example, yeast expression vectors or mammalian cell expression vectors, depending on the cells in which the method is to be performed.

If desired, the kit further contains reagents, for example, that result in optimal transfection efficiency of the nucleic acids for the particular host cell type. In addition, appropriate host cells can be included in a kit, although such cells generally are available or can be selected for a particular embodiment of the method. Preferably, the kit of the present invention contains reagents such as those described hereinbefore useful for conducting any of the above-described methods of the present invention, comprising for example selectable markers, medium or media components, reference samples, microarrays, culture vessels, vectors, proteins, peptides, and maybe a suitable detection means, spectroscopic devices and/or monitoring systems, capable of monitoring complex formation, i.e. decrease or increase of complex formation of (optionally tagged) Vif and its interacting molecule(s) such as (optionally tagged) host protein(s). Furthermore, an increased or decreased binding capacity compared to a control may be detected by, for example, labels comprising fluorescent label, phosphorescent label, radioactive label, which are known to those skilled in the art. Optionally, the kit further comprises instructions on how to perform any method of the present invention, preferably the use of the kit in the methods concerning the identification and/or cloning of nucleic acid molecules encoding interacting molecules of Vif or validation or assessment of potential drugs, agents, compositions or compounds influencing (inhibiting or enhancing) said interaction. These instructions can be provided to detail the use of the components of the kit, such as written instructions, video presentations, or instructions in a format that can be opened on a computer, e.g. a diskette or CD-ROM disk.

Furthermore, such a kit would typically comprise a compartmentalized carrier suitable to hold in close confinement at least one container and the compounds of the kit may be sterile, where appropriate. The kit may further include a transfer means, such as pipets, for transferring any fluent component. The kit of the present invention is preferably suitable for commercial manufacture and scale and can still further include appropriate standards, positive and negative controls.

It will be apparent that the methods and components of the present invention, the proteins obtained thereby, as well as the uses as substantially described herein or illustrated in the description and the examples, are also subject of the present invention and claimed herewith. In this respect, it is also understood that the embodiments as described in any one of the examples, can be independently used and combined with any one of the embodiments described hereinbefore and claimed in the appended claims set. Thus, these and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example, the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using Internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Several documents are cited throughout the text of this specification. Full bibliographic citations may be found at the end of the specification immediately preceding the claims. The contents of all cited references (including literature references, issued patents, published patent applications as cited throughout this application and manufacturers specifications, instructions, etc.) are hereby expressly incorporated by reference, however, there is no admission that any document cited is indeed prior art as to the present invention.

The invention also relates to a diagnostic assay for the detection of HIV, wherein a complex between any of the target proteins or peptides disclosed herein and Vif is detected. Such an assay may make use of blood or any other tissue. Hence, the invention also relates to a diagnostic assay for HIV detection wherein any of the target proteins herein is used.

The above disclosure generally describes the present invention. A more complete understanding can be obtained by reference to the following specific examples which are provided herein for purposes of illustration only and are not intended to limit the scope of the invention.

The peptides claimed herein may be generated as follows. The nucleic sequence encoding the EIF4A2 protein is digested either enzymatically or mechanically sheared in such a way that small fragments are generated. The fragments shall have the desired length. The fragments are cloned into a vector for expression of the encoded peptide. Various peptides are tested for binding to Vif. A binding region may be determined. Also, peptides of a give length may synthesized chemically and binding to Vif may be tested.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed. by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu at al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11, (2001), 98-107.

Example 1

Identification of Novel VIF Interactors

The example demonstrates the identification of protein complexes of a recombinant HIV Vif (SEQ ID NO: 2) with novel human polypeptides encoded by a thymus cDNA-library (CytoTrap® XR Human Thymus cDNA Library, Stratagene).

Bait Construction

The NL4-3 Vif cDNA was cloned into an appropriate vector for expression of heterologous proteins in yeast (pADH-Sos-2xSpc, modified from pSos vector (Sikorski and Hieter, Genetics 122 (1989), 19-27) as a fusion protein with Sos including a small spacer (SEQ ID NO: 3). Vif cDNA was amplified by polymerase chain reaction (PCR) with primer Vif/RsrII (5'-ttttCGGACCGGAAAACAGATGGCAGGT-GATG-3'; SEQ ID NO 37) and Vif/NotI (5' aaatatGCGGC-CGCCTATCTGGGGCTTGTTCCATCTG-3'; SEQ ID NO 38). Following RsrII and NotI restriction digest Vif PCR product was cloned into equally digested pADH-Sos-2xSpc resulting in pADH-Sos-2xSpc-vif to express the amino terminal Sos fusion protein; see FIG. 5.

Library Amplification

Library transformation was performed with *E. coli* (XL10-Gold® Ultracompetent Cells, Stratagene) according to the instructions of the manufacturer. For the library amplification $1 \times 10^7$ individual clones were needed to be sure that most cDNAs are represented in the amplified cDNA library. Therefore 160 mm Petri dishes were used for library amplification. On every Petri dish about $5 \times 10^4$ colony forming units (cfu) can grow. The titer of the purchased thymus cDNA library *E. coli* strain was $2.6 \times 10^5$ *E. coli* per µl. Plates were inoculated with 0.20 µl of the *E. coli* library strain to reach the desired number of cfu.

The *E. coli* library strain was thawed on ice. After thawing the *E. coli* suspension was mixed gently and 41 µl were diluted 1:25 with LB-medium (2.5% (w/v) LB Miller). Before inoculation of the LB-chloramphenicol plates (LB-chloramphenicol agar: LB agar supplemented with 1 ml of filter-sterilized chloramphenicol in a concentration of 30 µg ml$^{-1}$), 100 µl LB-Medium was added to each plate for better distribution of the subsequent added *E. coli* strain. Then 5 µl of the diluted *E. coli* library strain were added to each Petri dish and distributed with the help of autoclaved glass beads (2.85-3.3 mm, Roth). After overnight incubation at 37° C., the *E. coli* colonies were scraped off the plates with the aid of a rubber police man.

The *E. coli* of 10 plates were transferred into a 50 ml centrifuge tube and carefully resuspended in 50 ml LB-chloramphenicol medium. The content of five such centrifuge tubes was then transferred into a sterile 500 ml centrifuge beaker and centrifuged for 15 min (4° C., 6000 rpm (JA-10)). The supernatant was discarded and the cell pellet weight was determined. The pellet was resuspended in 20 ml ice-cold STE buffer (0.1 M NaCl, 10 mM Tris pH 8.0, 1 mM EDTA) containing 10% glycerol. At the end, the appropriate volume containing 3 g E. coli cell pellet was transferred to a 10 ml cryotube and stored at −80° C. Four thymus cDNA pools were generated each pool from 50 Petri dishes. For plasmid isolation the Kit AX2000 (Macherey-Nagel) was used.

Yeast Transformation

The transformation of cdc25-2 yeast cells (MATα, ura3, lys 2, Leu2, trpl cdc25-2, h is 3Δ200, ade 100, GAL+) was performed according to the modified protocol for a high efficient transformation method of Schiestl and Gietz (1989). For preparation of competent yeast cells, 10 ml YEPD medium was inoculated with cdc25-2 yeast cells and incubated over night at 24° C. An appropriate volume of the over night culture was used to inoculate 50 ml YEPD medium to get an $OD_{600}$ of 0.2. After incubation at 24° C. (until $OD_{600}$~0.8) the culture was sedimented (1000 g, 5 min, room temperature), the pellet was washed with sterile $ddH_2O$ and centrifuged as described before. Afterwards the pellet was resuspended in 10 ml LiSORB (100 mM Lithium acetate, 1 M D-sorbitol, in 10 mM Tris, 1 mM EDTA; pH 7.5; filter-sterilized) and again sedimented. The pellet was resuspended in 50 µl LiSORB per transformation (maximal 500 µl). The cells were directly used for transformation.

For prepation of the carrier DNA-mix 10 µl fragmented Carrier-DNA (salmon sperm DNA, 10 mg ml$^{-1}$ in TE buffer) per transformation was boiled at 95° C. for 5 min. The carrier DNA was then mixed with 40 µl LiSORB per transformation and placed on ice for cooling to room temperature.

For the actual transformation, 0.5-1 µg plasmid-DNA, 50 µl carrier DNA-mix and 50 µl competent yeast cells were mixed. The mixture was incubated for 30 min at 24° C. with shaking. 900 µl LiPEG (100 mM Lithium acetate (pH 7.5), 40% (w/v) $PEG_{4000}$, in 10 mM Tris, 1 mM EDTA (pH 7.5), filter-sterilized) were added to each sample and again incubated at 24° C. with shaking for 30 min. 100 µl DMSO were added and the cells were heat shocked for 7 min at 42° C. without shaking. The cells were sedimented (1 min, 1000 g) and resuspended in 100 µl 1 M sorbitol (filter sterilized). 50 µl of the suspension was inoculated on an appropriate selection plate and incubated at 24° C. Colonies appeared after 4-6 days.

Library Screening

The thymus library was transformed by large scale transformation (Schiestl and Gietz, 1995) into the bait strain. A bait strain was generated by transforming the cdc25-2 yeast strain with the pADH-SOS-2xSpc-vif plasmid as described above. A fresh bait strain culture (600 ml with an OD of 1.0) was used for the transformation of 70 µg library plasmid DNA as described above and plated on 160 mm -Leu-Ura+glucose plates. Incubation for 3-4 days at 24° C. resulted in approximately 30000 transformants per plate. For selection of clones expressing Vif interacting proteins, transformants were replica plated with membrane filters onto -Leu-Ura+galactose plates and grown at 37° C. for 4-10 days.

Appearing colonies were picked, resuspended in 200 µl -Leu-Ura+glucose medium and incubated at 24° C. over night. To test whether the growth of putative interaction candidates at 37° C. is dependent on prey expression, clones were plated onto -Leu-Ura+galactose plates as well as on -Leu-Ura+glucose plates following incubation at 37° C. for 5-7 days. The expression of Vif-interacting fusion proteins is under control of the GAL1 inducible promoter of the library plasmid. Therefore, expression was induced by the addition of galactose to the medium (3% galactose and 2% raffinose) and however repressed by the addition of glucose. Yeast cells expressing Vif-interacting proteins of the thymus library are growing only on galactose plates (3% galactose, 2% raffinose) but do not grow on glucose plates; see FIG. 1.

Isolation of Plasmids Comprising an Encoded Vif-Interacting Protein

Plasmids were isolated according to a protocol of Michael Jones using the QIAprep® Spin Miniprep Kit (www.qiagen.com/literature/protocols/pdf/PR04.pdf). A single yeast colony was inoculated into 5 ml -Ura+glucose medium and grown at 24° C. for 24 h with shaking. Cells were harvested by centrifugation for 5 min at 5000×g and resuspended in 250 µl Buffer P1 (Qiagen) containing 0.1 mg/ml RNase A (Qiagen).

The cell suspension was transferred to a fresh 1.5 ml micro centrifuge tube. For disruption, 50-100 µl acid-washed glass beads (Sigma) were added and the suspension was vortexed for 5 min. After settling of the beads, the supernatant was transferred to a fresh 1.5 ml micro centrifuge tube. Then 250 µl lysis buffer P2 (Qiagen) was added to the tube, the tube was inverted 4-6 times and incubated for 5 minutes at room temperature. After incubation, 350 µl neutralization buffer N3 (Qiagen) were added to the tube and the tube was inverted immediately but gently 4-6 times. The lysate was centrifuged at 15000×g for 10 min. Thereafter, the cleared lysate was transferred to QIAprep Spin Column and centrifuged for 1 min at 15000×g. The column was washed by adding 0.75 ml buffer PE (Qiagen) and centrifugation for 1 min at 15000×g. Elution of the DNA was performed by adding 25 µl EB (Qiagen) to the center of the QIAprep Spin Column. After 1 min incubation time, the eluate was obtained by centrifugation for 1 min at 15000×g. Subsequent transformation into $CaCl_2$ competent E. coli was performed with 10 µl eluate. The bacteria were plated on LB-plates containing 50 µg/ml chloramphenicol. Prey plasmids were isolated from E. coli and analyzed by EcoRI/XhoI restriction digest which releases the insert.

Example 2

Detection of Vif Protein Complexes in Yeast Cells

This example demonstrates that the invention is also useful for the detection of specific protein complexes in yeast by expressing a Vif fusion protein and fusion proteins of the identified host factors.

For the identification of the "positive interactors" identified in Example 1, the DNA of their corresponding library sequence was isolated from the cells.

Further to the identification of novel Vif interacting proteins, this interaction was tested for specificity, i.e. for the dependence of the protein-protein interaction on the expression of the first fusion protein (bait), i.e. the target protein being Vif. Therefore, isolated library plasmids of Vif interacting proteins were not only introduced into the yeast strain containing the vector pADH-Sos-2xSpc-vif comprising the encoded first fusion protein, i.e. Vif as target protein, but also additionally introduced into the cdc25-2 yeast strain containing a heterologous bait vector pADH-Sos-2xSpc-cJun as control comprising a fusion protein providing cJun as a "negative control" target protein. As described above, cells were plated onto YNB-Leu, -Ura, and glucose plates and incubated at 24° C. Clones of each transformation assay were suspended in liquid medium and transferred onto one set of galactose- and two sets of glucose plates (each -Ura-Leu), respectively, and incubated at 37° C. On galactose plates the dependency of the interaction is tested on the expression of the prey protein, which is under the control of a galactose inducible promoter. The glucose plates, incubated at 37° C., were used to test for potential growth of revertants. The set of glucose plates, incubated at 24° C., was used as general growth control. The control vector (providing the "negative control" target protein) at the restrictive temperature of 37° C. indicates the binding specificity of the identified novel host cellular interactors to the pADH-Sos-2xSpc bait construct, since there was no growth of cells containing the identified novel host factors in combination with the non-relevant pADH-Sos-2xSpc-cJun construct; see FIG. 2 and FIG. 7. After demonstrating the specificity of the interacting host proteins for binding to Vif, the DNA of their corresponding library sequence was sequenced.

Example 3

Formation of HIV Vif Protein Complexes In Vitro (GST Pull Down)

Vif Vectors

The full-length Vif gene of pNL4.3 was amplified by PCR using primers Vif/Bam (5'-CGCGGATCCACCATG-GAAAACAGATGGCAGGTGATG-3'; SEQ ID NO 39) and Vif/Xho (5'-CCGCTCGAGCTAGTGACCATTCATTG-TATG-3'; SEQ ID NO 40). The PCR amplified Vif DNA was cleaved with BamHI/XhoI, and subcloned into BamHI/XhoI digested pGEX-4T2 expression vector (Amersham PharmaciaBiotech), resulting in pGEX-4T2-Vif, which contains a GST-Vif fusion open reading frame; see FIG. 4.

Expression and Purification of GST-Vif

The expression and purification of GST-Vif was performed according to a modified protocol of Hassaine et al., J. Biol. Chem. 276 (2001), 16885-16893. Therefore, E. coli BL21 codon plus RP (Stratagene) transformed with the pGEX-4T2-Vif plasmid were grown at 30° C. Protein expression was induced at an OD at 600 nm of 0.5-0.7, with 0.1 mM isopropyl-b-D-thiogalactopyranoside for 3 h at 30° C. The bacteria were centrifuged at 5.000×g for 15 min and the pellet was resuspended in phosphate-buffered saline (PBS) containing protease inhibitor (Roche) and lysozyme (1 mg/ml). Bacteria were lysed by sonication (3×30 s) on ice, and the lysate was incubated for 30 min at 4° C. in the presence of 1% Triton X-100 with shaking. Insoluble material was pelleted for 40 min at 14.000×g, and the supernatant was incubated overnight at 4° C. with 50% (v/v) glutathione (GSH)-agarose beads (Amersham). After three washes in 0.5 M NaCl in PBS, the GST fusion proteins immobilized on GSH agarose beads were quantified by electrophoresing an aliquot on a 12% sodium dodecyl sulfate (SDS)-polyacrylamide gel with subsequent staining of the gel with Coomassie Brilliant Blue.

In Vitro Formation of Protein Complexes

Radioactively labelled proteins of the interaction candidates were generated by coupled in vitro transcription-translation (TNT T7 coupled reticulocyte lysate system, Promega) in the presence of $^{35}$S (1000 Ci/mmol; Amersham Pharmacia Biotech) as recommended by the manufacturer using the corresponding library plasmid as template. ⅕ of translated protein extract was incubated with GST-Vif bound to agarose beads.

For one binding experiment, Vif protein corresponding to 40 ml BL21 cells expressing Vif as GST fusion protein was used. Purification protocols have been described above.

The binding of interaction candidates to Vif was performed with shaking for one hour at room temperature in binding buffer containing 20 mM NaCl, 20 mMTris pH 8.0, 0.5% NP40 and bovine serum albumine 100 µg/ml. After incubation beads were pelleted by spinning at 500 g for 2 min. and 4 washing steps with 1 ml washing buffer (binding buffer without serum albumin) were followed. Proteins were eluted with 30 µl 2×SDS sample buffer and half of the eluate was analyzed by SDS polyacrylamide gel electrophoresis (PAGE) followed by autoradiography; see FIG. 3a-c.

Example 4

Identification of Interaction Domains

For the identification of interaction domains, microarrays containing 14 amino acid long peptides deriving from protein sequences of the interacting proteins were produced as described, for example, in international application WO05/111061. Peptides were synthesized following the Fmoc methodology using a fully automated synthesizer (Multipep Automated Peptide Synthesizer, Intavis AG Bioanalytical Instruments). Single peptides were synthesized on separate derivatized cellulose disks (Fmoc-β-alanine cellulose). After finishing synthesis and removing side chain protection groups with TFA cellulose disks were dissolved in 90% TFA (89.5% TFA, 4% trifluoromethanesulfonic acid, 2.5% triisopropylsilane, 4% $H_2O$) over night. Cellulose bond peptides were participated with cold tert-butylmethylether and centrifuged (5 min, 1500 rpm). After washing with tert-butylmethylether, the pellet was dissolved with DMSO. Thereafter, resulting solutions of cellulose-conjugated peptides in DMSO were used for production of arrays by spotting 0.06 µl volumes of the solutions on microscope slides.

Peptide arrays were incubated with solutions of $^{35}$S-labelled interacting proteins to produced in vitro using plasmids isolated from positive clones of the interaction screening and the Promega TNT coupled transcription/translation system according to the recommendations of the supplier. The formation of proteins was verified via SDS gel electrophoresis, autoradiography, and silver staining. Fifty microliters of the crude in vitro synthesized protein were added to 10 ml of 10× Membrane Blocking buffer (Sigma-Aldrich, casein-based blocking buffer, 0.05% sodium azide) and mixed thoroughly. This mixture was applied directly to peptide arrays previously blocked overnight. The incubation was carried out for four hours under constant slow horizontal agitation at room temperature. The supernatant was removed and the membrane was washed three times for ten minutes with TBST 25 mM Tris-Cl, pH 7.5; 125 mM NaCl; 0.1% Tween-20). Complex formation of peptides with $^{35}$S-labelled proteins were detected with imaging screen K (Biorad), which was always erased prior to their use, placed for 70 hours on top of the saran covered face of the spot membrane, and read out on a Personel Molecular Imager FX (Biorad, resolution: 50 µm). The resulting image file was directly evaluated concerning to the intensities of spots using Biorad Quantity One software (Version 4.4).

Example 5

Detection of Protein Complexes in Cell Lysates

This example demonstrates the detection of protein complexes of the present invention in cell lysates of human cells. The experimental method described here can also be used for the development or validation of potential drugs, agents, compositions or compounds influencing (inhibiting or enhancing) the described formation of protein complexes.

The modified human embryonic kidney cell line 293T was maintained in complete medium which consisted of Dulbecco's modified Eagle's medium (DMEM) supplemented with 10% fetal calf Serum, 1% penicillin and streptomycin and 1% glutamine. 293T cells were seeded at 5×10⁶ cells 100-mm dish. For generation of positive controls 293T cells were transfected with 3 μg of pFLAG-A3G which expresses FLAG-tagged Apobec3G as vif interacting protein (24 hours after seeding). The supernatant was removed 48 h post transfection and the cells were washed once in 5 ml of cold PBS. FLAG-A3G-transfected and non-transfected cells were lysed in cold RadioImmuno Precipitation Assay (RIPA) buffer (Pierce, 800 μl per 100-mm dish).

Cell lysates were incubated with solutions of $^{35}$S-labelled vif protein produced in vitro from pcDNA-vif plasmid using the Promega TNT coupled transcription/translation system according to the recommendations of the supplier. For the formation of protein complexes 10 μl of the in vitro translated $^{35}$S-labelled vif protein were incubated with 600 μl of the total cell lysate at room temperature for one hour with agitation. Immunoprecipitation of protein complexes was performed by addition of 25 μl of a suspension of a primary antibody (incubation under rotation 4 h, 4 C.°) and following incubation with 30 μl of a suspension of agarose conjugate protein A/G-agarose (Santa Cruz, incubation under rotation 1 h, 4 C.°). After centrifugation (8000×g, 5 minutes, 4 C.°) and washing with TBS the resulting pellet was resuspended in 10 μl of 4× concentrated electrophoresis sample buffer (125 mM Tris pH 6.8, 4% SDS, 10% glycerol, 2% β-mercaptoethanol) and boiled for 5 minutes.

Equal aliquots of the resulting sample were loaded onto two SDS-Page gels (12%) and separated by electrophoresis. Proteins of the first gel were transferred to PVDF membrane and immunoblotted with appropriate primary and secondary antibody. The second gel was dried and used for detection of $^{35}$S-labelled vif protein in complexes with imaging screen K (Biorad). Therefore, the screen, which was always erased prior use was placed for 48 hours on top of the membrane and read out on a Personal Imager FX (Biorad, resolution 50 μm).

The invention claimed is:

1. A method for screening compounds capable of modulating viral infectivity factor protein (Vif) and EIF4A2 complex formation and/or complex stability comprising the steps of:
   (a) subjecting a test compound to
      i. a composition comprising: (I) a Vif protein and (II) a EIF4A2 protein, wherein the proteins of (I) and (II) are capable of binding one another; and/or
      ii. a complex comprising the two proteins of (I) and (II);
   (b) monitoring changes in complex formation and/or complex stability; and
   (c) determining the compound as capable of modulating complex formation and/or stability based on its ability to change complex formation between the proteins of (i) and/or change the stability of (ii) compared to a control.

2. A method for screening compounds, capable of modulating complex formation and/or complex stability of VIF and EIF4A2 comprising the steps of:
   (a) subjecting a test compound to a composition comprising a protein encoded by SEQ ID NO: 9;
   (b) identifying such compounds which are capable of binding the protein encoded by SEQ ID NO: 9;
   (c) subjecting the identified candidate compound from step (b) to
      (i) the composition of (a) further comprising: a Vif protein, wherein the Vif protein is capable of binding the protein of (a); and/or
      (ii) a complex comprising the two proteins of (a) and (c)(i);
   (d) monitoring changes in complex formation and/or complex stability; and
   (e) determining the compound as capable of modulating complex formation and/or stability based on its ability to change complex formation between the proteins of (i) and/or change of stability of (ii) compared to a control.

3. A method for screening compounds capable of modulating Vif and EIF4A2 complex formation and/or complex stability comprising the steps of:
   a. subjecting a test compound to
      i. a composition comprising: (I) a protein of SEQ ID NO: 2 and (II) a protein of SEQ ID NO: 9; and/or
      ii. a complex comprising the two proteins of (I) and (II);
   b. monitoring changes in complex formation and/or complex stability; and
   c. determining the compound as capable of modulating complex formation and/or stability based on its ability to change complex formation between the proteins of (i) and/or change the stability of (ii) compared to a control.

4. A method for screening compounds, capable of modulating complex formation and/or complex stability of VIF and EIF4A2 comprising the steps of:
   a. subjecting a test compound to a composition comprising a protein encoded by SEQ ID NO: 2;
   b. identifying such compound which is capable of binding the protein encoded by SEQ ID NO: 2;
   c. subjecting the identified candidate compound from step (b) to
      i. a composition comprising: (I) a Vif protein and (II) a EIF4A2 protein, wherein the proteins of (I) and (II) are capable of binding one another; or
      ii. a complex comprising the two proteins of (I) and (II);
   d. monitoring changes in complex formation and/or complex stability; and
   e. determining the compound as capable of modulating complex formation and/or stability based on its ability to change complex formation between the proteins of (i) and/or change of stability of (ii) compared to a control.

* * * * *

SEQUENCE LISTING

```
<160> NUMBER OF SEQ ID NOS: 54

<210> SEQ ID NO 1
<211> LENGTH: 624
<212> TYPE: DNA
<213> ORGANISM: Human immunodeficiency virus
<220> FEATURE:
<221> NAME/KEY: CDS
<222> LOCATION: (1)..(621)

<400> SEQUENCE: 1 atg gat tac aag gat gac gac gat aag agc ccg ggc gga tcc acc atg        48
Met Asp Tyr Lys Asp Asp Asp Asp Lys Ser Pro Gly Gly Ser Thr Met
1               5                   10                  15 gaa aac aga tgg cag gtg atg att gtg tgg caa gta gac agg atg agg        96
Glu Asn Arg Trp Gln Val Met Ile Val Trp Gln Val Asp Arg Met Arg
            20                  25                  30 att aac aca tgg aaa aga tta gta aaa cac cat atg tat att tca agg       144
Ile Asn Thr Trp Lys Arg Leu Val Lys His His Met Tyr Ile Ser Arg
        35                  40                  45 aaa gct aag gac tgg ttt tat aga cat cac tat gaa agt act aat cca       192
Lys Ala Lys Asp Trp Phe Tyr Arg His His Tyr Glu Ser Thr Asn Pro
    50                  55                  60 aaa ata agt tca gaa gta cac atc cca cta ggg gat gct aaa tta gta       240
Lys Ile Ser Ser Glu Val His Ile Pro Leu Gly Asp Ala Lys Leu Val
65                  70                  75                  80 ata aca aca tat tgg ggt ctg cat aca gga gaa aga gac tgg cat ttg       288
Ile Thr Thr Tyr Trp Gly Leu His Thr Gly Glu Arg Asp Trp His Leu
                85                  90                  95 ggt cag gga gtc tcc ata gaa tgg agg aaa aag aga tat agc aca caa       336
Gly Gln Gly Val Ser Ile Glu Trp Arg Lys Lys Arg Tyr Ser Thr Gln
            100                 105                 110 gta gac cct gac cta gca gac caa cta att cat ctg cac tat ttt gat       384
Val Asp Pro Asp Leu Ala Asp Gln Leu Ile His Leu His Tyr Phe Asp
        115                 120                 125 tgt ttt tca gaa tct gct ata aga aat acc ata tta gga cgt ata gtt       432
Cys Phe Ser Glu Ser Ala Ile Arg Asn Thr Ile Leu Gly Arg Ile Val
    130                 135                 140 agt cct agg tgt gaa tat caa gca gga cat aac aag gta gga tct cta       480
Ser Pro Arg Cys Glu Tyr Gln Ala Gly His Asn Lys Val Gly Ser Leu
```

```
                  145                 150                 155                 160
cag tac ttg gca cta gca gca tta ata aaa cca aaa cag ata aag cca          528
Gln Tyr Leu Ala Leu Ala Ala Leu Ile Lys Pro Lys Gln Ile Lys Pro
            165                 170                 175 cct ttg cct agt gtt agg aaa ctg aca gag gac aga tgg aac aag ccc          576
Pro Leu Pro Ser Val Arg Lys Leu Thr Glu Asp Arg Trp Asn Lys Pro
            180                 185                 190 cag aag acc aag ggc cac aga ggg agc cat aca atg aat ggt cac tag          624
Gln Lys Thr Lys Gly His Arg Gly Ser His Thr Met Asn Gly His
            195                 200                 205
```

<210> SEQ ID NO 2
<211> LENGTH: 207
<212> TYPE: PRT
<213> ORGANISM: Human immunodeficiency virus

<400> SEQUENCE: 2

```
Met Asp Tyr Lys Asp Asp Asp Lys Ser Pro Gly Gly Ser Thr Met
1               5                   10                  15

Glu Asn Arg Trp Gln Val Met Ile Val Trp Gln Val Asp Arg Met Arg
                20                  25                  30

Ile Asn Thr Trp Lys Arg Leu Val Lys His His Met Tyr Ile Ser Arg
            35                  40                  45

Lys Ala Lys Asp Trp Phe Tyr Arg His His Tyr Glu Ser Thr Asn Pro
50                  55                  60

Lys Ile Ser Ser Glu Val His Ile Pro Leu Gly Asp Ala Lys Leu Val
65                  70                  75                  80

Ile Thr Thr Tyr Trp Gly Leu His Thr Gly Glu Arg Asp Trp His Leu
                85                  90                  95

Gly Gln Gly Val Ser Ile Glu Trp Arg Lys Lys Arg Tyr Ser Thr Gln
            100                 105                 110

Val Asp Pro Asp Leu Ala Asp Gln Leu Ile His Leu His Tyr Phe Asp
        115                 120                 125

Cys Phe Ser Glu Ser Ala Ile Arg Asn Thr Ile Leu Gly Arg Ile Val
    130                 135                 140

Ser Pro Arg Cys Glu Tyr Gln Ala Gly His Asn Lys Val Gly Ser Leu
145                 150                 155                 160

Gln Tyr Leu Ala Leu Ala Ala Leu Ile Lys Pro Lys Gln Ile Lys Pro
                165                 170                 175

Pro Leu Pro Ser Val Arg Lys Leu Thr Glu Asp Arg Trp Asn Lys Pro
            180                 185                 190

Gln Lys Thr Lys Gly His Arg Gly Ser His Thr Met Asn Gly His
        195                 200                 205
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Gly Gly Gly Ser Gly Gly Gly Ser
1               5
```

<210> SEQ ID NO 4
<211> LENGTH: 171
<212> TYPE: PRT
<213> ORGANISM: Homo sapiens

```
<400> SEQUENCE: 4

Arg Arg Glu Asp Lys Phe Met Tyr Phe Glu Phe Pro Gln Pro Leu Pro
1               5                   10                  15

Val Cys Gly Asp Ile Lys Val Glu Phe Phe His Lys Gln Asn Lys Met
            20                  25                  30

Leu Lys Lys Asp Lys Met Phe His Phe Trp Val Asn Thr Phe Phe Ile
        35                  40                  45

Pro Gly Pro Glu Glu Thr Ser Glu Lys Val Glu Asn Gly Ser Leu Cys
    50                  55                  60

Asp Gln Glu Ile Asp Ser Ile Cys Ser Ile Glu Arg Ala Asp Asn Asp
65                  70                  75                  80

Lys Glu Tyr Leu Val Leu Thr Leu Thr Lys Asn Asp Leu Asp Lys Ala
                85                  90                  95

Asn Lys Asp Lys Ala Asn Arg Tyr Phe Ser Pro Asn Phe Lys Val Lys
            100                 105                 110

Leu Tyr Phe Thr Lys Thr Val Glu Glu Pro Ser Asn Pro Glu Ala Ser
        115                 120                 125

Ser Ser Thr Ser Val Thr Pro Asp Val Ser Asp Asn Glu Pro Asp His
    130                 135                 140

Tyr Arg Tyr Ser Asp Thr Thr Asp Ser Asp Pro Glu Asn Glu Pro Phe
145                 150                 155                 160

Asp Glu Asp Gln His Thr Gln Ile Thr Lys Val
                165                 170

<210> SEQ ID NO 5
<211> LENGTH: 219
<212> TYPE: PRT
<213> ORGANISM: Homo sapiens

<400> SEQUENCE: 5

His Leu Asp Tyr Arg Pro Val Ala Leu Leu Phe His Lys Met Met Phe
1               5                   10                  15

Glu Thr Ile Pro Met Phe Ser Gly Gly Thr Cys Asn Pro Gln Phe Val
            20                  25                  30

Val Cys Gln Leu Lys Val Lys Ile Tyr Ser Ser Asn Ser Gly Pro Thr
        35                  40                  45

Arg Arg Glu Asp Lys Phe Met Tyr Phe Glu Phe Pro Gln Pro Leu Pro
    50                  55                  60

Val Cys Gly Asp Ile Lys Val Glu Phe Phe His Lys Gln Asn Lys Met
65                  70                  75                  80

Leu Lys Lys Asp Lys Met Phe His Phe Trp Val Asn Thr Phe Phe Ile
                85                  90                  95

Pro Gly Pro Glu Glu Thr Ser Glu Lys Val Glu Asn Gly Ser Leu Cys
            100                 105                 110

Asp Gln Glu Ile Asp Ser Ile Cys Ser Ile Glu Arg Ala Asp Asn Asp
        115                 120                 125

Lys Glu Tyr Leu Val Leu Thr Leu Thr Lys Asn Asp Leu Asp Lys Ala
    130                 135                 140

Asn Lys Asp Lys Ala Asn Arg Tyr Phe Ser Pro Asn Phe Lys Val Lys
145                 150                 155                 160

Leu Tyr Phe Thr Lys Thr Val Glu Glu Pro Ser Asn Pro Glu Ala Ser
                165                 170                 175

Ser Ser Thr Ser Val Thr Pro Asp Val Ser Asp Asn Glu Pro Asp His
            180                 185                 190
```

Tyr Arg Tyr Ser Asp Thr Thr Asp Ser Asp Pro Glu Asn Glu Pro Phe
195                 200                 205

Asp Glu Asp Gln His Thr Gln Ile Thr Lys Val
210                 215

<210> SEQ ID NO 6
<211> LENGTH: 143
<212> TYPE: PRT
<213> ORGANISM: Homo sapiens

<400> SEQUENCE: 6

Ala Phe His Ala Gly Phe His Lys Val Cys Gly Gly Lys Val Leu Leu
1               5                   10                  15

Leu Phe Gln Pro Asn Glu Leu Gln Ala Met Val Ile Gly Asn Thr Asn
                20                  25                  30

Tyr Asp Trp Lys Glu Leu Glu Lys Asn Thr Glu Tyr Lys Gly Glu Tyr
            35                  40                  45

Trp Ala Glu His Pro Thr Ile Lys Ile Phe Trp Glu Val Phe His Glu
50                  55                  60

Leu Pro Leu Glu Lys Lys Lys Gln Phe Leu Leu Phe Leu Thr Gly Ser
65                  70                  75                  80

Asp Arg Ile Pro Ile Leu Gly Met Lys Ser Leu Lys Leu Val Ile Gln
                85                  90                  95

Ser Thr Gly Gly Gly Glu Glu Tyr Leu Pro Val Ser His Thr Cys Phe
                100                 105                 110

Asn Leu Leu Asp Leu Pro Lys Tyr Thr Glu Lys Glu Thr Leu Arg Ser
            115                 120                 125

Lys Leu Ile Gln Ala Ile Asp His Asn Glu Gly Phe Ser Leu Ile
        130                 135                 140

<210> SEQ ID NO 7
<211> LENGTH: 143
<212> TYPE: PRT
<213> ORGANISM: Homo sapiens

<400> SEQUENCE: 7

Ala Phe His Ala Gly Phe His Lys Val Cys Gly Gly Lys Val Leu Leu
1               5                   10                  15

Leu Phe Gln Pro Asn Glu Leu Gln Ala Met Val Ile Gly Asn Thr Asn
                20                  25                  30

Tyr Asp Trp Lys Glu Leu Glu Lys Asn Thr Glu Tyr Lys Gly Glu Tyr
            35                  40                  45

Trp Ala Glu His Pro Thr Ile Lys Ile Phe Trp Glu Val Phe His Glu
50                  55                  60

Leu Pro Leu Glu Lys Lys Lys Gln Phe Leu Leu Phe Leu Thr Gly Ser
65                  70                  75                  80

Asp Arg Ile Pro Ile Leu Gly Met Lys Ser Leu Lys Leu Val Ile Gln
                85                  90                  95

Ser Thr Gly Gly Gly Glu Glu Tyr Leu Pro Val Ser His Thr Cys Phe
                100                 105                 110

Asn Leu Leu Asp Leu Pro Lys Tyr Thr Glu Lys Glu Thr Leu Arg Ser
            115                 120                 125

Lys Leu Ile Gln Ala Ile Asp His Asn Glu Gly Phe Ser Leu Ile
        130                 135                 140

<210> SEQ ID NO 8
<211> LENGTH: 257
<212> TYPE: PRT

<213> ORGANISM: Homo sapiens

<400> SEQUENCE: 8

```
Leu Ile Val Lys Lys Glu Phe Val Lys Glu Asn Leu Val Lys Leu Leu
1               5                   10                  15

Asn Pro Arg Tyr Asn Leu Pro Leu Asp Ile Gln Asn Arg Ile Leu Asn
            20                  25                  30

Phe Ile Lys Thr Trp Ser Gln Gly Phe Pro Gly Gly Val Asp Val Ser
        35                  40                  45

Glu Val Lys Glu Val Tyr Leu Asp Leu Val Lys Lys Gly Val Gln Phe
    50                  55                  60

Pro Pro Ser Glu Ala Glu Ala Glu Thr Ala Arg Gln Glu Thr Ala Gln
65                  70                  75                  80

Ile Ser Ser Asn Pro Pro Thr Ser Val Pro Thr Ala Pro Ala Leu Ser
                85                  90                  95

Ser Val Ile Ala Pro Lys Asn Ser Thr Val Thr Leu Val Pro Glu Gln
            100                 105                 110

Ile Gly Lys Leu His Ser Glu Leu Asp Met Val Lys Met Asn Val Arg
        115                 120                 125

Val Met Ser Ala Ile Leu Met Glu Asn Thr Pro Gly Ser Glu Asn His
    130                 135                 140

Glu Asp Ile Glu Leu Leu Gln Lys Leu Tyr Lys Thr Gly Arg Glu Met
145                 150                 155                 160

Gln Glu Arg Ile Met Asp Leu Leu Val Val Glu Asn Glu Asp Val
                165                 170                 175

Thr Val Glu Leu Ile Gln Val Asn Glu Asp Leu Asn Asn Ala Ile Leu
            180                 185                 190

Gly Tyr Glu Arg Phe Thr Arg Asn Gln Gln Arg Ile Leu Glu Gln Asn
        195                 200                 205

Lys Asn Gln Lys Glu Ala Thr Asn Thr Thr Ser Glu Pro Ser Ala Pro
    210                 215                 220

Ser Gln Asp Leu Leu Asp Leu Ser Pro Ser Pro Arg Met Pro Arg Ala
225                 230                 235                 240

Thr Leu Gly Glu Leu Asn Thr Met Asn Asn Gln Leu Ser Gly Leu Ser
                245                 250                 255

Lys
```

<210> SEQ ID NO 9
<211> LENGTH: 407
<212> TYPE: PRT
<213> ORGANISM: Homo sapiens

<400> SEQUENCE: 9

```
Met Ser Gly Gly Ser Ala Asp Tyr Asn Arg Glu His Gly Gly Pro Glu
1               5                   10                  15

Gly Met Asp Pro Asp Gly Val Ile Glu Ser Asn Trp Asn Glu Ile Val
            20                  25                  30

Asp Asn Phe Asp Asp Met Asn Leu Lys Glu Ser Leu Leu Arg Gly Ile
        35                  40                  45

Tyr Ala Tyr Gly Phe Glu Lys Pro Ser Ala Ile Gln Gln Arg Ala Ile
    50                  55                  60

Ile Pro Cys Ile Lys Gly Tyr Asp Val Ile Ala Gln Ala Gln Ser Gly
65                  70                  75                  80

Thr Gly Lys Thr Ala Thr Phe Ala Ile Ser Ile Leu Gln Gln Leu Glu
                85                  90                  95
```

```
Ile Glu Phe Lys Glu Thr Gln Ala Leu Val Leu Ala Pro Thr Arg Glu
             100                 105                 110

Leu Ala Gln Gln Ile Gln Lys Val Ile Leu Ala Leu Gly Asp Tyr Met
         115                 120                 125

Gly Ala Thr Cys His Ala Cys Ile Gly Gly Thr Asn Val Arg Asn Glu
130                 135                 140

Met Gln Lys Leu Gln Ala Glu Ala Pro His Ile Val Val Gly Thr Pro
145                 150                 155                 160

Gly Arg Val Phe Asp Met Leu Asn Arg Arg Tyr Leu Ser Pro Lys Trp
                 165                 170                 175

Ile Lys Met Phe Val Leu Asp Glu Ala Asp Glu Met Leu Ser Arg Gly
             180                 185                 190

Phe Lys Asp Gln Ile Tyr Glu Ile Phe Gln Lys Leu Asn Thr Ser Ile
         195                 200                 205

Gln Val Val Leu Leu Ser Ala Thr Met Pro Thr Asp Val Leu Glu Val
210                 215                 220

Thr Lys Lys Phe Met Arg Asp Pro Ile Arg Ile Leu Val Lys Lys Glu
225                 230                 235                 240

Glu Leu Thr Leu Glu Gly Ile Lys Gln Phe Tyr Ile Asn Val Glu Arg
                 245                 250                 255

Glu Glu Trp Lys Leu Asp Thr Leu Cys Asp Leu Tyr Glu Thr Leu Thr
             260                 265                 270

Ile Thr Gln Ala Val Ile Phe Leu Asn Thr Arg Arg Lys Val Asp Trp
         275                 280                 285

Leu Thr Glu Lys Met His Ala Arg Asp Phe Thr Val Ser Ala Leu His
290                 295                 300

Gly Asp Met Asp Gln Lys Glu Arg Asp Val Ile Met Arg Glu Phe Arg
305                 310                 315                 320

Ser Gly Ser Ser Arg Val Leu Ile Thr Thr Asp Leu Leu Ala Arg Gly
                 325                 330                 335

Ile Asp Val Gln Gln Val Ser Leu Val Ile Asn Tyr Asp Leu Pro Thr
             340                 345                 350

Asn Arg Glu Asn Tyr Ile His Arg Ile Gly Arg Gly Gly Arg Phe Gly
         355                 360                 365

Arg Lys Gly Val Ala Ile Asn Phe Val Thr Glu Glu Asp Lys Arg Ile
370                 375                 380

Leu Arg Asp Ile Glu Thr Phe Tyr Asn Thr Thr Val Glu Glu Met Pro
385                 390                 395                 400

Met Asn Val Ala Asp Leu Ile
                 405

<210> SEQ ID NO 10
<211> LENGTH: 172
<212> TYPE: PRT
<213> ORGANISM: Homo sapiens

<400> SEQUENCE: 10

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
             20                  25                  30

Gly Lys Met Val Ser Arg Thr Glu Gly Asn Ile Asp Asp Ser Leu Ile
         35                  40                  45

Gly Gly Asn Ala Ser Ala Glu Gly Pro Glu Gly Glu Gly Thr Glu Ser
50                  55                  60
```

```
Thr Val Ile Thr Gly Val Asp Ile Val Met Asn His His Leu Gln Glu
 65                  70                  75                  80

Thr Ser Phe Thr Lys Glu Ala Tyr Lys Lys Tyr Ile Lys Asp Tyr Met
                 85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170
```

<210> SEQ ID NO 11
<211> LENGTH: 172
<212> TYPE: PRT
<213> ORGANISM: Homo sapiens

<400> SEQUENCE: 11

```
Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
                20                  25                  30

Gly Lys Met Val Ser Arg Thr Glu Gly Asn Ile Asp Asp Ser Leu Ile
            35                  40                  45

Gly Gly Asn Ala Ser Ala Glu Gly Pro Glu Gly Glu Gly Thr Glu Ser
        50                  55                  60

Thr Val Ile Thr Gly Val Asp Ile Val Met Asn His His Leu Gln Glu
 65                  70                  75                  80

Thr Ser Phe Thr Lys Glu Ala Tyr Lys Lys Tyr Ile Lys Asp Tyr Met
                 85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170
```

<210> SEQ ID NO 12
<211> LENGTH: 172
<212> TYPE: PRT
<213> ORGANISM: Homo sapiens

<400> SEQUENCE: 12

```
Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
                20                  25                  30

Gly Lys Met Val Ser Arg Thr Glu Gly Asn Ile Asp Asp Ser Leu Ile
            35                  40                  45

Gly Gly Asn Ala Ser Ala Glu Gly Pro Glu Gly Glu Gly Thr Glu Ser
```

```
                  50                  55                  60

Thr Val Ile Thr Gly Val Asp Ile Val Met Asn His His Leu Gln Glu
 65                  70                  75                  80

Thr Ser Phe Thr Lys Glu Ala Tyr Lys Lys Tyr Ile Lys Asp Tyr Met
                 85                  90                  95

Lys Ser Ile Lys Gly Lys Leu Glu Glu Gln Arg Pro Glu Arg Val Lys
                100                 105                 110

Pro Phe Met Thr Gly Ala Ala Glu Gln Ile Lys His Ile Leu Ala Asn
                115                 120                 125

Phe Lys Asn Tyr Gln Phe Phe Ile Gly Glu Asn Met Asn Pro Asp Gly
            130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170

<210> SEQ ID NO 13
<211> LENGTH: 172
<212> TYPE: PRT
<213> ORGANISM: Homo sapiens

<400> SEQUENCE: 13

Met Ile Ile Tyr Arg Asp Leu Ile Ser His Asp Glu Met Phe Ser Asp
  1               5                  10                  15

Ile Tyr Lys Ile Arg Glu Ile Ala Asp Gly Leu Cys Leu Glu Val Glu
                 20                  25                  30

Gly Lys Met Val Ser Arg Thr Glu Gly Asn Ile Asp Asp Ser Leu Ile
             35                  40                  45

Gly Gly Asn Ala Ser Ala Glu Gly Pro Glu Gly Glu Gly Thr Glu Ser
 50                  55                  60

Thr Val Ile Thr Gly Val Asp Ile Val Met Asn His His Leu Gln Glu
 65                  70                  75                  80

Thr Ser Phe Thr Lys Glu Ala Tyr Lys Lys Tyr Ile Lys Asp Tyr Met
                 85                  90                  95

Lys Ser Ile Lys Gly Lys Leu Glu Glu Gln Arg Pro Glu Arg Val Lys
                100                 105                 110

Pro Phe Met Thr Gly Ala Ala Glu Gln Ile Lys His Ile Leu Ala Asn
                115                 120                 125

Phe Lys Asn Tyr Gln Phe Phe Ile Gly Glu Asn Met Asn Pro Asp Gly
            130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170

<210> SEQ ID NO 14
<211> LENGTH: 45
<212> TYPE: PRT
<213> ORGANISM: Homo sapiens

<400> SEQUENCE: 14

Val Leu Ile Val Cys Val Pro Asn Pro Ile Asp Glu Lys Asn Ala
  1               5                  10                  15

Thr Met Pro Val Thr Met Leu Ile Arg Val Lys Thr Ser Glu Asp Ala
                 20                  25                  30

Asp Glu Leu His Lys Ile Leu Leu Glu Lys Lys Asp Ala
             35                  40                  45
```

<210> SEQ ID NO 15
<211> LENGTH: 168
<212> TYPE: PRT
<213> ORGANISM: Homo sapiens

<400> SEQUENCE: 15

Gln Ile Ile Thr Leu Gln Val Val Asn Met Glu Glu Gln Pro Ile Asn
1               5                   10                  15

Ile Gly Glu Leu Gln Leu Val Gln Val Pro Val Pro Val Thr Val Pro
            20                  25                  30

Val Ala Thr Thr Ser Val Glu Glu Leu Gln Gly Ala Tyr Glu Asn Glu
        35                  40                  45

Val Ser Lys Glu Gly Leu Ala Glu Ser Glu Pro Met Ile Cys His Thr
50                  55                  60

Leu Pro Leu Pro Glu Gly Phe Gln Val Val Lys Val Gly Ala Asn Gly
65                  70                  75                  80

Glu Val Glu Thr Leu Glu Gln Gly Glu Leu Pro Pro Gln Glu Asp Pro
                85                  90                  95

Ser Trp Gln Lys Asp Pro Asp Tyr Gln Pro Pro Ala Lys Lys Thr Lys
            100                 105                 110

Lys Thr Lys Lys Ser Lys Leu Arg Tyr Thr Glu Glu Gly Lys Asp Val
        115                 120                 125

Asp Val Ser Val Tyr Asp Phe Glu Glu Gln Gln Glu Gly Leu Leu
    130                 135                 140

Ser Glu Val Asn Ala Glu Lys Val Val Gly Asn Met Lys Pro Pro Lys
145                 150                 155                 160

Pro Thr Lys Ile Lys Lys Lys Gly
                165

<210> SEQ ID NO 16
<211> LENGTH: 162
<212> TYPE: PRT
<213> ORGANISM: Homo sapiens

<400> SEQUENCE: 16

Lys Leu Leu Glu Gln Tyr Lys Glu Glu Ser Lys Lys Ala Leu Pro Pro
1               5                   10                  15

Glu Lys Lys Gln Asn Thr Gly Ser Lys Ser Asn Lys Asn Lys Ser
            20                  25                  30

Gly Lys Asn Gln Phe Asn Arg Gly Gly His Arg Gly Arg Gly Gly
        35                  40                  45

Phe Asn Met Arg Gly Gly Asn Phe Arg Gly Ala Pro Gly Asn Arg
    50                  55                  60

Gly Gly Tyr Asn Arg Arg Gly Asn Met Pro Gln Arg Gly Gly Gly Gly
65                  70                  75                  80

Gly Gly Ser Gly Gly Ile Gly Tyr Pro Tyr Pro Arg Ala Pro Val Phe
                85                  90                  95

Pro Gly Arg Gly Ser Tyr Ser Asn Arg Gly Asn Tyr Asn Arg Gly Gly
            100                 105                 110

Met Pro Asn Arg Gly Asn Tyr Asn Gln Asn Phe Arg Gly Arg Gly Asn
        115                 120                 125

Asn Arg Gly Tyr Lys Asn Gln Ser Gln Gly Tyr Asn Gln Trp Gln Gln
    130                 135                 140

Gly Gln Phe Trp Gly Gln Lys Pro Trp Ser Gln His Tyr His Gln Gly
145                 150                 155                 160

Tyr Tyr

<210> SEQ ID NO 17
<211> LENGTH: 171
<212> TYPE: PRT
<213> ORGANISM: Homo sapiens

<400> SEQUENCE: 17

Met Ser Ser Lys Arg Thr Lys Thr Lys Lys Arg Pro Gln Arg
1               5                   10                  15

Ala Thr Ser Asn Val Phe Ala Met Phe Asp Gln Ser Gln Ile Gln Glu
                20                  25                  30

Phe Lys Glu Ala Phe Asn Met Ile Asp Gln Asn Arg Asp Gly Phe Ile
            35                  40                  45

Asp Lys Glu Asp Leu His Asp Met Leu Ala Ser Leu Gly Lys Asn Pro
50                      55                  60

Thr Asp Glu Tyr Leu Asp Ala Met Met Asn Glu Ala Pro Gly Pro Ile
65                  70                  75                  80

Asn Phe Thr Met Phe Leu Thr Met Phe Gly Glu Lys Leu Asn Gly Thr
                85                  90                  95

Asp Pro Glu Asp Val Ile Arg Asn Ala Phe Ala Cys Phe Asp Glu Glu
            100                 105                 110

Ala Thr Gly Thr Ile Gln Glu Asp Tyr Leu Arg Glu Leu Leu Thr Thr
        115                 120                 125

Met Gly Asp Arg Phe Thr Asp Glu Glu Val Asp Glu Leu Tyr Arg Glu
130                 135                 140

Ala Pro Ile Asp Lys Lys Gly Asn Phe Asn Tyr Ile Glu Phe Thr Arg
145                 150                 155                 160

Ile Leu Lys His Gly Ala Lys Asp Lys Asp
                165                 170

<210> SEQ ID NO 18
<211> LENGTH: 196
<212> TYPE: PRT
<213> ORGANISM: Homo sapiens

<400> SEQUENCE: 18

Glu Lys Tyr Lys Asp Gln Asp Glu Asp Arg Glu Leu Ile Met Lys
1               5                   10                  15

Leu Leu Gly Ser Ala Gly Ser Asn Lys Glu Glu Lys Gly Lys Lys Gly
                20                  25                  30

Lys Lys Gly Lys Thr Lys Asp Glu Pro Val Lys Lys Gln Pro Gln Lys
            35                  40                  45

Pro Arg Gly Gly Gln Arg Val Ser Asp Asn Ile Lys Lys Glu Thr Pro
50                      55                  60

Phe Leu Glu Val Ile Thr His Glu Leu Gln Asp Phe Ala Val Asp Asp
65                  70                  75                  80

Pro His Asp Asp Lys Glu Gln Asp Leu Asp Gln Gly Asn Glu
                85                  90                  95

Glu Asn Leu Phe Asp Ser Leu Thr Gly Gln Pro His Pro Glu Asp Val
            100                 105                 110

Leu Leu Phe Ala Ile Pro Ile Cys Ala Pro Tyr Thr Thr Met Thr Asn
        115                 120                 125

Tyr Lys Tyr Lys Val Lys Leu Thr Pro Gly Val Gln Lys Lys Gly Lys
130                 135                 140

Ala Ala Lys Thr Ala Leu Asn Ser Phe Met His Ser Lys Glu Ala Thr
145                 150                 155                 160

```
Ala Arg Glu Lys Asp Leu Phe Arg Ser Val Lys Asp Thr Asp Leu Ser
            165                 170                 175

Arg Asn Ile Pro Gly Lys Val Lys Val Ser Ala Pro Asn Leu Leu Asn
            180                 185                 190

Val Lys Arg Lys
        195

<210> SEQ ID NO 19
<211> LENGTH: 196
<212> TYPE: PRT
<213> ORGANISM: Homo sapiens

<400> SEQUENCE: 19

Glu Lys Tyr Lys Asp Gln Asp Glu Glu Asp Arg Glu Leu Ile Met Lys
1               5                   10                  15

Leu Leu Gly Ser Ala Gly Ser Asn Lys Glu Lys Gly Lys Lys Gly
            20                  25                  30

Lys Lys Gly Lys Thr Lys Asp Glu Pro Val Lys Lys Gln Pro Gln Lys
        35                  40                  45

Pro Arg Gly Gly Gln Arg Val Ser Asp Asn Ile Lys Lys Glu Thr Pro
    50                  55                  60

Phe Leu Glu Val Ile Thr His Glu Leu Gln Asp Phe Ala Val Asp Asp
65                  70                  75                  80

Pro His Asp Asp Lys Glu Gln Asp Leu Asp Gln Gly Asn Glu
                85                  90                  95

Glu Asn Leu Phe Asp Ser Leu Thr Gly Gln Pro His Pro Glu Asp Val
                100                 105                 110

Leu Leu Phe Ala Ile Pro Ile Cys Ala Pro Tyr Thr Thr Met Thr Asn
            115                 120                 125

Tyr Lys Tyr Lys Val Lys Leu Thr Pro Gly Val Gln Lys Lys Gly Lys
            130                 135                 140

Ala Ala Lys Thr Ala Leu Asn Ser Phe Met His Ser Lys Glu Ala Thr
145                 150                 155                 160

Ala Arg Glu Lys Asp Leu Phe Arg Ser Val Lys Asp Thr Asp Leu Ser
            165                 170                 175

Arg Asn Ile Pro Gly Lys Val Lys Val Ser Ala Pro Asn Leu Leu Asn
            180                 185                 190

Val Lys Arg Lys
        195

<210> SEQ ID NO 20
<211> LENGTH: 150
<212> TYPE: PRT
<213> ORGANISM: Homo sapiens

<400> SEQUENCE: 20

Arg Arg Asp Tyr Val Phe Ile Glu Phe Cys Val Glu Asp Ser Lys Asp
1               5                   10                  15

Val Asn Val Asn Phe Glu Lys Ser Lys Leu Thr Phe Ser Cys Leu Gly
            20                  25                  30

Gly Ser Asp Asn Phe Lys His Leu Asn Glu Ile Asp Leu Phe His Cys
            35                  40                  45

Ile Asp Pro Asn Asp Ser Lys His Lys Arg Thr Asp Arg Ser Ile Leu
        50                  55                  60

Cys Cys Leu Arg Lys Gly Glu Ser Gly Gln Ser Trp Pro Arg Leu Thr
65                  70                  75                  80
```

```
Lys Glu Arg Ala Lys Leu Asn Trp Leu Ser Val Asp Phe Asn Asn Trp
                85                  90                  95
Lys Asp Trp Glu Asp Asp Ser Asp Glu Asp Met Ser Asn Phe Asp Arg
               100                 105                 110
Phe Ser Glu Met Met Asn Asn Met Gly Gly Asp Glu Asp Val Asp Leu
           115                 120                 125
Pro Glu Val Asp Gly Ala Asp Asp Ser Gln Asp Ser Asp Asp Glu
       130                 135                 140
Lys Met Pro Asp Leu Glu
145                 150

<210> SEQ ID NO 21
<211> LENGTH: 724
<212> TYPE: PRT
<213> ORGANISM: Homo sapiens

<400> SEQUENCE: 21

Met Pro Glu Glu Val His His Gly Glu Glu Val Glu Thr Phe Ala
1               5                   10                  15
Phe Gln Ala Glu Ile Ala Gln Leu Met Ser Leu Ile Ile Asn Thr Phe
            20                  25                  30
Tyr Ser Asn Lys Glu Ile Phe Leu Arg Glu Leu Ile Ser Asn Ala Ser
        35                  40                  45
Asp Ala Leu Asp Lys Ile Arg Tyr Glu Ser Leu Thr Asp Pro Ser Lys
    50                  55                  60
Leu Asp Ser Gly Lys Glu Leu Lys Ile Asp Ile Ile Pro Asn Pro Gln
65                  70                  75                  80
Glu Arg Thr Leu Thr Leu Val Asp Thr Gly Ile Gly Met Thr Lys Ala
                85                  90                  95
Asp Leu Ile Asn Asn Leu Gly Thr Ile Ala Lys Ser Gly Thr Lys Ala
            100                 105                 110
Phe Met Glu Ala Leu Gln Ala Gly Ala Asp Ile Ser Met Ile Gly Gln
        115                 120                 125
Phe Gly Val Gly Phe Tyr Ser Ala Tyr Leu Val Ala Glu Lys Val Val
    130                 135                 140
Val Ile Thr Lys His Asn Asp Asp Glu Gln Tyr Ala Trp Glu Ser Ser
145                 150                 155                 160
Ala Gly Gly Ser Phe Thr Val Arg Ala Asp His Gly Glu Pro Ile Gly
                165                 170                 175
Arg Gly Thr Lys Val Ile Leu His Leu Lys Glu Asp Gln Thr Glu Tyr
            180                 185                 190
Leu Glu Glu Arg Arg Val Lys Glu Val Val Lys Lys His Ser Gln Phe
        195                 200                 205
Ile Gly Tyr Pro Ile Thr Leu Tyr Leu Glu Lys Glu Arg Glu Lys Glu
    210                 215                 220
Ile Ser Asp Asp Glu Ala Glu Glu Glu Lys Gly Glu Lys Glu Glu Glu
225                 230                 235                 240
Asp Lys Asp Asp Glu Glu Lys Pro Lys Ile Glu Asp Val Gly Ser Asp
                245                 250                 255
Glu Glu Asp Asp Ser Gly Lys Asp Lys Lys Lys Thr Lys Lys Ile
            260                 265                 270
Lys Glu Lys Tyr Ile Asp Gln Glu Glu Leu Asn Lys Thr Lys Pro Ile
        275                 280                 285
Trp Thr Arg Asn Pro Asp Asp Ile Thr Gln Glu Glu Tyr Gly Glu Phe
    290                 295                 300
```

```
Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
            325                 330                 335

Arg Arg Ala Pro Phe Asp Leu Phe Glu Asn Lys Lys Lys Asn
        340                 345                 350

Ile Lys Leu Tyr Val Arg Arg Val Phe Ile Met Asp Ser Cys Asp Glu
        355                 360                 365

Leu Ile Pro Glu Tyr Leu Asn Phe Ile Arg Gly Val Val Asp Ser Glu
370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
            405                 410                 415

Ser Glu Leu Ala Glu Asp Lys Glu Asn Tyr Lys Lys Phe Tyr Glu Ala
                420                 425                 430

Phe Ser Lys Asn Leu Lys Leu Gly Ile His Glu Asp Ser Thr Asn Arg
            435                 440                 445

Arg Arg Leu Ser Glu Leu Leu Arg Tyr His Thr Ser Gln Ser Gly Asp
450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
            500                 505                 510

Met Thr Glu Pro Ile Asp Glu Tyr Cys Val Gln Gln Leu Lys Glu Phe
            515                 520                 525

Asp Gly Lys Ser Leu Val Ser Val Thr Lys Glu Gly Leu Glu Leu Pro
530                 535                 540

Glu Asp Glu Glu Glu Lys Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
            580                 585                 590

Thr Ser Thr Tyr Gly Trp Thr Ala Asn Met Glu Arg Ile Met Lys Ala
            595                 600                 605

Gln Ala Leu Arg Asp Asn Ser Thr Met Gly Tyr Met Met Ala Lys Lys
    610                 615                 620

His Leu Glu Ile Asn Pro Asp His Pro Ile Val Glu Thr Leu Arg Gln
625                 630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
        675                 680                 685

Gly Ile Asp Glu Asp Glu Val Ala Ala Glu Glu Pro Asn Ala Ala Val
        690                 695                 700

Pro Asp Glu Ile Pro Pro Leu Glu Gly Asp Glu Asp Ala Ser Arg Met
705                 710                 715                 720

Glu Glu Val Asp
```

<210> SEQ ID NO 22
<211> LENGTH: 218
<212> TYPE: PRT
<213> ORGANISM: Homo sapiens

<400> SEQUENCE: 22

Gln Thr Gln Ile Phe Thr Thr Tyr Ser Asp Asn Gln Pro Gly Val Leu
1               5                   10                  15

Ile Gln Val Tyr Glu Gly Glu Arg Ala Met Thr Lys Asp Asn Asn Leu
            20                  25                  30

Leu Gly Arg Phe Glu Leu Ser Gly Ile Pro Pro Ala Pro Arg Gly Val
        35                  40                  45

Pro Gln Ile Glu Val Thr Phe Asp Ile Asp Ala Asn Gly Ile Leu Asn
    50                  55                  60

Val Thr Ala Thr Asp Lys Ser Thr Gly Lys Ala Asn Lys Ile Thr Ile
65                  70                  75                  80

Thr Asn Asp Lys Gly Arg Leu Ser Lys Glu Glu Ile Glu Arg Met Val
                85                  90                  95

Gln Glu Ala Glu Lys Tyr Lys Ala Glu Asp Glu Val Gln Arg Glu Arg
            100                 105                 110

Val Ser Ala Lys Asn Ala Leu Glu Ser Tyr Ala Phe Asn Met Lys Ser
        115                 120                 125

Ala Val Glu Asp Glu Gly Leu Lys Gly Lys Ile Ser Glu Ala Asp Lys
    130                 135                 140

Lys Lys Val Leu Asp Lys Cys Gln Glu Val Ile Ser Trp Leu Asp Ala
145                 150                 155                 160

Asn Thr Leu Ala Glu Lys Asp Glu Phe Glu His Lys Arg Lys Glu Leu
                165                 170                 175

Glu Gln Val Cys Asn Pro Ile Ile Ser Gly Leu Tyr Gln Gly Ala Gly
            180                 185                 190

Gly Pro Gly Pro Gly Gly Phe Gly Ala Gln Gly Pro Lys Gly Gly Ser
        195                 200                 205

Gly Ser Gly Pro Thr Ile Glu Glu Val Asp
    210                 215

<210> SEQ ID NO 23
<211> LENGTH: 198
<212> TYPE: PRT
<213> ORGANISM: Homo sapiens

<400> SEQUENCE: 23

Glu Gly Glu Arg Ala Met Thr Lys Asp Asn Asn Leu Leu Gly Arg Phe
1               5                   10                  15

Glu Leu Ser Gly Ile Pro Pro Ala Pro Arg Gly Val Pro Gln Ile Glu
            20                  25                  30

Val Thr Phe Asp Ile Asp Ala Asn Gly Ile Leu Asn Val Thr Ala Thr
        35                  40                  45

Asp Lys Ser Thr Gly Lys Ala Asn Lys Ile Thr Ile Thr Asn Asp Lys
    50                  55                  60

Gly Arg Leu Ser Lys Glu Glu Ile Glu Arg Met Val Gln Glu Ala Glu
65                  70                  75                  80

Lys Tyr Lys Ala Glu Asp Glu Val Gln Arg Glu Arg Val Ser Ala Lys
                85                  90                  95

Asn Ala Leu Glu Ser Tyr Ala Phe Asn Met Lys Ser Ala Val Glu Asp
            100                 105                 110

Glu Gly Leu Lys Gly Lys Ile Ser Glu Ala Asp Lys Lys Lys Val Leu

```
                   115                 120                 125
Asp Lys Cys Gln Glu Val Ile Ser Trp Leu Asp Ala Asn Thr Leu Ala
    130                 135                 140

Glu Lys Asp Glu Phe Glu His Lys Arg Lys Glu Leu Glu Gln Val Cys
145                 150                 155                 160

Asn Pro Ile Ile Ser Gly Leu Tyr Gln Gly Ala Gly Pro Gly Pro
                165                 170                 175

Gly Gly Phe Gly Ala Gln Gly Pro Lys Gly Ser Ser Gly Pro
            180                 185                 190

Thr Ile Glu Glu Val Asp
        195

<210> SEQ ID NO 24
<211> LENGTH: 190
<212> TYPE: PRT
<213> ORGANISM: Homo sapiens

<400> SEQUENCE: 24

Asp Asn Asn Leu Leu Gly Arg Phe Glu Leu Ser Gly Ile Pro Pro Ala
1               5                   10                  15

Pro Arg Gly Val Pro Gln Ile Glu Val Thr Phe Asp Ile Asp Ala Asn
            20                  25                  30

Gly Ile Leu Asn Val Thr Ala Thr Asp Lys Ser Thr Gly Lys Ala Asn
        35                  40                  45

Lys Ile Thr Ile Thr Asn Asp Lys Gly Arg Leu Ser Lys Glu Glu Ile
    50                  55                  60

Glu Arg Met Val Gln Glu Ala Glu Lys Tyr Lys Ala Glu Asp Glu Val
65                  70                  75                  80

Gln Arg Glu Arg Val Ser Ala Lys Asn Ala Leu Glu Ser Tyr Ala Phe
                85                  90                  95

Asn Met Lys Ser Ala Val Glu Asp Glu Gly Leu Lys Gly Lys Ile Ser
            100                 105                 110

Glu Ala Asp Lys Lys Lys Val Leu Asp Lys Cys Gln Glu Val Ile Ser
        115                 120                 125

Trp Leu Asp Ala Asn Thr Leu Ala Glu Lys Asp Glu Phe Glu His Lys
    130                 135                 140

Arg Lys Glu Leu Glu Gln Val Cys Asn Pro Ile Ile Ser Gly Leu Tyr
145                 150                 155                 160

Gln Gly Ala Gly Gly Pro Gly Pro Gly Gly Phe Gly Ala Gln Gly Pro
                165                 170                 175

Lys Gly Gly Ser Gly Ser Gly Pro Thr Ile Glu Glu Val Asp
            180                 185                 190

<210> SEQ ID NO 25
<211> LENGTH: 197
<212> TYPE: PRT
<213> ORGANISM: Homo sapiens

<400> SEQUENCE: 25

Gly Glu Arg Ala Met Thr Lys Asp Asn Asn Leu Leu Gly Arg Phe Glu
1               5                   10                  15

Leu Ser Gly Ile Pro Pro Ala Pro Arg Gly Val Pro Gln Ile Glu Val
            20                  25                  30

Thr Phe Asp Ile Asp Ala Asn Gly Ile Leu Asn Val Thr Ala Thr Asp
        35                  40                  45

Lys Ser Thr Gly Lys Ala Asn Lys Ile Thr Ile Thr Asn Asp Lys Gly
    50                  55                  60
```

```
Arg Leu Ser Lys Glu Glu Ile Glu Arg Met Val Gln Glu Ala Glu Lys
 65                  70                  75                  80

Tyr Lys Ala Glu Asp Glu Val Gln Arg Glu Arg Val Ser Ala Lys Asn
                 85                  90                  95

Ala Leu Glu Ser Tyr Ala Phe Asn Met Lys Ser Ala Val Glu Asp Glu
            100                 105                 110

Gly Leu Lys Gly Lys Ile Ser Glu Ala Asp Lys Lys Val Leu Asp
            115                 120                 125

Lys Cys Gln Glu Val Ile Ser Trp Leu Asp Ala Asn Thr Leu Ala Glu
130                 135                 140

Lys Asp Glu Phe Glu His Lys Arg Lys Glu Leu Gln Val Cys Asn
145                 150                 155                 160

Pro Ile Ile Ser Gly Leu Tyr Gln Gly Ala Gly Gly Pro Gly Pro Gly
                165                 170                 175

Gly Phe Gly Ala Gln Gly Pro Lys Gly Gly Ser Gly Ser Gly Pro Thr
            180                 185                 190

Ile Glu Glu Val Asp
        195

<210> SEQ ID NO 26
<211> LENGTH: 218
<212> TYPE: PRT
<213> ORGANISM: Homo sapiens

<400> SEQUENCE: 26

Gln Thr Gln Ile Phe Thr Thr Tyr Ser Asp Asn Gln Pro Gly Val Leu
  1               5                  10                  15

Ile Gln Val Tyr Glu Gly Glu Arg Ala Met Thr Lys Asp Asn Asn Leu
             20                  25                  30

Leu Gly Arg Phe Glu Leu Ser Gly Ile Pro Pro Ala Pro Arg Gly Val
         35                  40                  45

Pro Gln Ile Glu Val Thr Phe Asp Ile Asp Ala Asn Gly Ile Leu Asn
 50                  55                  60

Val Thr Ala Thr Asp Lys Ser Thr Gly Lys Ala Asn Lys Ile Thr Ile
 65                  70                  75                  80

Thr Asn Asp Lys Gly Arg Leu Ser Lys Glu Glu Ile Glu Arg Met Val
                 85                  90                  95

Gln Glu Ala Glu Lys Tyr Lys Ala Glu Asp Glu Val Gln Arg Glu Arg
            100                 105                 110

Val Ser Ala Lys Asn Ala Leu Glu Ser Tyr Ala Phe Asn Met Lys Ser
        115                 120                 125

Ala Val Glu Asp Glu Gly Leu Lys Gly Lys Ile Ser Glu Ala Asp Lys
130                 135                 140

Lys Lys Val Leu Asp Lys Cys Gln Glu Val Ile Ser Trp Leu Asp Ala
145                 150                 155                 160

Asn Thr Leu Ala Glu Lys Asp Glu Phe Glu His Lys Arg Lys Glu Leu
                165                 170                 175

Glu Gln Val Cys Asn Pro Ile Ile Ser Gly Leu Tyr Gln Gly Ala Gly
            180                 185                 190

Gly Pro Gly Pro Gly Gly Phe Gly Ala Gln Gly Pro Lys Gly Gly Ser
        195                 200                 205

Gly Ser Gly Pro Thr Ile Glu Glu Val Asp
210                 215

<210> SEQ ID NO 27
```

```
<211> LENGTH: 223
<212> TYPE: PRT
<213> ORGANISM: Homo sapiens

<400> SEQUENCE: 27

Thr Ile Pro Thr Lys Gln Thr Gln Ile Phe Thr Thr Tyr Ser Asp Asn
1               5                   10                  15

Gln Pro Gly Val Leu Ile Gln Val Tyr Glu Gly Glu Arg Ala Met Thr
            20                  25                  30

Lys Asp Asn Asn Leu Leu Gly Arg Phe Glu Leu Ser Gly Ile Pro Pro
        35                  40                  45

Ala Pro Arg Gly Val Pro Gln Ile Glu Val Thr Phe Asp Ile Asp Ala
    50                  55                  60

Asn Gly Ile Leu Asn Val Thr Ala Thr Asp Lys Ser Thr Gly Lys Ala
65                  70                  75                  80

Asn Lys Ile Thr Ile Thr Asn Asp Lys Gly Arg Leu Ser Lys Glu Glu
                85                  90                  95

Ile Glu Arg Met Val Gln Glu Ala Glu Lys Tyr Lys Ala Glu Asp Glu
            100                 105                 110

Val Gln Arg Glu Arg Val Ser Ala Lys Asn Ala Leu Glu Ser Tyr Ala
        115                 120                 125

Phe Asn Met Lys Ser Ala Val Glu Asp Glu Gly Leu Lys Gly Lys Ile
    130                 135                 140

Ser Glu Ala Asp Lys Lys Lys Val Leu Asp Lys Cys Gln Glu Val Ile
145                 150                 155                 160

Ser Trp Leu Asp Ala Asn Thr Leu Ala Glu Lys Asp Glu Phe Glu His
                165                 170                 175

Lys Arg Lys Glu Leu Glu Gln Val Cys Asn Pro Ile Ile Ser Gly Leu
            180                 185                 190

Tyr Gln Gly Ala Gly Gly Pro Gly Pro Gly Gly Phe Gly Ala Gln Gly
        195                 200                 205

Pro Lys Gly Gly Ser Gly Ser Gly Pro Thr Ile Glu Glu Val Asp
    210                 215                 220

<210> SEQ ID NO 28
<211> LENGTH: 218
<212> TYPE: PRT
<213> ORGANISM: Homo sapiens

<400> SEQUENCE: 28

Gln Thr Gln Ile Phe Thr Thr Tyr Ser Asp Asn Gln Pro Gly Val Leu
1               5                   10                  15

Ile Gln Val Tyr Glu Gly Glu Arg Ala Met Thr Lys Asp Asn Asn Leu
            20                  25                  30

Leu Gly Arg Phe Glu Leu Ser Gly Ile Pro Pro Ala Pro Arg Gly Val
        35                  40                  45

Pro Gln Ile Glu Val Thr Phe Asp Ile Asp Ala Asn Gly Ile Leu Asn
    50                  55                  60

Val Thr Ala Thr Asp Lys Ser Thr Gly Lys Ala Asn Lys Ile Thr Ile
65                  70                  75                  80

Thr Asn Asp Lys Gly Arg Leu Ser Lys Glu Glu Ile Glu Arg Met Val
                85                  90                  95

Gln Glu Ala Glu Lys Tyr Lys Ala Glu Asp Glu Val Gln Arg Glu Arg
            100                 105                 110

Val Ser Ala Lys Asn Ala Leu Glu Ser Tyr Ala Phe Asn Met Lys Ser
        115                 120                 125
```

```
Ala Val Glu Asp Glu Gly Leu Lys Gly Lys Ile Ser Glu Ala Asp Lys
            130                 135                 140

Lys Lys Val Leu Asp Lys Cys Gln Glu Val Ile Ser Trp Leu Asp Ala
145                 150                 155                 160

Asn Thr Leu Ala Glu Lys Asp Glu Phe Glu His Lys Arg Lys Glu Leu
                165                 170                 175

Glu Gln Val Cys Asn Pro Ile Ile Ser Gly Leu Tyr Gln Gly Ala Gly
            180                 185                 190

Gly Pro Gly Pro Gly Gly Phe Gly Ala Gln Gly Pro Lys Gly Gly Ser
        195                 200                 205

Gly Ser Gly Pro Thr Ile Glu Glu Val Asp
    210                 215

<210> SEQ ID NO 29
<211> LENGTH: 215
<212> TYPE: PRT
<213> ORGANISM: Homo sapiens

<400> SEQUENCE: 29

Asn Thr Val Val Pro Thr Lys Lys Ser Gln Ile Phe Ser Thr Ala Ser
1               5                   10                  15

Asp Asn Gln Pro Thr Val Thr Ile Lys Val Tyr Glu Gly Glu Arg Pro
            20                  25                  30

Leu Thr Lys Asp Asn His Leu Leu Gly Thr Phe Asp Leu Thr Gly Ile
        35                  40                  45

Pro Pro Ala Pro Arg Gly Val Pro Gln Ile Glu Val Thr Phe Glu Ile
    50                  55                  60

Asp Val Asn Gly Ile Leu Arg Val Thr Ala Glu Asp Lys Gly Thr Gly
65                  70                  75                  80

Asn Lys Asn Lys Ile Thr Ile Thr Asn Asp Gln Asn Arg Leu Thr Pro
                85                  90                  95

Glu Glu Ile Glu Arg Met Val Asn Asp Ala Glu Lys Phe Ala Glu Glu
            100                 105                 110

Asp Lys Lys Leu Lys Glu Arg Ile Asp Thr Arg Asn Glu Leu Glu Ser
        115                 120                 125

Tyr Ala Tyr Ser Leu Lys Asn Gln Ile Gly Asp Lys Glu Lys Leu Gly
    130                 135                 140

Gly Lys Leu Ser Ser Glu Asp Lys Glu Thr Met Glu Lys Ala Val Glu
145                 150                 155                 160

Glu Lys Ile Glu Trp Leu Glu Ser His Gln Asp Ala Asp Ile Glu Asp
                165                 170                 175

Phe Lys Ala Lys Lys Lys Glu Leu Glu Glu Ile Val Gln Pro Ile Ile
            180                 185                 190

Ser Lys Leu Tyr Gly Ser Ala Gly Pro Pro Pro Thr Gly Glu Glu Asp
        195                 200                 205

Thr Ala Glu Lys Asp Glu Leu
    210                 215

<210> SEQ ID NO 30
<211> LENGTH: 215
<212> TYPE: PRT
<213> ORGANISM: Homo sapiens

<400> SEQUENCE: 30

Asn Thr Val Val Pro Thr Lys Lys Ser Gln Ile Phe Ser Thr Ala Ser
1               5                   10                  15

Asp Asn Gln Pro Thr Val Thr Ile Lys Val Tyr Glu Gly Glu Arg Pro
            20                  25                  30
```

```
                    20                  25                  30
Leu Thr Lys Asp Asn His Leu Leu Gly Thr Phe Asp Leu Thr Gly Ile
            35                  40                  45

Pro Pro Ala Pro Arg Gly Val Pro Gln Ile Glu Val Thr Phe Glu Ile
        50                  55                  60

Asp Val Asn Gly Ile Leu Arg Val Thr Ala Glu Asp Lys Gly Thr Gly
65                  70                  75                  80

Asn Lys Asn Lys Ile Thr Ile Thr Asn Asp Gln Asn Arg Leu Thr Pro
                85                  90                  95

Glu Glu Ile Glu Arg Met Val Asn Asp Ala Glu Lys Phe Ala Glu Glu
            100                 105                 110

Asp Lys Lys Leu Lys Glu Arg Ile Asp Thr Arg Asn Glu Leu Glu Ser
        115                 120                 125

Tyr Ala Tyr Ser Leu Lys Asn Gln Ile Gly Asp Lys Glu Lys Leu Gly
    130                 135                 140

Gly Lys Leu Ser Ser Glu Asp Lys Glu Thr Met Glu Lys Ala Val Glu
145                 150                 155                 160

Glu Lys Ile Glu Trp Leu Glu Ser His Gln Asp Ala Asp Ile Glu Asp
                165                 170                 175

Phe Lys Ala Lys Lys Lys Glu Leu Glu Glu Ile Val Gln Pro Ile Ile
            180                 185                 190

Ser Lys Leu Tyr Gly Ser Ala Gly Pro Pro Pro Thr Gly Glu Glu Asp
        195                 200                 205

Thr Ala Glu Lys Asp Glu Leu
    210                 215

<210> SEQ ID NO 31
<211> LENGTH: 215
<212> TYPE: PRT
<213> ORGANISM: Homo sapiens

<400> SEQUENCE: 31

Asn Thr Val Val Pro Thr Lys Lys Ser Gln Ile Phe Ser Thr Ala Ser
1               5                   10                  15

Asp Asn Gln Pro Thr Val Thr Ile Lys Val Tyr Glu Gly Glu Arg Pro
            20                  25                  30

Leu Thr Lys Asp Asn His Leu Leu Gly Thr Phe Asp Leu Thr Gly Ile
        35                  40                  45

Pro Pro Ala Pro Arg Gly Val Pro Gln Ile Glu Val Thr Phe Glu Ile
    50                  55                  60

Asp Val Asn Gly Ile Leu Arg Val Thr Ala Glu Asp Lys Gly Thr Gly
65                  70                  75                  80

Asn Lys Asn Lys Ile Thr Ile Thr Asn Asp Gln Asn Arg Leu Thr Pro
                85                  90                  95

Glu Glu Ile Glu Arg Met Val Asn Asp Ala Glu Lys Phe Ala Glu Glu
            100                 105                 110

Asp Lys Lys Leu Lys Glu Arg Ile Asp Thr Arg Asn Glu Leu Glu Ser
        115                 120                 125

Tyr Ala Tyr Ser Leu Lys Asn Gln Ile Gly Asp Lys Glu Lys Leu Gly
    130                 135                 140

Gly Lys Leu Ser Ser Glu Asp Lys Glu Thr Met Glu Lys Ala Val Glu
145                 150                 155                 160

Glu Lys Ile Glu Trp Leu Glu Ser His Gln Asp Ala Asp Ile Glu Asp
                165                 170                 175

Phe Lys Ala Lys Lys Lys Glu Leu Glu Glu Ile Val Gln Pro Ile Ile
```

```
                    180                 185                 190
Ser Lys Leu Tyr Gly Ser Ala Gly Pro Pro Thr Gly Glu Glu Asp
        195                 200                 205

Thr Ala Glu Lys Asp Glu Leu
        210                 215

<210> SEQ ID NO 32
<211> LENGTH: 234
<212> TYPE: PRT
<213> ORGANISM: Homo sapiens

<400> SEQUENCE: 32

Leu Ile Lys Arg Asn Thr Thr Ile Pro Thr Lys Gln Thr Gln Thr Phe
1               5                   10                  15

Thr Thr Tyr Ser Asp Asn Gln Pro Gly Val Leu Ile Gln Val Tyr Glu
            20                  25                  30

Gly Glu Arg Ala Met Thr Lys Asp Asn Asn Leu Leu Gly Lys Phe Glu
        35                  40                  45

Leu Thr Gly Ile Pro Pro Ala Pro Arg Gly Val Pro Gln Ile Glu Val
    50                  55                  60

Thr Phe Asp Ile Asp Ala Asn Gly Ile Leu Asn Val Ser Ala Val Asp
65                  70                  75                  80

Lys Ser Thr Gly Lys Glu Asn Lys Ile Thr Ile Thr Asn Asp Lys Gly
                85                  90                  95

Arg Leu Ser Lys Glu Asp Ile Glu Arg Met Val Gln Glu Ala Glu Lys
            100                 105                 110

Tyr Lys Ala Glu Asp Glu Lys Gln Arg Asp Lys Val Ser Ser Lys Asn
        115                 120                 125

Ser Leu Glu Ser Tyr Ala Phe Asn Met Lys Ala Thr Val Glu Asp Glu
    130                 135                 140

Lys Leu Gln Gly Lys Ile Asn Asp Glu Asp Lys Gln Lys Ile Leu Asp
145                 150                 155                 160

Lys Cys Asn Glu Ile Ile Asn Trp Leu Asp Lys Asn Gln Thr Ala Glu
                165                 170                 175

Lys Glu Glu Phe Glu His Gln Gln Lys Glu Leu Glu Lys Val Cys Asn
            180                 185                 190

Pro Ile Ile Thr Lys Leu Tyr Gln Ser Ala Gly Gly Met Pro Gly Gly
        195                 200                 205

Met Pro Gly Gly Phe Pro Gly Gly Ala Pro Pro Ser Gly Gly Ala
    210                 215                 220

Ser Ser Gly Pro Thr Ile Glu Glu Val Asp
225                 230

<210> SEQ ID NO 33
<211> LENGTH: 183
<212> TYPE: PRT
<213> ORGANISM: Homo sapiens

<400> SEQUENCE: 33

Ile Pro Pro Ala Pro Arg Gly Val Pro Gln Ile Glu Val Thr Phe Asp
1               5                   10                  15

Ile Asp Ala Asn Gly Ile Leu Asn Val Ser Ala Val Asp Lys Ser Thr
            20                  25                  30

Gly Lys Glu Asn Lys Ile Thr Ile Thr Asn Asp Lys Gly Arg Leu Ser
        35                  40                  45

Lys Glu Asp Ile Glu Arg Met Val Gln Glu Ala Glu Lys Tyr Lys Ala
    50                  55                  60
```

Glu Asp Glu Lys Gln Arg Asp Lys Val Ser Ser Lys Asn Ser Leu Glu
65                  70                  75                  80

Ser Tyr Ala Phe Asn Met Lys Ala Thr Val Glu Asp Glu Lys Leu Gln
                85                  90                  95

Gly Lys Ile Asn Asp Glu Asp Lys Gln Lys Ile Leu Asp Lys Cys Asn
            100                 105                 110

Glu Ile Ile Asn Trp Leu Asp Lys Asn Gln Thr Ala Glu Lys Glu Glu
                115                 120                 125

Phe Glu His Gln Gln Lys Glu Leu Glu Lys Val Cys Asn Pro Ile Ile
130                 135                 140

Thr Lys Leu Tyr Gln Ser Ala Gly Gly Met Pro Gly Gly Met Pro Gly
145                 150                 155                 160

Gly Phe Pro Gly Gly Ala Pro Pro Ser Gly Gly Ala Ser Ser Gly
                165                 170                 175

Pro Thr Ile Glu Glu Val Asp
            180

<210> SEQ ID NO 34
<211> LENGTH: 221
<212> TYPE: PRT
<213> ORGANISM: Homo sapiens

<400> SEQUENCE: 34

Gln Thr Phe Thr Thr Tyr Ser Asp Asn Gln Pro Gly Val Leu Ile Gln
1               5                   10                  15

Val Tyr Glu Gly Glu Arg Ala Met Thr Lys Asp Asn Asn Leu Leu Gly
            20                  25                  30

Lys Phe Glu Leu Thr Gly Ile Pro Pro Ala Pro Arg Gly Val Pro Gln
        35                  40                  45

Ile Glu Val Thr Phe Asp Ile Asp Ala Asn Gly Ile Leu Asn Val Ser
    50                  55                  60

Ala Val Asp Lys Ser Thr Gly Lys Glu Asn Lys Ile Thr Ile Thr Asn
65                  70                  75                  80

Asp Lys Gly Arg Leu Ser Lys Glu Asp Ile Glu Arg Met Val Gln Glu
                85                  90                  95

Ala Glu Lys Tyr Lys Ala Glu Asp Glu Lys Gln Arg Asp Lys Val Ser
            100                 105                 110

Ser Lys Asn Ser Leu Glu Ser Tyr Ala Phe Asn Met Lys Ala Thr Val
        115                 120                 125

Glu Asp Glu Lys Leu Gln Gly Lys Ile Asn Asp Glu Asp Lys Gln Lys
130                 135                 140

Ile Leu Asp Lys Cys Asn Glu Ile Ile Asn Trp Leu Asp Lys Asn Gln
145                 150                 155                 160

Thr Ala Glu Lys Glu Glu Phe Glu His Gln Gln Lys Glu Leu Glu Lys
                165                 170                 175

Val Cys Asn Pro Ile Ile Thr Lys Leu Tyr Gln Ser Ala Gly Gly Met
            180                 185                 190

Pro Gly Gly Met Pro Gly Gly Phe Pro Gly Gly Ala Pro Pro Ser
        195                 200                 205

Gly Gly Ala Ser Ser Gly Pro Thr Ile Glu Glu Val Asp
    210                 215                 220

<210> SEQ ID NO 35
<211> LENGTH: 378
<212> TYPE: PRT
<213> ORGANISM: Homo sapiens

<400> SEQUENCE: 35

```
Lys Val Arg Val Asn Thr His Gly Ile Phe Thr Ile Ser Thr Ala Ser
1               5                   10                  15
Met Val Glu Lys Val Pro Thr Glu Glu Asn Glu Met Ser Ser Glu Ala
            20                  25                  30
Asp Met Glu Cys Leu Asn Gln Arg Pro Pro Glu Asn Pro Asp Thr Asp
        35                  40                  45
Lys Asn Val Gln Gln Asp Asn Ser Glu Ala Gly Thr Gln Pro Gln Val
    50                  55                  60
Gln Thr Asp Ala Gln Gln Thr Ser Gln Ser Pro Ser Pro Ser Glu Leu
65                  70                  75                  80
Thr Ser Glu Glu Asn Lys Ile Pro Asp Ala Asp Lys Ala Asn Glu Lys
                85                  90                  95
Lys Val Asp Gln Pro Pro Glu Ala Lys Lys Pro Lys Ile Lys Val Val
            100                 105                 110
Asn Val Glu Leu Pro Ile Glu Ala Asn Leu Val Trp Gln Leu Gly Lys
        115                 120                 125
Asp Leu Leu Asn Met Tyr Ile Glu Thr Glu Gly Lys Met Ile Met Gln
    130                 135                 140
Asp Lys Leu Glu Lys Glu Arg Asn Asp Ala Lys Asn Ala Val Glu Glu
145                 150                 155                 160
Tyr Val Tyr Glu Phe Arg Asp Lys Leu Cys Gly Pro Tyr Glu Lys Phe
                165                 170                 175
Ile Cys Glu Gln Asp His Gln Asn Phe Leu Arg Leu Leu Thr Glu Thr
            180                 185                 190
Glu Asp Trp Leu Tyr Glu Glu Gly Glu Asp Gln Ala Lys Gln Ala Tyr
        195                 200                 205
Val Asp Lys Leu Glu Glu Leu Met Lys Ile Gly Thr Pro Val Lys Val
    210                 215                 220
Arg Phe Gln Glu Ala Glu Glu Arg Pro Lys Met Phe Glu Glu Leu Gly
225                 230                 235                 240
Gln Arg Leu Gln His Tyr Ala Lys Ile Ala Ala Asp Phe Arg Asn Lys
                245                 250                 255
Asp Glu Lys Tyr Asn His Ile Asp Glu Ser Glu Met Lys Lys Val Glu
            260                 265                 270
Lys Ser Val Asn Glu Val Met Glu Trp Met Asn Asn Val Met Asn Ala
        275                 280                 285
Gln Ala Lys Lys Ser Leu Asp Gln Asp Pro Val Val Arg Ala Gln Glu
    290                 295                 300
Ile Lys Thr Lys Ile Lys Glu Leu Asn Asn Thr Cys Glu Pro Val Val
305                 310                 315                 320
Thr Gln Pro Lys Pro Lys Ile Glu Ser Pro Lys Leu Glu Arg Thr Pro
                325                 330                 335
Asn Gly Pro Asn Ile Asp Lys Lys Glu Glu Asp Leu Glu Asp Lys Asn
            340                 345                 350
Asn Phe Gly Ala Glu Pro His Gln Asn Gly Glu Cys Tyr Pro Asn
            355                 360                 365
Glu Lys Asn Ser Val Asn Met Asp Leu Asp
    370                 375
```

<210> SEQ ID NO 36
<211> LENGTH: 431
<212> TYPE: PRT
<213> ORGANISM: Homo sapiens

<400> SEQUENCE: 36

```
Arg Asp Val Arg Met Phe Phe His Phe Ser Glu Ile Leu Asp Gly Asn
1               5                   10                  15
Gln Leu His Ile Ala Asp Glu Val Glu Phe Thr Val Val Pro Asp Met
            20                  25                  30
Leu Ser Ala Gln Arg Asn His Ala Ile Arg Ile Lys Lys Leu Pro Lys
        35                  40                  45
Gly Thr Val Ser Phe His Ser His Ser Asp His Arg Phe Leu Gly Thr
    50                  55                  60
Val Glu Lys Glu Ala Thr Phe Ser Asn Pro Lys Thr Thr Ser Pro Asn
65                  70                  75                  80
Lys Gly Lys Glu Lys Glu Ala Glu Asp Gly Ile Ile Ala Tyr Asp Asp
                85                  90                  95
Cys Gly Val Lys Leu Thr Ile Ala Phe Gln Ala Lys Asp Val Glu Gly
            100                 105                 110
Ser Thr Ser Pro Gln Ile Gly Asp Lys Val Glu Phe Ser Ile Ser Asp
        115                 120                 125
Lys Gln Arg Pro Gly Gln Val Ala Thr Cys Val Arg Leu Leu Gly
    130                 135                 140
Arg Asn Ser Asn Ser Lys Arg Leu Leu Gly Tyr Val Ala Thr Leu Lys
145                 150                 155                 160
Asp Asn Phe Gly Phe Ile Glu Thr Ala Asn His Asp Lys Glu Ile Phe
                165                 170                 175
Phe His Tyr Ser Glu Phe Ser Gly Asp Val Asp Ser Leu Glu Leu Gly
            180                 185                 190
Asp Met Val Glu Tyr Ser Leu Ser Lys Gly Lys Gly Asn Lys Val Ser
        195                 200                 205
Ala Glu Lys Val Asn Lys Thr His Ser Val Asn Gly Ile Thr Glu Glu
    210                 215                 220
Ala Asp Pro Thr Ile Tyr Ser Gly Lys Val Ile Arg Pro Leu Arg Ser
225                 230                 235                 240
Val Asp Pro Thr Gln Thr Glu Tyr Gln Gly Met Ile Glu Ile Val Glu
                245                 250                 255
Glu Gly Asp Met Lys Gly Glu Val Tyr Pro Phe Gly Ile Val Gly Met
            260                 265                 270
Ala Asn Lys Gly Asp Cys Leu Gln Lys Gly Glu Ser Val Lys Phe Gln
        275                 280                 285
Leu Cys Val Leu Gly Gln Asn Ala Gln Thr Met Ala Tyr Asn Ile Thr
    290                 295                 300
Pro Leu Arg Arg Ala Thr Val Glu Cys Val Lys Asp Gln Phe Gly Phe
305                 310                 315                 320
Ile Asn Tyr Glu Val Gly Asp Ser Lys Lys Leu Phe Phe His Val Lys
                325                 330                 335
Glu Val Gln Asp Gly Ile Glu Leu Gln Ala Gly Asp Glu Val Glu Phe
            340                 345                 350
Ser Val Ile Leu Asn Gln Arg Thr Gly Lys Cys Ser Ala Cys Asn Val
        355                 360                 365
Trp Arg Val Cys Glu Gly Pro Lys Ala Val Ala Ala Pro Arg Pro Asp
    370                 375                 380
Arg Leu Val Asn Arg Leu Lys Asn Ile Thr Leu Asp Asp Ala Ser Ala
385                 390                 395                 400
Pro Arg Leu Met Val Leu Arg Gln Pro Arg Gly Pro Asn Ser Met
                405                 410                 415
```

Gly Phe Gly Ala Glu Arg Lys Ile Arg Gln Ala Gly Val Ile Asp
            420                 425                 430

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttttcggacc ggaaaacaga tggcaggtga tg                                    32

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aaatatgcgg ccgcctatct ggggcttgtt ccatctg                               37

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgcggatcca ccatggaaaa cagatggcag gtgatg                                36

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccgctcgagc tagtgaccat tcattgtatg                                       30

<210> SEQ ID NO 41
<211> LENGTH: 336
<212> TYPE: PRT
<213> ORGANISM: Homo sapiens

<400> SEQUENCE: 41

Gly Ile Ala Tyr Val Glu Phe Val Asp Val Ser Ser Val Pro Leu Ala
1               5                   10                  15

Ile Gly Leu Thr Gly Gln Arg Val Leu Gly Val Pro Ile Ile Val Gln
            20                  25                  30

Ala Ser Gln Ala Glu Lys Asn Arg Ala Ala Met Ala Asn Asn Leu
        35                  40                  45

Gln Lys Gly Ser Ala Gly Pro Met Arg Leu Tyr Val Gly Ser Leu His
    50                  55                  60

Phe Asn Ile Thr Glu Asp Met Leu Arg Gly Ile Phe Glu Pro Phe Gly
65                  70                  75                  80

Arg Ile Glu Ser Ile Gln Leu Met Met Asp Ser Glu Thr Gly Arg Ser

```
            85                  90                  95
Lys Gly Tyr Gly Phe Ile Thr Phe Ser Asp Ser Glu Cys Ala Lys Lys
            100                 105                 110

Ala Leu Glu Gln Leu Asn Gly Phe Glu Leu Ala Gly Arg Pro Met Lys
            115                 120                 125

Val Gly His Val Thr Glu Arg Thr Asp Ala Ser Ser Ala Ser Ser Phe
            130                 135                 140

Leu Asp Ser Asp Glu Leu Glu Arg Thr Gly Ile Asp Leu Gly Thr Thr
145                 150                 155                 160

Gly Arg Leu Gln Leu Met Ala Arg Leu Ala Glu Gly Thr Gly Leu Gln
            165                 170                 175

Ile Pro Pro Ala Ala Gln Gln Ala Leu Gln Met Ser Gly Ser Leu Ala
            180                 185                 190

Phe Gly Ala Val Ala Glu Phe Ser Phe Val Ile Asp Leu Gln Thr Arg
            195                 200                 205

Leu Ser Gln Gln Thr Glu Ala Ser Ala Leu Ala Ala Ala Ser Val
            210                 215                 220

Gln Pro Leu Ala Thr Gln Cys Phe Gln Leu Ser Asn Met Phe Asn Pro
225                 230                 235                 240

Gln Thr Glu Glu Glu Val Gly Trp Asp Thr Glu Ile Lys Asp Val
            245                 250                 255

Ile Glu Glu Cys Asn Lys His Gly Gly Val Ile His Ile Tyr Val Asp
            260                 265                 270

Lys Asn Ser Ala Gln Gly Asn Val Tyr Val Lys Cys Pro Ser Ile Ala
            275                 280                 285

Ala Ala Ile Ala Ala Val Asn Ala Leu His Gly Arg Trp Phe Ala Gly
            290                 295                 300

Lys Met Ile Thr Ala Ala Tyr Val Pro Leu Pro Thr Tyr His Asn Leu
305                 310                 315                 320

Phe Pro Asp Ser Met Thr Ala Thr Gln Leu Leu Val Pro Ser Arg Arg
            325                 330                 335

<210> SEQ ID NO 42
<211> LENGTH: 453
<212> TYPE: PRT
<213> ORGANISM: Homo sapiens

<400> SEQUENCE: 42

Gly Leu Phe His Leu Lys Ser Ser Leu Arg Lys Asn Ser Ser Ala Leu
1               5                   10                  15

His Ser Leu Leu Lys Arg Val Val Ser Thr Phe Ser Lys Asp Thr Gly
            20                  25                  30

Glu Leu Ala Ser Ser Phe Leu Glu Phe Met Arg Gln Ile Leu Asn Ser
            35                  40                  45

Asp Thr Ile Gly Cys Cys Gly Asp Asp Asn Gly Leu Met Glu Val Glu
50                  55                  60

Gly Ala His Thr Ser Arg Thr Met Ser Ile Asn Ala Ala Glu Leu Lys
65                  70                  75                  80

Gln Leu Leu Gln Ser Lys Glu Glu Ser Pro Glu Asn Leu Phe Leu Glu
            85                  90                  95

Leu Glu Lys Leu Val Leu Glu His Ser Lys Asp Asp Asn Leu Asp
            100                 105                 110

Ser Leu Leu Asp Ser Val Val Gly Leu Lys Gln Met Leu Glu Ser Ser
            115                 120                 125

Gly Asp Pro Leu Pro Leu Ser Asp Gln Asp Val Glu Pro Val Leu Ser
```

```
              130                 135                 140
Ala Pro Glu Ser Leu Gln Asn Leu Phe Asn Asn Arg Thr Ala Tyr Val
145                 150                 155                 160

Leu Ala Asp Val Met Asp Asp Gln Leu Lys Ser Met Trp Phe Thr Pro
                165                 170                 175

Phe Gln Ala Glu Glu Ile Asp Thr Asp Leu Asp Leu Val Lys Val Asp
            180                 185                 190

Leu Ile Glu Leu Ser Glu Lys Cys Cys Ser Asp Phe Asp Leu His Ser
        195                 200                 205

Glu Leu Glu Arg Ser Phe Leu Ser Glu Pro Ser Ser Pro Gly Arg Thr
    210                 215                 220

Lys Thr Thr Lys Gly Phe Lys Leu Gly Lys His Lys His Glu Thr Phe
225                 230                 235                 240

Ile Thr Ser Ser Gly Lys Ser Glu Tyr Ile Glu Pro Ala Lys Arg Ala
                245                 250                 255

His Val Val Pro Pro Pro Arg Gly Arg Gly Arg Gly Phe Gly Gln
            260                 265                 270

Gly Ile Arg Pro His Asp Ile Phe Arg Gln Arg Lys Gln Asn Thr Ser
        275                 280                 285

Arg Pro Pro Ser Met His Val Asp Asp Phe Val Ala Ala Glu Ser Lys
    290                 295                 300

Glu Val Val Pro Gln Asp Gly Ile Pro Pro Lys Arg Pro Leu Lys
305                 310                 315                 320

Val Ser Gln Lys Ile Ser Ser Arg Gly Gly Phe Ser Gly Asn Arg Gly
                325                 330                 335

Gly Arg Gly Ala Phe His Ser Gln Asn Arg Phe Phe Thr Pro Pro Ala
            340                 345                 350

Ser Lys Gly Asn Tyr Ser Arg Arg Glu Gly Thr Arg Gly Ser Ser Trp
        355                 360                 365

Ser Ala Gln Asn Thr Pro Arg Gly Asn Tyr Asn Glu Ser Arg Gly Gly
    370                 375                 380

Gln Ser Asn Phe Asn Arg Gly Pro Leu Pro Leu Arg Pro Leu Ser
385                 390                 395                 400

Ser Thr Gly Tyr Arg Pro Ser Pro Arg Asp Arg Ala Ser Arg Gly Arg
                405                 410                 415

Gly Gly Leu Gly Pro Ser Trp Ala Ser Ala Asn Ser Gly Ser Gly Gly
            420                 425                 430

Ser Arg Gly Lys Phe Val Ser Gly Gly Ser Gly Arg Gly Arg His Val
        435                 440                 445

Arg Ser Phe Thr Arg
    450

<210> SEQ ID NO 43
<211> LENGTH: 162
<212> TYPE: PRT
<213> ORGANISM: Homo sapiens

<400> SEQUENCE: 43

Val Leu Leu Met Phe Asn Glu Gly Asp Gly Phe Ser Phe Glu Glu Ile
1               5                   10                  15

Lys Met Ala Thr Gly Ile Glu Asp Ser Glu Leu Arg Thr Leu Gln
                20                  25                  30

Ser Leu Ala Cys Gly Lys Ala Arg Val Leu Ile Lys Ser Pro Lys Gly
            35                  40                  45

Lys Glu Val Glu Asp Gly Asp Lys Phe Ile Phe Asn Gly Glu Phe Lys
```

```
                  50                  55                  60
His Lys Leu Phe Arg Ile Lys Ile Asn Gln Ile Gln Met Lys Glu Thr
 65                  70                  75                  80

Val Glu Glu Gln Val Ser Thr Thr Glu Arg Val Phe Gln Asp Arg Gln
                 85                  90                  95

Tyr Gln Ile Asp Ala Ala Ile Val Arg Ile Met Lys Met Arg Lys Thr
                100                 105                 110

Leu Gly His Asn Leu Leu Val Ser Glu Leu Tyr Asn Gln Leu Lys Phe
                115                 120                 125

Pro Val Lys Pro Gly Asp Leu Lys Lys Arg Ile Glu Ser Leu Ile Asp
130                 135                 140

Arg Asp Tyr Met Glu Arg Asp Lys Asp Asn Pro Asn Gln Tyr His Tyr
145                 150                 155                 160

Val Ala

<210> SEQ ID NO 44
<211> LENGTH: 346
<212> TYPE: PRT
<213> ORGANISM: Homo sapiens

<400> SEQUENCE: 44

Val Phe Leu Val Asp Phe Glu Phe Gly Cys Ala Thr Ser Tyr Ile Leu
 1               5                  10                  15

Pro Glu Leu Gln Asp Gly Leu Ser Phe His Val Ser Ile Ala Lys Asn
                20                  25                  30

Asp Thr Ile Tyr Ile Leu Gly Gly His Ser Leu Ala Asn Asn Ile Arg
                35                  40                  45

Pro Ala Asn Leu Tyr Arg Ile Arg Val Asp Leu Pro Leu Gly Ser Pro
 50                  55                  60

Ala Val Asn Cys Thr Val Leu Pro Gly Gly Ile Ser Val Ser Ser Ala
 65                  70                  75                  80

Ile Leu Thr Gln Thr Asn Asn Asp Glu Phe Val Ile Val Gly Gly Tyr
                 85                  90                  95

Gln Leu Glu Asn Gln Lys Arg Met Ile Cys Asn Ile Ile Ser Leu Glu
                100                 105                 110

Asp Asn Lys Ile Glu Ile Arg Glu Met Glu Thr Pro Asp Trp Thr Pro
                115                 120                 125

Asp Ile Lys His Ser Lys Ile Trp Phe Gly Ser Asn Met Gly Asn Gly
130                 135                 140

Thr Val Phe Leu Gly Ile Pro Gly Asp Asn Lys Gln Val Val Ser Glu
145                 150                 155                 160

Gly Phe Tyr Phe Tyr Met Leu Lys Cys Ala Glu Asp Asp Thr Asn Glu
                165                 170                 175

Glu Gln Thr Thr Phe Thr Asn Ser Gln Thr Ser Thr Glu Asp Pro Gly
                180                 185                 190

Asp Ser Thr Pro Phe Glu Asp Ser Glu Glu Phe Cys Phe Ser Ala Glu
                195                 200                 205

Ala Asn Ser Phe Asp Gly Asp Asp Glu Phe Asp Thr Tyr Asn Glu Asp
                210                 215                 220

Asp Glu Glu Asp Glu Ser Glu Thr Gly Tyr Trp Ile Thr Cys Cys Pro
225                 230                 235                 240

Thr Cys Asp Val Asp Ile Asn Thr Trp Val Pro Phe Tyr Ser Thr Glu
                245                 250                 255

Leu Asn Lys Pro Ala Met Ile Tyr Cys Ser His Gly Asp Gly His Trp
                260                 265                 270
```

Val His Ala Gln Cys Met Asp Leu Ala Glu Arg Thr Leu Ile His Leu
          275                 280                 285

Ser Ala Gly Ser Asn Lys Tyr Tyr Cys Asn Glu His Val Glu Ile Ala
          290                 295                 300

Arg Ala Leu His Thr Pro Gln Arg Val Leu Pro Leu Lys Lys Pro Pro
305                 310                 315                 320

Met Lys Ser Leu Arg Lys Lys Gly Ser Gly Lys Ile Leu Thr Pro Ala
                325                 330                 335

Lys Lys Ser Phe Leu Arg Arg Leu Phe Asp
            340                 345

<210> SEQ ID NO 45
<211> LENGTH: 547
<212> TYPE: PRT
<213> ORGANISM: Homo sapiens

<400> SEQUENCE: 45

Asn Ser Gly Cys Cys Thr Met Ala Ser Met Gly Thr Leu Ala Phe Asp
1               5                   10                  15

Glu Tyr Gly Arg Pro Phe Leu Ile Ile Lys Asp Gln Asp Arg Lys Ser
            20                  25                  30

Arg Leu Met Gly Leu Glu Ala Leu Lys Ser His Ile Met Ala Ala Lys
        35                  40                  45

Ala Val Ala Asn Thr Met Arg Thr Ser Leu Gly Pro Asn Gly Leu Asp
    50                  55                  60

Lys Met Met Val Asp Lys Asp Gly Asp Val Thr Val Thr Asn Asp Gly
65                  70                  75                  80

Ala Thr Ile Leu Ser Met Met Asp Val Asp His Gln Ile Ala Lys Leu
                85                  90                  95

Met Val Glu Leu Ser Lys Ser Gln Asp Asp Glu Ile Gly Asp Gly Thr
            100                 105                 110

Thr Gly Val Val Val Leu Ala Gly Ala Leu Leu Glu Glu Ala Glu Gln
        115                 120                 125

Leu Leu Asp Arg Gly Ile His Pro Ile Arg Ile Ala Asp Gly Tyr Glu
    130                 135                 140

Gln Ala Ala Arg Val Ala Ile Glu His Leu Asp Lys Ile Ser Asp Ser
145                 150                 155                 160

Val Leu Val Asp Ile Lys Asp Thr Glu Pro Leu Ile Gln Thr Ala Lys
                165                 170                 175

Thr Thr Leu Gly Ser Lys Val Val Asn Ser Cys His Arg Gln Met Ala
            180                 185                 190

Glu Ile Ala Val Asn Ala Val Leu Thr Val Ala Asp Met Glu Arg Arg
        195                 200                 205

Asp Val Asp Phe Glu Leu Ile Lys Val Glu Gly Lys Val Gly Gly Arg
    210                 215                 220

Leu Glu Asp Thr Lys Leu Ile Lys Gly Val Ile Val Asp Lys Asp Phe
225                 230                 235                 240

Ser His Pro Gln Met Pro Lys Lys Val Glu Asp Ala Lys Ile Ala Ile
                245                 250                 255

Leu Thr Cys Pro Phe Glu Pro Pro Lys Pro Lys Thr Lys His Lys Leu
            260                 265                 270

Asp Val Thr Ser Val Glu Asp Tyr Lys Ala Leu Gln Lys Tyr Glu Lys
        275                 280                 285

Glu Lys Phe Glu Glu Met Ile Gln Gln Ile Lys Glu Thr Gly Ala Asn
    290                 295                 300

```
Leu Ala Ile Cys Gln Trp Gly Phe Asp Asp Glu Ala Asn His Leu Leu
305                 310                 315                 320

Leu Gln Asn Asn Leu Pro Ala Val Arg Trp Val Gly Pro Glu Ile
            325                 330                 335

Glu Leu Ile Ala Ile Ala Thr Gly Gly Arg Ile Val Pro Arg Phe Ser
                340                 345                 350

Glu Leu Thr Ala Glu Lys Leu Gly Phe Ala Gly Leu Val Gln Glu Ile
            355                 360                 365

Ser Phe Gly Thr Thr Lys Asp Lys Met Leu Val Ile Glu Gln Cys Lys
    370                 375                 380

Asn Ser Arg Ala Val Thr Ile Phe Ile Arg Gly Gly Asn Lys Met Ile
385                 390                 395                 400

Ile Glu Glu Ala Lys Arg Ser Leu His Asp Ala Leu Cys Val Ile Arg
                405                 410                 415

Asn Leu Ile Arg Asp Asn Arg Val Val Tyr Gly Gly Ala Ala Glu
            420                 425                 430

Ile Ser Cys Ala Leu Ala Val Ser Gln Glu Ala Asp Lys Cys Pro Thr
    435                 440                 445

Leu Glu Gln Tyr Ala Met Arg Ala Phe Ala Asp Ala Leu Glu Val Ile
    450                 455                 460

Pro Met Ala Leu Ser Glu Asn Ser Gly Met Asn Pro Ile Gln Thr Met
465                 470                 475                 480

Thr Glu Val Arg Ala Arg Gln Val Lys Glu Met Asn Pro Ala Leu Gly
                485                 490                 495

Ile Asp Cys Leu His Lys Gly Thr Asn Asp Met Lys Gln Gln His Val
            500                 505                 510

Ile Glu Thr Leu Ile Gly Lys Lys Gln Gln Ile Ser Leu Ala Thr Gln
    515                 520                 525

Met Val Arg Met Ile Leu Lys Ile Asp Asp Ile Arg Lys Pro Gly Glu
530                 535                 540

Ser Glu Glu
545

<210> SEQ ID NO 46
<211> LENGTH: 533
<212> TYPE: PRT
<213> ORGANISM: Homo sapiens

<400> SEQUENCE: 46

Ile Met Ser Lys Leu Ala Gly Glu Ser Glu Ser Asn Leu Arg Lys Ala
1               5                   10                  15

Phe Glu Glu Ala Glu Lys Asn Ala Pro Ala Ile Ile Phe Ile Asp Glu
            20                  25                  30

Leu Asp Ala Ile Ala Pro Lys Arg Glu Lys Thr His Gly Glu Val Glu
        35                  40                  45

Arg Arg Ile Val Ser Gln Leu Leu Thr Leu Met Asp Gly Leu Lys Gln
    50                  55                  60

Arg Ala His Val Ile Val Met Ala Ala Thr Asn Arg Pro Asn Ser Ile
65                  70                  75                  80

Asp Pro Ala Leu Arg Arg Phe Gly Arg Phe Asp Arg Glu Val Asp Ile
                85                  90                  95

Gly Ile Pro Asp Ala Thr Gly Arg Leu Glu Ile Leu Gln Ile His Thr
            100                 105                 110

Lys Asn Met Lys Leu Ala Asp Asp Val Asp Leu Glu Gln Val Ala Asn
        115                 120                 125
```

```
Glu Thr His Gly His Val Gly Ala Asp Leu Ala Ala Leu Cys Ser Glu
    130             135             140
Ala Ala Leu Gln Ala Ile Arg Lys Lys Met Asp Leu Ile Asp Leu Glu
145             150             155             160
Asp Glu Thr Ile Asp Ala Glu Val Met Asn Ser Leu Ala Val Thr Met
                165             170             175
Asp Asp Phe Arg Trp Ala Leu Ser Gln Ser Asn Pro Ser Ala Leu Arg
            180             185             190
Glu Thr Val Val Glu Val Pro Gln Val Thr Trp Glu Asp Ile Gly Gly
        195             200             205
Leu Glu Asp Val Lys Arg Glu Leu Gln Glu Leu Val Gln Tyr Pro Val
    210             215             220
Glu His Pro Asp Lys Phe Leu Lys Phe Gly Met Thr Pro Ser Lys Gly
225             230             235             240
Val Leu Phe Tyr Gly Pro Pro Gly Cys Gly Lys Thr Leu Leu Ala Lys
                245             250             255
Ala Ile Ala Asn Glu Cys Gln Ala Asn Phe Ile Ser Ile Lys Gly Pro
            260             265             270
Glu Leu Leu Thr Met Trp Phe Gly Glu Ser Glu Ala Asn Val Arg Glu
        275             280             285
Ile Phe Asp Lys Ala Arg Gln Ala Ala Pro Cys Val Leu Phe Phe Asp
    290             295             300
Glu Leu Asp Ser Ile Ala Lys Ala Arg Gly Gly Asn Ile Gly Asp Gly
305             310             315             320
Gly Gly Ala Ala Asp Arg Val Ile Asn Gln Ile Leu Thr Glu Met Asp
                325             330             335
Gly Met Ser Thr Lys Lys Asn Val Phe Ile Ile Gly Ala Thr Asn Arg
            340             345             350
Pro Asp Ile Ile Asp Pro Ala Ile Leu Arg Pro Gly Arg Leu Asp Gln
        355             360             365
Leu Ile Tyr Ile Pro Leu Pro Asp Glu Lys Ser Arg Val Ala Ile Leu
    370             375             380
Lys Ala Asn Leu Arg Lys Ser Pro Val Ala Lys Asp Val Asp Leu Glu
385             390             395             400
Phe Leu Ala Lys Met Thr Asn Gly Phe Ser Gly Ala Asp Leu Thr Glu
                405             410             415
Ile Cys Gln Arg Ala Cys Lys Leu Ala Ile Arg Glu Ser Ile Glu Ser
            420             425             430
Glu Ile Arg Arg Glu Arg Glu Arg Gln Thr Asn Pro Ser Ala Met Glu
        435             440             445
Val Glu Glu Asp Asp Pro Val Pro Glu Ile Arg Arg Asp His Phe Glu
    450             455             460
Glu Ala Met Arg Phe Ala Arg Arg Ser Val Ser Asp Asn Asp Ile Arg
465             470             475             480
Lys Tyr Glu Met Phe Ala Gln Thr Leu Gln Gln Ser Arg Gly Phe Gly
                485             490             495
Ser Phe Arg Phe Pro Ser Gly Asn Gln Gly Gly Ala Gly Pro Ser Gln
            500             505             510
Gly Ser Gly Gly Gly Thr Gly Gly Ser Val Tyr Thr Glu Asp Asn Asp
        515             520             525
Asp Asp Leu Tyr Gly
    530
```

```
<210> SEQ ID NO 47
<211> LENGTH: 184
<212> TYPE: PRT
<213> ORGANISM: Homo sapiens

<400> SEQUENCE: 47

Glu Ile Pro Val Val Ala Ile Arg Thr Ala Lys Gly Glu Lys Phe Val
1               5                   10                  15

Met Gln Glu Glu Phe Ser Arg Asp Gly Lys Ala Leu Glu Arg Phe Leu
            20                  25                  30

Gln Asp Tyr Phe Asp Gly Asn Leu Lys Arg Tyr Leu Lys Ser Glu Pro
        35                  40                  45

Ile Pro Glu Ser Asn Asp Gly Pro Val Lys Val Val Ala Glu Asn
    50                  55                  60

Phe Asp Glu Ile Val Asn Asn Glu Asn Lys Asp Val Leu Ile Glu Phe
65                  70                  75                  80

Tyr Ala Pro Trp Cys Gly His Cys Lys Asn Leu Glu Pro Lys Tyr Lys
                85                  90                  95

Glu Leu Gly Glu Lys Leu Ser Lys Asp Pro Asn Ile Val Ile Ala Lys
            100                 105                 110

Met Asp Ala Thr Ala Asn Asp Val Pro Ser Pro Tyr Glu Val Arg Gly
        115                 120                 125

Phe Pro Thr Ile Tyr Phe Ser Pro Ala Asn Lys Lys Leu Asn Pro Lys
    130                 135                 140

Lys Tyr Glu Gly Gly Arg Glu Leu Ser Asp Phe Ile Ser Tyr Leu Gln
145                 150                 155                 160

Arg Glu Ala Thr Asn Pro Pro Val Ile Gln Glu Lys Pro Lys Lys
                165                 170                 175

Lys Lys Lys Ala Gln Glu Asp Leu
            180

<210> SEQ ID NO 48
<211> LENGTH: 514
<212> TYPE: PRT
<213> ORGANISM: Homo sapiens

<400> SEQUENCE: 48

Ile Ile Gln Lys Leu Asn Ile Val Asn Lys Glu Lys Ala Thr Gly
1               5                   10                  15

Arg Glu Val Thr His Ile Gln Phe Thr Ser Trp Pro Asp His Gly Val
            20                  25                  30

Pro Glu Asp Pro His Leu Leu Leu Lys Leu Arg Arg Val Asn Ala
        35                  40                  45

Phe Ser Asn Phe Phe Ser Gly Pro Ile Val Val His Cys Ser Ala Gly
    50                  55                  60

Val Gly Arg Thr Gly Thr Tyr Ile Gly Ile Asp Ala Met Leu Glu Gly
65                  70                  75                  80

Leu Glu Ala Glu Asn Lys Val Asp Val Tyr Gly Tyr Val Val Lys Leu
                85                  90                  95

Arg Arg Gln Arg Cys Leu Met Val Gln Val Glu Ala Gln Tyr Ile Leu
            100                 105                 110

Ile His Gln Ala Leu Val Glu Tyr Asn Gln Phe Gly Glu Thr Glu Val
        115                 120                 125

Asn Leu Ser Glu Leu His Pro Tyr Leu His Asn Met Lys Lys Arg Asp
    130                 135                 140

Pro Pro Ser Glu Pro Ser Pro Leu Glu Ala Glu Phe Gln Arg Leu Pro
145                 150                 155                 160
```

```
Ser Tyr Arg Ser Trp Arg Thr Gln His Ile Gly Asn Gln Glu Glu Asn
                165                 170                 175

Lys Ser Lys Asn Arg Asn Ser Asn Val Ile Pro Tyr Asp Tyr Asn Arg
            180                 185                 190

Val Pro Leu Lys His Glu Leu Glu Met Ser Lys Glu Ser Glu His Asp
        195                 200                 205

Ser Asp Glu Ser Asp Asp Ser Asp Ser Glu Glu Pro Ser Lys
210                 215                 220

Tyr Ile Asn Ala Ser Phe Ile Met Ser Tyr Trp Lys Pro Glu Val Met
225                 230                 235                 240

Ile Ala Ala Gln Gly Pro Leu Lys Glu Thr Ile Gly Asp Phe Trp Gln
                245                 250                 255

Met Ile Phe Gln Arg Lys Val Lys Val Ile Val Met Leu Thr Glu Leu
            260                 265                 270

Lys His Gly Asp Gln Glu Ile Cys Ala Gln Tyr Trp Gly Glu Gly Lys
        275                 280                 285

Gln Thr Tyr Gly Asp Ile Glu Val Asp Leu Lys Asp Thr Asp Lys Ser
    290                 295                 300

Ser Thr Tyr Thr Leu Arg Val Phe Glu Leu Arg His Ser Lys Arg Lys
305                 310                 315                 320

Asp Ser Arg Thr Val Tyr Gln Tyr Gln Tyr Thr Asn Trp Ser Val Glu
                325                 330                 335

Gln Leu Pro Ala Glu Pro Lys Glu Leu Ile Ser Met Ile Gln Val Val
            340                 345                 350

Lys Gln Lys Leu Pro Gln Lys Asn Ser Ser Glu Gly Asn Lys His His
        355                 360                 365

Lys Ser Thr Pro Leu Leu Ile His Cys Arg Asp Gly Ser Gln Gln Thr
    370                 375                 380

Gly Ile Phe Cys Ala Leu Leu Asn Leu Leu Glu Ser Ala Glu Thr Glu
385                 390                 395                 400

Glu Val Val Asp Ile Phe Gln Val Val Lys Ala Leu Arg Lys Ala Arg
                405                 410                 415

Pro Gly Met Val Ser Thr Phe Glu Gln Tyr Gln Phe Leu Tyr Asp Val
            420                 425                 430

Ile Ala Ser Thr Tyr Pro Ala Gln Asn Gly Gln Val Lys Lys Asn Asn
        435                 440                 445

His Gln Glu Asp Lys Ile Glu Phe Asp Asn Glu Val Asp Lys Val Lys
    450                 455                 460

Gln Asp Ala Asn Cys Val Asn Pro Leu Gly Ala Pro Glu Lys Leu Pro
465                 470                 475                 480

Glu Ala Lys Glu Gln Ala Glu Gly Ser Glu Pro Thr Ser Gly Thr Glu
                485                 490                 495

Gly Pro Glu His Ser Val Asn Gly Pro Ala Ser Pro Ala Leu Asn Gln
            500                 505                 510

Gly Ser

<210> SEQ ID NO 49
<211> LENGTH: 262
<212> TYPE: PRT
<213> ORGANISM: Homo sapiens

<400> SEQUENCE: 49

Leu Ser Thr Leu Val Ala Asp Leu Gln Leu Ile Asp Phe Glu Gly Lys
1               5                   10                  15
```

```
Lys Asp Val Ala Gln Ile Phe Asn Asn Ile Leu Arg Arg Gln Ile Gly
             20                  25                  30

Thr Arg Thr Pro Thr Val Glu Tyr Ile Cys Thr Gln Gln Asn Ile Leu
         35                  40                  45

Phe Met Leu Leu Lys Gly Tyr Glu Ser Pro Glu Ile Ala Leu Asn Cys
 50                  55                  60

Gly Ile Met Leu Arg Glu Cys Ile Arg His Glu Pro Leu Ala Lys Ile
 65                  70                  75                  80

Ile Leu Trp Ser Glu Gln Phe Tyr Asp Phe Arg Tyr Val Glu Met
                 85                  90                  95

Ser Thr Phe Asp Ile Ala Ser Asp Ala Phe Ala Thr Phe Lys Asp Leu
            100                 105                 110

Leu Thr Arg His Lys Leu Leu Ser Ala Glu Phe Leu Glu Gln His Tyr
        115                 120                 125

Asp Arg Phe Phe Ser Glu Tyr Glu Lys Leu Leu His Ser Glu Asn Tyr
    130                 135                 140

Val Thr Lys Arg Gln Ser Leu Lys Leu Leu Gly Glu Leu Leu Leu Asp
145                 150                 155                 160

Arg His Asn Phe Thr Ile Met Thr Lys Tyr Ile Ser Lys Pro Glu Asn
                165                 170                 175

Leu Lys Leu Met Met Asn Leu Leu Arg Asp Lys Ser Arg Asn Ile Gln
            180                 185                 190

Phe Glu Ala Phe His Val Phe Lys Val Phe Val Ala Asn Pro Asn Lys
        195                 200                 205

Thr Gln Pro Ile Leu Asp Ile Leu Leu Lys Asn Gln Ala Lys Leu Ile
    210                 215                 220

Glu Phe Leu Ser Lys Phe Gln Asn Asp Arg Thr Glu Asp Gln Phe
225                 230                 235                 240

Asn Asp Glu Lys Thr Tyr Leu Val Lys Gln Ile Arg Asp Leu Lys Arg
                245                 250                 255

Pro Ala Gln Gln Glu Ala
            260

<210> SEQ ID NO 50
<211> LENGTH: 222
<212> TYPE: PRT
<213> ORGANISM: Homo sapiens

<400> SEQUENCE: 50

Val Lys Ser Arg Leu Glu Val Ser Asp Asp Leu Glu Asn Val Cys Asn
1               5                  10                  15

Trp Val Val Asp Thr Cys Leu His Lys Gly Ser Arg Asp Asn Met Ser
             20                  25                  30

Ile Val Leu Val Cys Phe Ser Asn Ala Pro Lys Val Ser Asp Glu Ala
         35                  40                  45

Val Lys Lys Asp Ser Glu Leu Asp Lys His Leu Glu Ser Arg Val Glu
     50                  55                  60

Glu Ile Met Glu Lys Ser Gly Glu Gly Met Pro Asp Leu Ala His
 65                  70                  75                  80

Val Met Arg Ile Leu Ser Ala Glu Asn Ile Pro Asn Leu Pro Pro Gly
                 85                  90                  95

Gly Gly Leu Ala Gly Lys Arg Asn Val Ile Glu Ala Val Tyr Ser Arg
            100                 105                 110

Leu Asn Pro His Arg Glu Ser Asp Gly Ala Ser Asp Glu Ala Glu Glu
        115                 120                 125
```

```
Ser Gly Ser Gln Gly Lys Leu Val Glu Ala Leu Arg Gln Met Arg Ile
        130                 135                 140

Asn His Arg Gly Asn Tyr Arg Gln Leu Leu Glu Met Leu Thr Ser
145                 150                 155                 160

Tyr Arg Leu Ala Lys Val Glu Gly Glu Ser Pro Ala Glu Pro Ala
                165                 170                 175

Ala Thr Ala Thr Ser Ser Asn Ser Asp Ala Gly Asn Pro Val Thr Met
            180                 185                 190

Gln Glu Ser His Thr Glu Ser Glu Ser Gly Leu Ala Glu Leu Asp Ser
                195                 200                 205

Ser Asn Glu Asp Ala Gly Thr Lys Met Ser Gly Glu Lys Ile
        210                 215                 220

<210> SEQ ID NO 51
<211> LENGTH: 104
<212> TYPE: PRT
<213> ORGANISM: Homo sapiens

<400> SEQUENCE: 51

Ala Ser Gln Asn Ile Val Ile Ile Leu Cys Gly Asn Lys Lys Asp Leu
1               5                   10                  15

Asp Ala Asp Arg Glu Val Thr Phe Leu Glu Ala Ser Arg Phe Ala Gln
                20                  25                  30

Glu Asn Glu Leu Met Phe Leu Glu Thr Ser Ala Leu Thr Gly Glu Asn
            35                  40                  45

Val Glu Glu Ala Phe Val Gln Cys Ala Arg Lys Ile Leu Asn Lys Ile
        50                  55                  60

Glu Ser Gly Glu Leu Asp Pro Glu Arg Met Gly Ser Gly Ile Gln Tyr
65                  70                  75                  80

Gly Asp Ala Ala Leu Arg Gln Leu Arg Ser Pro Arg Ala Gln Ala
                85                  90                  95

Pro Asn Ala Gln Glu Cys Gly Cys
            100

<210> SEQ ID NO 52
<211> LENGTH: 131
<212> TYPE: PRT
<213> ORGANISM: Homo sapiens

<400> SEQUENCE: 52

Ala Ile Leu Val Tyr Asp Ile Thr Asp Glu Asp Ser Phe Gln Lys Val
1               5                   10                  15

Lys Asn Trp Val Lys Glu Leu Arg Lys Met Leu Gly Asn Glu Ile Cys
                20                  25                  30

Leu Cys Ile Val Gly Asn Lys Ile Asp Leu Glu Lys Glu Arg His Val
            35                  40                  45

Ser Ile Gln Glu Ala Glu Ser Tyr Ala Glu Ser Val Gly Ala Lys His
        50                  55                  60

Tyr His Thr Ser Ala Lys Gln Asn Lys Gly Ile Glu Glu Leu Phe Leu
65                  70                  75                  80

Asp Leu Cys Lys Arg Met Ile Glu Thr Ala Gln Val Asp Glu Arg Ala
                85                  90                  95

Lys Gly Asn Gly Ser Ser Gln Pro Gly Thr Ala Arg Arg Gly Val Gln
            100                 105                 110

Ile Ile Asp Asp Glu Pro Gln Ala Gln Thr Ser Gly Gly Gly Cys Cys
        115                 120                 125

Ser Ser Gly
```

```
<210> SEQ ID NO 53
<211> LENGTH: 4
<212> TYPE: PRT
<213> ORGANISM: Unknown
<220> FEATURE:
<223> OTHER INFORMATION: Description of Unknown: DEAD-box motif sequence
      peptide

<400> SEQUENCE: 53

Asp Glu Ala Asp
1

<210> SEQ ID NO 54
<211> LENGTH: 4
<212> TYPE: PRT
<213> ORGANISM: Unknown
<220> FEATURE:
<223> OTHER INFORMATION: Description of Unknown: Vif sequence basic
      region peptide

<400> SEQUENCE: 54

Arg Lys Lys Arg
1
```